(12) United States Patent
Bordenstein et al.

(10) Patent No.: US 11,968,963 B2
(45) Date of Patent: Apr. 30, 2024

(54) MALE ARTHROPOD KILLING FACTORS AND METHODS OF USE THEREOF

(71) Applicant: VANDERBILT UNIVERSITY, Nashville, TN (US)

(72) Inventors: Seth Bordenstein, Nashville, TN (US); Jessamyn Perlmutter, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 758 days.

(21) Appl. No.: 16/982,708

(22) PCT Filed: Apr. 5, 2019

(86) PCT No.: PCT/US2019/025936
§ 371 (c)(1),
(2) Date: Sep. 21, 2020

(87) PCT Pub. No.: WO2019/195645
PCT Pub. Date: Oct. 10, 2019

(65) Prior Publication Data
US 2021/0000092 A1 Jan. 7, 2021

Related U.S. Application Data

(60) Provisional application No. 62/652,982, filed on Apr. 5, 2018.

(51) Int. Cl.
| | |
|---|---|
| C07H 21/02 | (2006.01) |
| A01K 67/033 | (2006.01) |
| C07K 14/195 | (2006.01) |
| C12N 15/85 | (2006.01) |

(52) U.S. Cl.
CPC ........ A01K 67/0339 (2013.01); C07K 14/195 (2013.01); C12N 15/85 (2013.01); *A01K 2217/052* (2013.01); *A01K 2227/706* (2013.01)

(58) Field of Classification Search
CPC .................................................. A01K 67/0339
See application file for complete search history.

(56) References Cited

U.S. PATENT DOCUMENTS

| | | | |
|---|---|---|---|
| 7,868,222 B1 | 1/2011 | Dobson | |
| 9,090,911 B2 | 7/2015 | O'Neill et al. | |
| 9,125,388 B2 | 9/2015 | Alphey et al. | |
| 2013/0259846 A1 | 10/2013 | Dobson | |
| 2017/0188559 A1 | 7/2017 | Koukidou et al. | |

FOREIGN PATENT DOCUMENTS

| | | |
|---|---|---|
| WO | 2017/181043 | 10/2017 |
| WO | 2017/185041 | 10/2017 |
| WO | 2017/214476 | 12/2017 |

OTHER PUBLICATIONS

Arai et al. (Frontiers in Microbiology, 2022, 13, 1-15).*
Aliota, Matthew T., et al. "The w Mel strain of Wolbachia reduces transmission of chikungunya virus in Aedes aegypti." PLOS neglected tropical diseases 10.4 (2016): e0004677.
Altschul, S. F., Gish, W., Miller, W., Myers, E. W., & Lipman, D. J. (1990). Basic local alignment search tool. Journal of molecular biology, 215(3), 403-410.
Altschul, S. F., Madden, T. L., Schäffer, A. A., Zhang, J., Zhang, Z., Miller, W., & Lipman, D. J. (1997). Gapped BLAST and PSI-BLAST: a new generation of protein database search programs. Nucleic acids research, 25(17), 3389-3402.
Bankevich, A. et al. SPAdes: a new genome assembly algorithm and its applications to single-cell sequencing. Journal of computational biology: a journal of computational molecular cell biology 19, 455-477, doi: 10.1089/cmb.2012.0021 (2012).
Baumhover, A. H., et al. "Field observations on the effects of releasing sterile screw-worms in Florida." Journal of Economic Entomology 52.6 (1959): 1202-1206.
Baumhover, Alfred H. "Eradication of the screwworm fly: an agent of myiasis." JAMA 196.3 (1966): 240-248.
Baumhover, et al., Screw-Worm Control Through Release of Sterilized Flies, Journal of Economic Entomology, vol. 48, Issue 4, Aug. 1, 1955, pp. 462-466, https://doi.org/10.1093/jee/48.4.462.
Baym, M. et al. Inexpensive multiplexed library preparation for megabase-sized genomes. PloS one 10, e0128036, doi:10.1371/journal.pone.0128036 (2015).
Beaucage, S. L., & Caruthers, M. H. (1981). Deoxynucleoside phosphoramidites—a new class of key intermediates for deoxypolynucleotide synthesis. Tetrahedron Letters, 22(20), 1859-1862.
Beckmann, J. F., Ronau, J. A. & Hochstrasser, M. A Wolbachia deubiquitylating enzyme induces cytoplasmic incompatibility. Nature microbiology 2, 17007, doi:10.1038/nmicrobiol.2017.7 (2017).
Benedict, Mark Q., and Alan S. Robinson. "The first releases of transgenic mosquitoes: an argument for the sterile insect technique." Trends in parasitology 19.8 (2003): 349-355.
Berec, L., Maxin, D. & Bernhauerova, V. Male-killing bacteria as agents of insect pest control. Journal of Applied Ecology (2016).
Boetzer, M. & Pirovano, W. Toward almost closed genomes with GapFiller. Genome biology 13, R56, doi:10.1186/gb-2012-13-6-r56 (2012).
Bordenstein, S. R. & Bordenstein, S. R. Eukaryotic association module in phage WO genomes from Wolbachia. Nat Commun 7, 13155, doi:10.1038/ncomms13155 (2016).
Bordenstein, S. R., O'Hara, F. P. & Werren, J. H. Wolbachia-induced incompatibility precedes other hybrid incompatibilities in Nasonia. Nature 409, 707-710, doi:10.1038/35055543 (2001).

(Continued)

*Primary Examiner* — Amy H Bowman
(74) *Attorney, Agent, or Firm* — Meunier Carlin & Curfman LLC

(57) ABSTRACT

The present disclosure relates to genetically modified arthropods, genetically modified bacteria, and methods for controlling and/or reducing arthropod populations.

19 Claims, 16 Drawing Sheets

Specification includes a Sequence Listing.

(56) References Cited

OTHER PUBLICATIONS

Brelsfoard, Corey L., and Stephen L. Dobson. "Wolbachia-based strategies to control insect pests and disease vectors." Asia Pac. J. Mol. Biol. Biotechnol 17.3 (2009): 55-63.
Brucker, R. M. & Bordenstein, S. R. Speciation by symbiosis. Trends Ecol Evol 27, 443-451, doi:10.1016/j.tree.2012.03.011 (2012).
Bushland, B. C., A. W. Lindquist, and E. F. Kipling. "Eradication of Screw-Worms through Release of Sterilized Males." Science (Washington) 122 (1955): 287-8.
Bushland, R. C., and D. E. Hopkins. "Experiments with screw-worm flies sterilized by X-rays." Journal of Economic Entomology 44.5 (1951).
Carson, H. L. A female-producing strain of D. borealis Patterson. Drosoph. Inf. Serv 30, 109-110 (1956).
Cheng, B., Kuppanda, N., Aldrich, J. C., Akbari, O. S. & Ferree, P. M. Male-Killing Spiroplasma Alters Behavior of the Dosage Compensation Complex during Drosophila melanogaster Embryogenesis. Curr Biol 26, 1339-1345, doi: 10.1016/j.cub.2016.03.050 (2016).
Dame, David A., et al. "Historical applications of induced sterilisation in field populations of mosquitoes." Malaria journal 8.2 (2009): 1-10.
Dutra, H. L. et al. Wolbachia Blocks Currently Circulating Zika Virus Isolates in Brazilian Aedes aegypti Mosquitoes. Cell Host Microbe 19, 771-774, doi:10.1016/j.chom.2016.04.021 (2016).
Dyer, K. A. & Jaenike, J. Evolutionarily stable infection by a male-killing endosymbiont in Drosophila innubila: molecular evidence from the host and parasite genomes. Genetics 168, 1443-1455, doi:10.1534/genetics.104.027854 (2004).
Ellegaard, K. M., Klasson, L., Naslund, K., Bourtzis, K. & Andersson, S. G. Comparative genomics of Wolbachia and the bacterial species concept. PLoS genetics 9, e1003381, doi: 10.1371/journal.pgen.1003381 (2013).
Engelstadter, J. & Hurst, G. D. The impact of male-killing bacteria on host evolutionary processes. Genetics 175, 245-254, doi:10.1534/genetics.106.060921 (2007).
Henikoff, S., & Henikoff, J. G. (1992). Amino acid substitution matrices from protein blocks. Proceedings of the National Academy of Sciences, 89(22), 10915-10919.
Hoffmann, A. A. et al. Successful establishment of Wolbachia in Aedes populations to suppress dengue transmission. Nature 476, 454-457, doi:10.1038/nature10356 (2011).
Hornett, E. A. et al. Evolution of male-killer suppression in a natural population. PLoS Biol 4, e283, doi:10.1371/journal.pbio.0040283 (2006).
Hornett, E. A. et al. You can't keep a good parasite down: evolution of a male-killer suppressor uncovers cytoplasmic incompatibility. Evolution 62, 1258-1263, doi:10.1111/j.1558-5646.2008.00353.x (2008).
Hughes, Grant L., et al. "Native microbiome impedes vertical transmission of Wolbachia in Anopheles mosquitoes." Proceedings of the National Academy of Sciences 111.34 (2014): 12498-12503.
Hughes, Grant L., et al. "Wolbachia infections are virulent and inhibit the human malaria parasite Plasmodium falciparum in Anopheles gambiae." PLoS Pathog 7.5 (2011): e1002043.
Hurst, G. D. & Jiggins, F. M. Male-killing bacteria in insects: mechanisms, incidence, and implications. Emerg Infect Dis 6, 329-336, doi:10.3201/eid0604.000402 (2000).
Hurst, G. D. & McVean, G. A. T. Parasitic male-killing bacteria and the evolution of clutch size. Ecological entomology 23, 350-353 (1998).
Hurst, G. D., Johnson, A. P., Schulenburg, J. H. & Fuyama, Y. Male-killing Wolbachia in Drosophila: a temperature-sensitive trait with a threshold bacterial density. Genetics 156, 699-709 (2000).
Jaenike, J. Spontaneous emergence of a new Wolbachia phenotype. Evolution 61, 2244-2252, doi:10.1111/j.1558-5646.2007.00180.x (2007).
Jaenike, J., Dyer, K. A., Cornish, C. & Minhas, M. S. Asymmetrical reinforcement and Wolbachia infection in Drosophila. PLoS Biol 4, e325, doi:10.1371/journal.pbio.0040325 (2006).

Jiggins, F. M., Hurst, G. D. & Majerus, M. E. Sex-ratio-distorting Wolbachia causes sex-role reversal in its butterfly host. Proc Biol Sci 267, 69-73, doi:10.1098/rspb.2000.0968 (2000).
Karlin, S., & Altschul, S. F. (1993). Applications and statistics for multiple high-scoring segments in molecular sequences. Proceedings of the National Academy of Sciences, 90(12), 5873-5877.
Kelley, L. A., Mezulis, S., Yates, C. M., Wass, M. N. & Sternberg, M. J. The Phyre2 web portal for protein modeling, prediction and analysis. Nature protocols 10, 845-858, doi: 10.1038/nprot.2015.053 (2015).
Kim, M. et al. Noncanonical DNA-binding mode of repressor and its disassembly by antirepressor. Proceedings of the National Academy of Sciences of the United States of America 113, E2480-2488, doi:10.1073/pnas.1602618113 (2016).
Knipling, E. F. "Possibilities of insect control or eradication through the use of sexually sterile males." Journal of Economic Entomology 48.4 (1955): 459-462.
Lacroix, Renaud, et al. "Open field release of genetically engineered sterile male Aedes aegypti in Malaysia." PloS one 7.8 (2012): e42771.
Landmann, F., Orsi, G. A., Loppin, B. & Sullivan, W. Wolbachia-mediated cytoplasmic incompatibility is associated with impaired histone deposition in the male pronucleus. PLoS pathogens 5, e1000343, doi:10.1371/journal.ppat.1000343 (2009).
Laven, H. "Eradication of Culex pipiens fatigans through cytoplasmic incompatibility." Nature 216.5113 (1967): 383-384.
Lees, Rosemary Susan, et al. "Back to the future: the sterile insect technique against mosquito disease vectors." Current Opinion in Insect Science 10 (2015): 156-162.
LePage, D. & Bordenstein, S. R. Wolbachia: Can we save lives with a great pandemic? Trends Parasitol 29, 385-393, doi:10.1016/j.pt.2013.06.003 (2013).
LePage, D. P. et al. Prophage WO genes recapitulate and enhance Wolbachia-induced cytoplasmic incompatibility. Nature 543, 243-247, doi:10.1038/nature21391 (2017).
Lindquist, D. A., M. Abusowa, and M. J. R. Hall. "The New World screwworm fly in Libya: a review of its introduction and eradication." Medical and Veterinary Entomology 6.1 (1992): 2-8.
Longdon, B., Fabian, D. K., Hurst, G. D. & Jiggins, F. M. Male-killing Wolbachia do not protect Drosophila bifasciata against viral infection. BMC microbiology 12 Suppl 1, S8, doi:10.1186/1471-2180-12-s1-s8 (2012).
Luscombe, N. M., Austin, S. E., Berman, H. M. & Thornton, J. M. An overview of the structures of protein-DNA complexes. Genome biology 1, Reviews001, doi:10.1186/gb-2000-1-1-reviews001 (2000).
Mains, James W., et al. "Female adult Aedes albopictus suppression by Wolbachia-infected male mosquitoes." Scientific reports 6 (2016): 33846.
Majerus, T. M. & Majerus, M. E. Intergenomic arms races: detection of a nuclear rescue gene of male-killing in a ladybird. PLoS pathogens 6, e1000987, doi:10.1371/journal.ppat.1000987 (2010).
Matteucci, M. D., & Caruthers, M. H. (1981). Synthesis of deoxyoligonucleotides on a polymer support. Journal of the American Chemical Society, 103(11), 3185-3191.
Metcalf, J. A., Jo, M., Bordenstein, S. R., Jaenike, J. & Bordenstein, S. R. Recent genome reduction of Wolbachia in Drosophila recens targets phage WO and narrows candidates for reproductive parasitism. PeerJ 2, e529, doi:10.7717/peerj.529 (2014).
Petrella, L. N., Smith-Leiker, T. & Cooley, L. The Ovhts polyprotein is cleaved to produce fusome and ring canal proteins required for Drosophila oogenesis. Development 134, 703-712, doi:10.1242/dev.02766 (2007).
Pinto, S. B. et al. Transcriptional regulation of Culex pipiens mosquitoes by Wolbachia influences cytoplasmic incompatibility. PLoS pathogens 9, e1003647, doi:10.1371/journal.ppat.1003647 (2013).
Riparbelli, M. G., Giordano, R., Ueyama, M. & Callaini, G. Wolbachia-mediated male killing is associated with defective chromatin remodeling. PLoS one 7, e30045, doi:10.1371/journal.pone.0030045 (2012).
Sasaki, T., Kubo, T. & Ishikawa, H. Interspecific transfer of Wolbachia between two lepidopteran insects expressing cytoplasmic incom-

(56) References Cited

OTHER PUBLICATIONS patibility: a Wolbachia variant naturally infecting Cadra cautella causes male killing in Ephestia kuehniella. Genetics 162, 1313-1319 (2002).

Sheeley, S. L. & McAllister, B. F. Mobile male-killer: similar Wolbachia strains kill males of divergent *Drosophila* hosts. Heredity 102, 286-292, doi:10.1038/hdy.2008.126 (2009).

Sinkins, Steven P. "Wolbachia and cytoplasmic incompatibility in mosquitoes." Insect biochemistry and molecular biology 34.7 (2004): 723-729.

Sinkins, Steven P., and Fred Gould. "Gene drive systems for insect disease vectors." Nature Reviews Genetics 7.6 (2006): 427-435.

Sutton, E. R., Harris, S. R., Parkhill, J. & Sinkins, S. P. Comparative genome analysis of Wolbachia strain wAu. BMC genomics 15, 928, doi:10.1186/1471-2164-15-928 (2014).

Telschow, A., Hammerstein, P. & Werren, J. H. The effect of Wolbachia versus genetic incompatibilities on reinforcement and speciation. Evolution 59, 1607-1619 (2005).

Walker, T. J. P. H., et al. "The w Mel Wolbachia strain blocks dengue and invades caged Aedes aegypti populations." Nature 476.7361 (2011): 450-453.

International Search Report and Written Opinion dated Jul. 5, 2019, from International Application No. PCT/US2019/025936, 13 pages.

Sutton et al. "Comparative genome analysis of Wolbachia strain wAu", BMC Genomics 2014, 15:928.

Riparbelli et al. "Wolbachia-Mediated Male Killing is Associated with Defective Chromatin Remodeling", PLOS One, Jan. 2012, vol. 7, issue 1, 14 pages.

\* cited by examiner c d

MALE ARTHROPOD KILLING FACTORS AND METHODS OF USE THEREOF

CROSS REFERENCE TO RELATED APPLICATIONS

This application is a 371 of PCT International Application No. PCT/US2019/025936, filed Apr. 5, 2019, which claims the benefit of U.S. Provisional Patent Application Ser. No. 62/652,982, filed Apr. 5, 2018, which are expressly incorporated herein by reference.

STATEMENT REGARDING FEDERALLY SPONSORED RESEARCH

This invention was made with government support under Grant Nos. HD086833, AI133522, AI132581, CA068485, DK020593, DK058404, DK059637 and EY008126 awarded by the National Institutes of Health and under Grant No. 1456778 awarded by the National Science Foundation. The government has certain rights in the invention.

FIELD

The present disclosure relates to genetically modified arthropods, genetically modified bacteria, and methods for controlling and/or reducing arthropod populations.

BACKGROUND

*Wolbachia* are maternally-transmitted bacteria that infect almost half of all arthropod species and many nematode species. In arthropods, these bacteria often selfishly manipulate host reproduction to enhance the fitness of infected females, thereby facilitating their own transmission and spread through the host population. Despite significant impacts of *Wolbachia* on animal reproduction, evolution, and vector control, the bacterial genes underlying most of these reproductive manipulations remain elusive. One such phenotype is male killing, where the sons of infected females are selectively killed. What is needed are novel compositions and methods that can recapitulate the male killing phenotype in order to improve vector control and thus reduce transmission of vector-borne diseases.

The compounds, compositions, and methods disclosed herein address these and other needs.

SUMMARY

Disclosed herein are genetically modified arthropods and genetically modified bacteria useful for controlling and/or reducing populations of arthropods (for example, insects). The inventors have identified a gene, hereafter denoted WO male killing (wmk) [or WD0626 (also referred to as locus number WD_RS02815)], that causes male lethality when transgenically expressed, which leads to a female-biased sex ratio. These male arthropod-killing genes encoding male arthropod killing factors are used to genetically modify arthropods in order to reduce a population of target arthropods, such as vectors of disease or agricultural pests. In addition, the methods of using these male arthropod-killing factors can be combined with additional methods for vector control, for example, sterile insect techniques (SIT) or incompatible insect techniques (IIT).

In some aspects, disclosed herein is a genetically modified arthropod, said arthropod comprising:
a gene encoding a male arthropod killing factor; and
a promoter operably linked to the gene encoding the male arthropod killing factor;
wherein the expression of the gene encoding the male arthropod killing factor in arthropod embryos causes a reduction in viable surviving male offspring in comparison to arthropod embryos not expressing the gene encoding the male arthropod killing factor.

In some embodiments, the gene encoding the male arthropod killing factor is from a bacterium. In some embodiments, the gene encoding the male arthropod killing factor is from a phage or prophage. In some embodiments, the gene encoding the male arthropod killing factor is from *Wolbachia* (or prophage WO or phage WO). In some embodiments, the male arthropod killing factor is wmk (WD0626) or its homologs. In some embodiments, the male arthropod killing factor comprises the amino acid sequence SEQ ID NO:1, or a variant thereof.

In some embodiments, the reduction in viable male offspring is greater than 10%.

In some embodiments, the arthropod is an insect. In some embodiments, the insect is selected from the genera consisting of *Aedes, Culex* and *Anopheles*. In some embodiments, the insect is selected from the group consisting of *Aedes albopictus, Aedes aegypti* and *Aedes polynesiensis*. In some embodiments, the insect is *Drosophila suzukii*.

In some aspects, disclosed herein is a method for controlling a population of target arthropods, comprising:
providing a gene encoding a male arthropod killing factor, and a promoter operably linked to the gene encoding the male arthropod killing factor;
transforming a population of arthropods with the gene encoding the male arthropod killing factor and the promoter operably linked to the gene encoding the male arthropod-killing factor; and
releasing the population of arthropods amongst a population of target arthropods, wherein the release of the arthropods reduces the population of target arthropods.

In some aspects, disclosed herein is a method for controlling a population of target arthropods, comprising:
providing a gene encoding a male arthropod killing factor, and a promoter operably linked to the gene encoding the male arthropod killing factor;
genetically transforming a bacteria, phage, or prophage with the gene encoding the male arthropod killing factor operably linked to the promoter;
transinfecting a population of arthropods with the bacteria, phage, or prophage; and
releasing the population of arthropods amongst a population of target arthropods, wherein the release of the arthropods reduces the population of target arthropods.

In some embodiments, the method further comprises providing an additional method of arthropod control. In some embodiments, the additional method of arthropod control is a sterile insect technique (SIT). In some embodiments, the additional method of arthropod control is an incompatible insect technique (IIT).

BRIEF DESCRIPTION OF THE DRAWINGS

The accompanying figures, which are incorporated in and constitute a part of this specification, illustrate several aspects described below.

Figure 2:
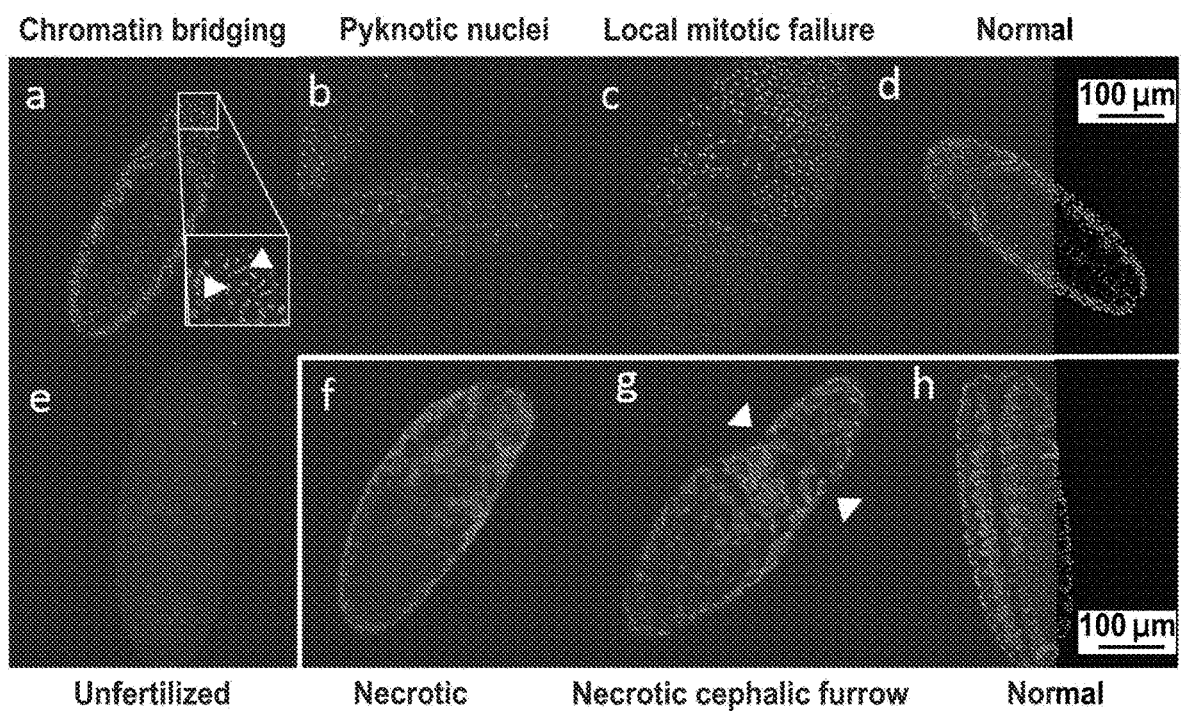
Figure 2:
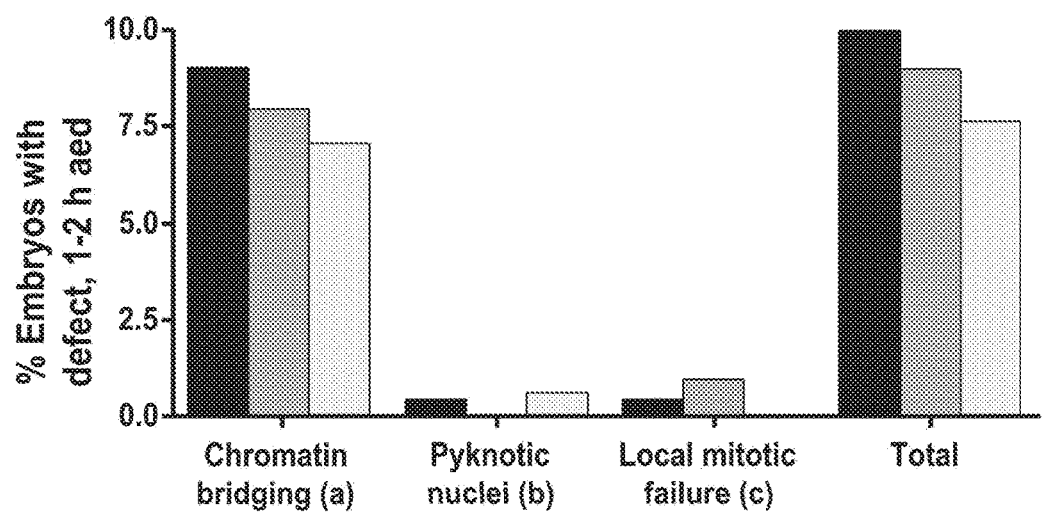
Figure 2:
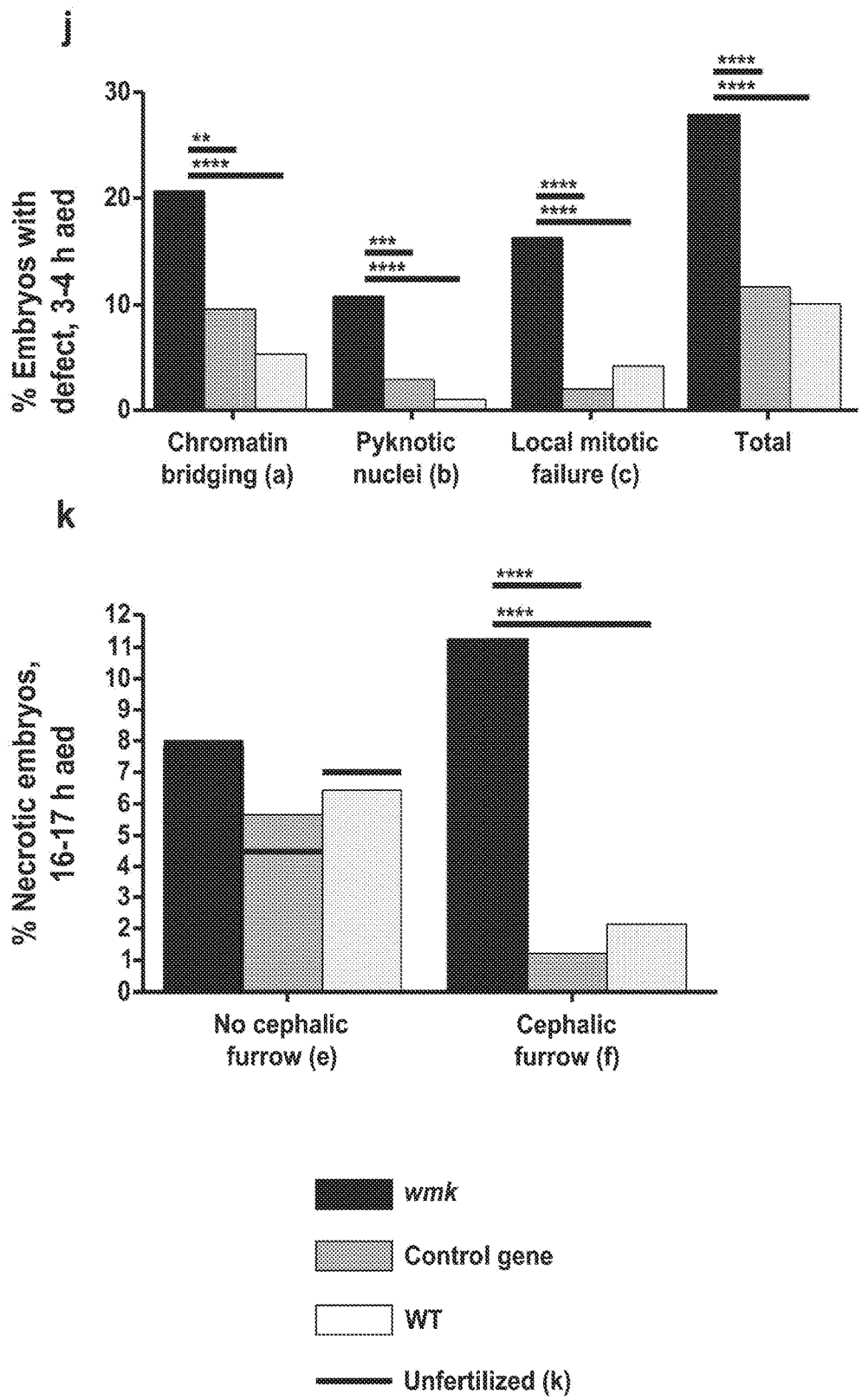

FIG. 2. Transgenic expression of wmk causes cytological defects in early embryogenesis. Images and data are from pooled embryos (both sexes, expressing and non-expressing) with either wmk, the control gene, or an uninfected wild type (WT) background (see methods). (a-c) Defective wmk embryos fixed 3-4 h after egg deposition (aed) exhibit either chromatin bridging (arrowheads, this embryo also shows local mitotic failure), pyknotic nuclei, or local mitotic failure leading to gaps in the distribution of nuclei, respectively. (d) Image of a normal control gene embryo fixed 3-4 h aed. (e) Image of unfertilized embryo fixed approximately 3-4 h aed. (f) Image of necrotic wmk embryo fixed 16-17 h aed with no distinct nuclei and no visible segmentation. (g) Image of a necrotic wmk embryo fixed 16-17 h aed with no distinct nuclei, but the cephalic furrow is present. (f) and (g) are brightened in order to see their differences. (h) Image of normal control gene embryo fixed 16-17 h aed. (i) Graph quantitating the percentage of embryos exhibiting DNA defects that were fixed 1-2 h aed. N=220 for the wmk cross, N=200 for the control gene cross, and N=169 for the WT cross. Total refers to the total percentage of embryos with one or more of the three defects (embryos can have more than one, as in (a)). All differences within each defect category were not statistically significant. (j) Graph of the percentage of embryos exhibiting DNA defects that were fixed 3-4 h aed for wmk, control gene, and WT crosses. N=276 for the wmk cross, N=273 for the WT cross, and N=279 for the control transgene cross. (k) Graph of the percentage of necrotic embryos fixed 16-17 h aed in the wmk, control gene, and WT crosses. N=327 for the wmk cross, N=315 for the control transgene cross, and N=231 for the WT cross. The percent of unfertilized eggs is the expected percent given the observed rate of unfertilized sibling eggs fixed 3-4 h aed (wmk, 8%, N=324; control gene, 4.5%, N=202; WT, 7%, N=217). Statistics for (i), (j), and (k) were performed with a Chi-square test comparing the three genotypes within each defect category. These experiments have been performed once. The white border around (f, g, & h) indicates embryos fixed 16-17 h aed, while the rest (a-e) are embryos fixed 3-4 h aed. All images were taken at 20× zoom, except the inset image in (a) that is a zoomed in image of the same region. All other images were taken as a part of this experiment. p<0.01, *p<0.001, ****p<0.0001.

Figure 3:
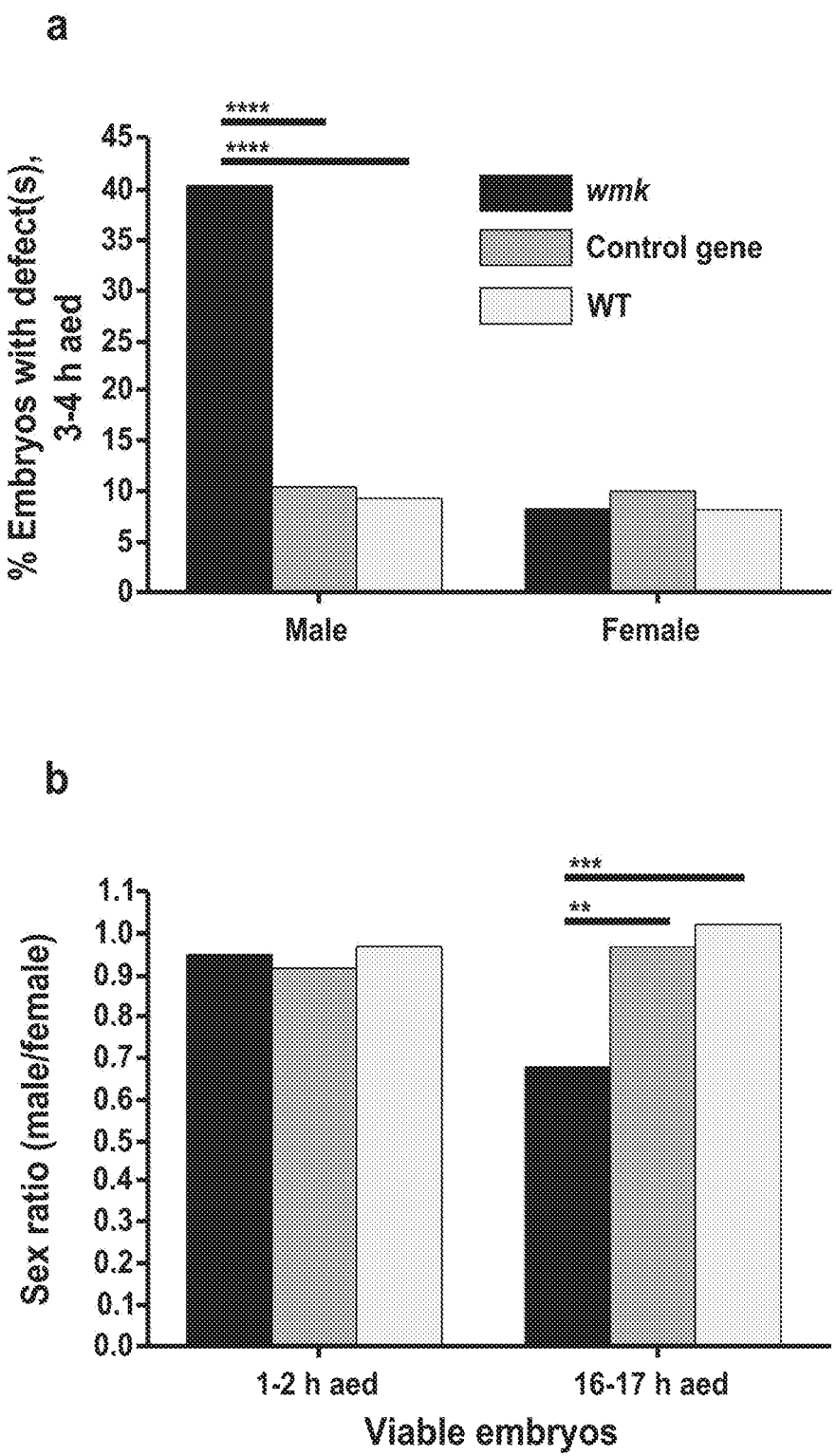

FIG. 3. wmk-induced embryonic defects are enriched in males. Images and data were gathered from pooled embryos (both sexes, expressing and non-expressing, see methods) with either wmk, the control gene, or a WT background. (a) Graph quantitating the percentage of 3-4 h aed embryos that have at least one defect, broken down by sex (wmk males N=228, control gene males N=190, WT males N=170, wmk females N=240, control gene females N=200, WT females N=158). (b) Graph quantitating the sex ratio of viable embryos (not necrotic, no visible defects) broken down by development time (1-2 h wmk N=105 m, 111 f; 1-2 h control gene N=30 m, 141 f; 1-2 h WT N=112 m, 115 f; 16-17 h wmk N=104 m, 154 f; 16-17 h control gene N=116 m, 120 f; 16017 h WT N=110 m, 108 f). m=male, f=female. Statistics were performed with a Chi-square test comparing the three genotypes within each category (male or female in (a) and 1-2 h or 16-17 h in (b)). These experiments were performed once. p<0.01, *p<0.001, ****p<0.0001.

Figure 4:
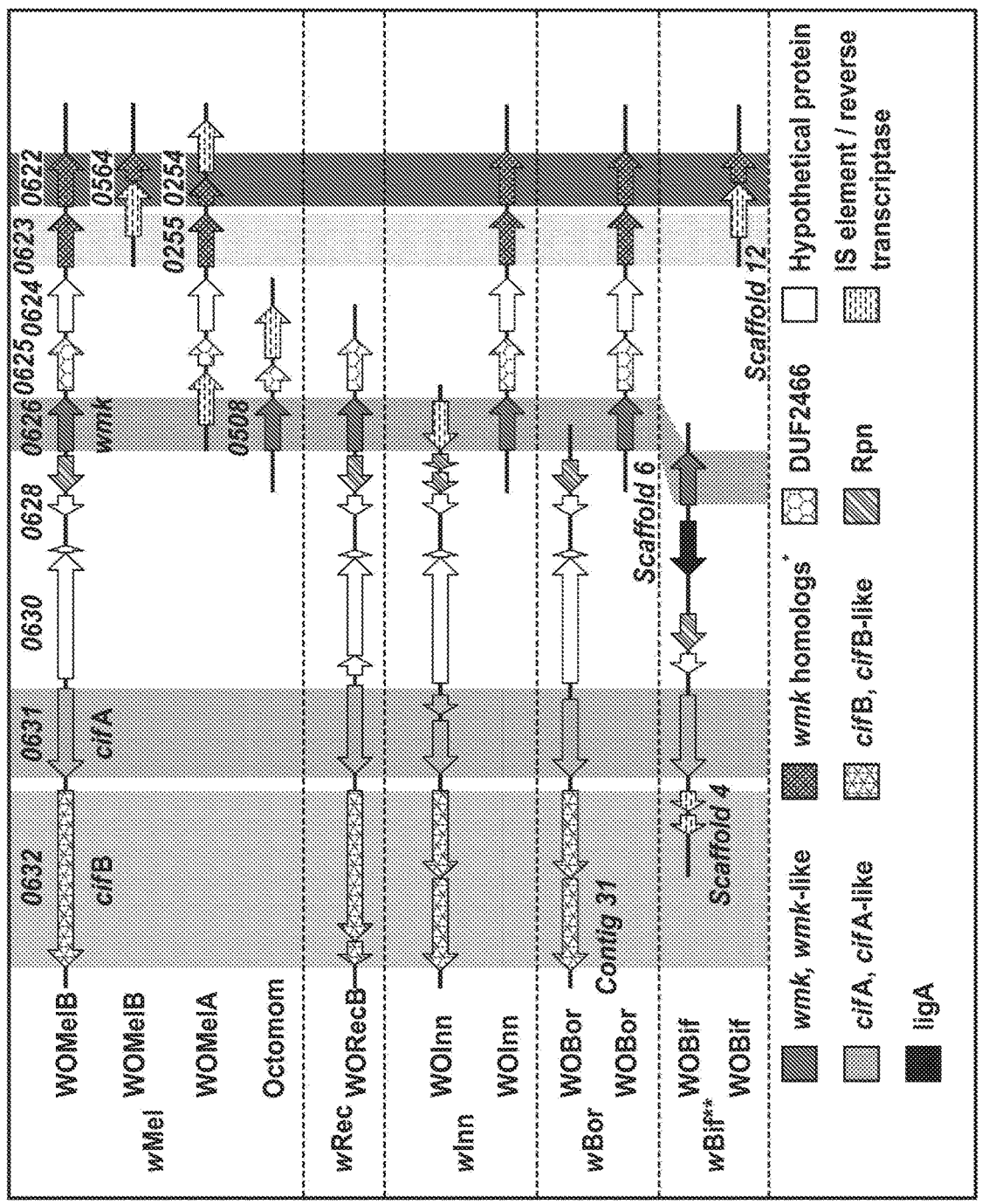

FIG. 4. Comparative genomics of wmk and its homologs in wMel and male-killing strains. Prophage WO gene regions containing wmk, its homologs, and CI genes cifA and cifB, organized by Wolbachia strain. At least one wmk homolog is associated with each Wolbachia-induced male-killing strain. The sequence length difference between wmk and cifA is approximately 5 kb in wMel. Shading highlights homologs of each gene in each strain. If regions are connected by a line, they are contiguously sequenced. Regions from a given Wolbachia strain that are not connected are either in different prophage WO regions (in the case of wMel), or the sequences are on different contigs (in the cases of wBif, wBor, and wInn). (*) These genes were disrupted by a transposase and are therefore truncated. () wmk homologs are annotated as transcriptional regulators in the Wolbachia reference genomes and encode HTH_XRE domains (Table 1). (*) While wBif reportedly induces weak CI after temperature treatment[12]; the assembled genome does not contain cifB. However, low coverage of raw reads to the wMel cifB sequence were observed, so it may be present in low copy number. While wBif reportedly induces weak CI after temperature treatment, the assembled genome does not contain cifB.

Figure 5:
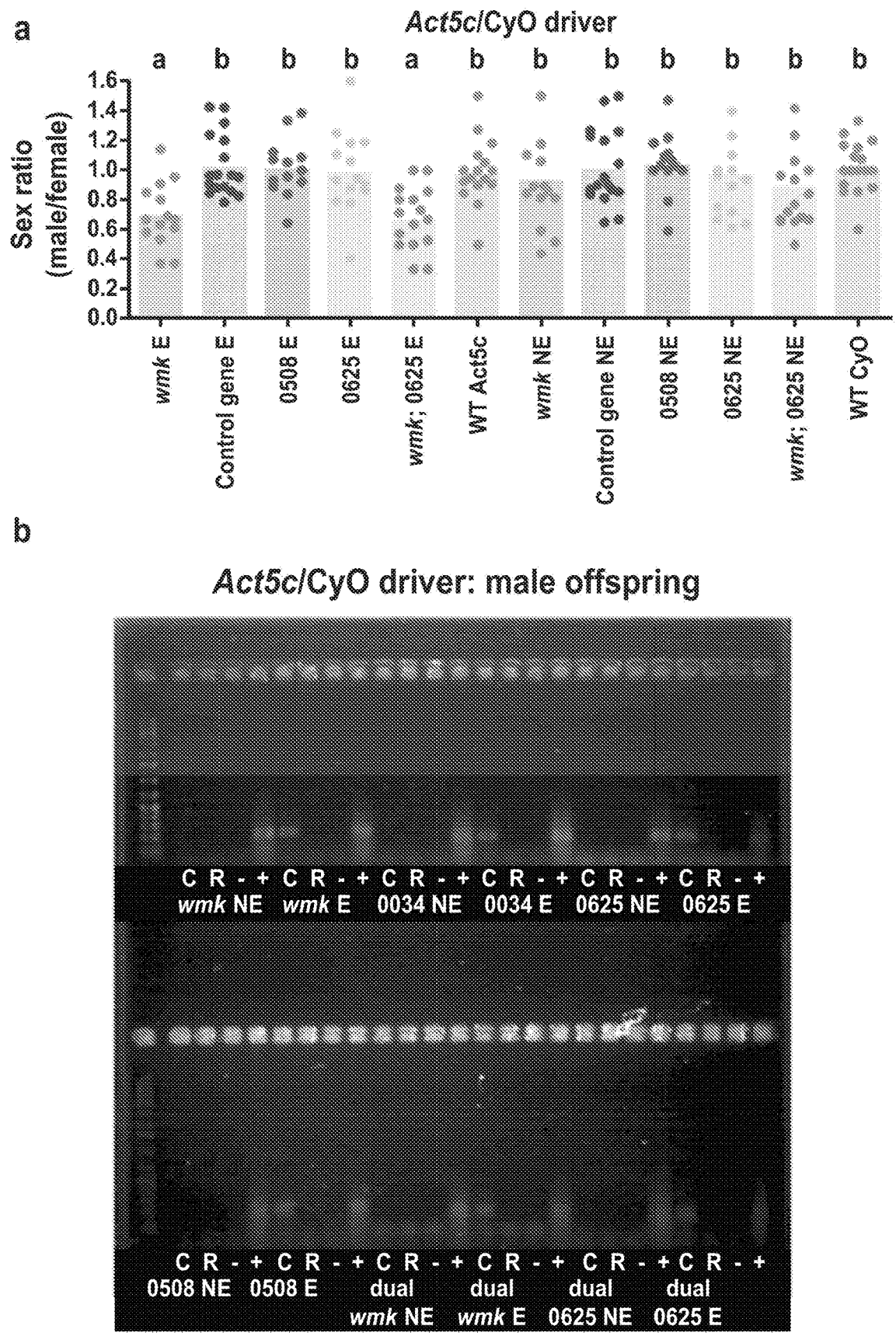
Figure 5:
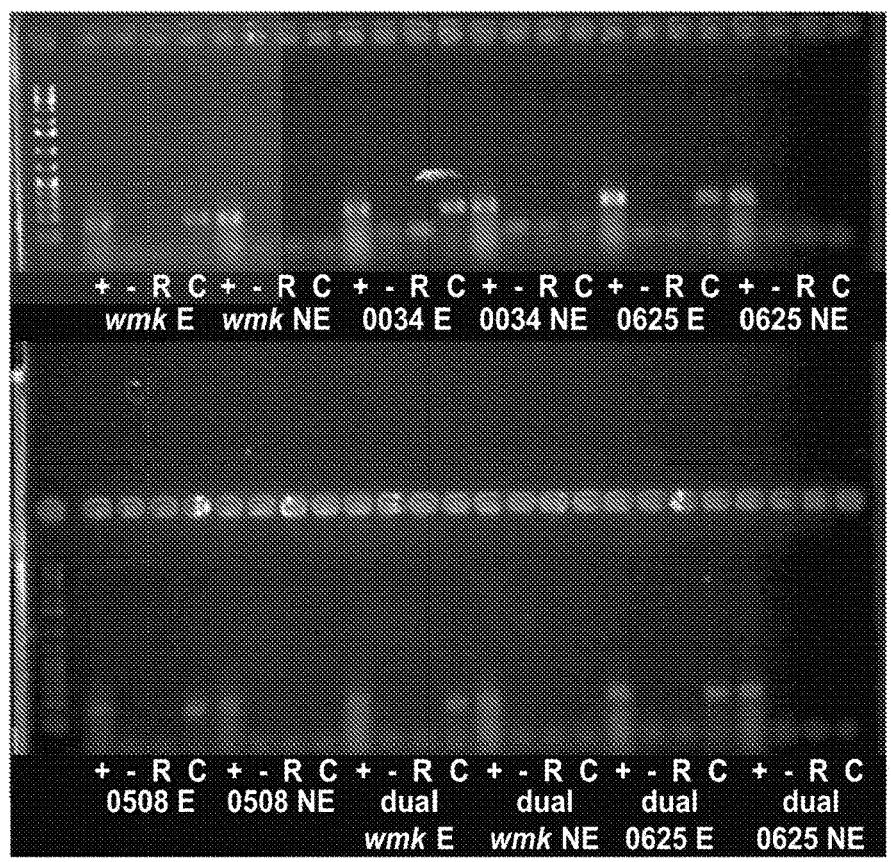
Figure 5:
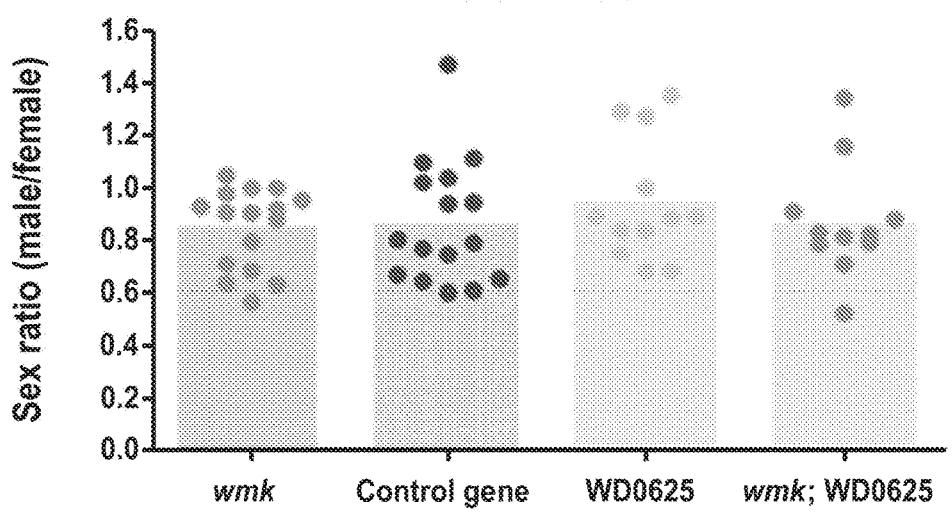
Figure 5:
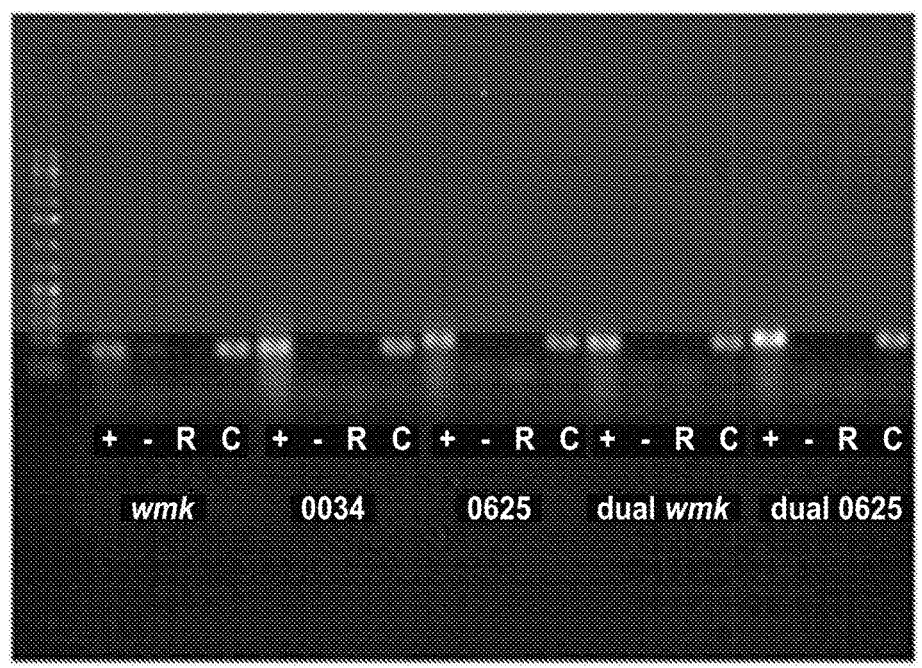
Figure 6:
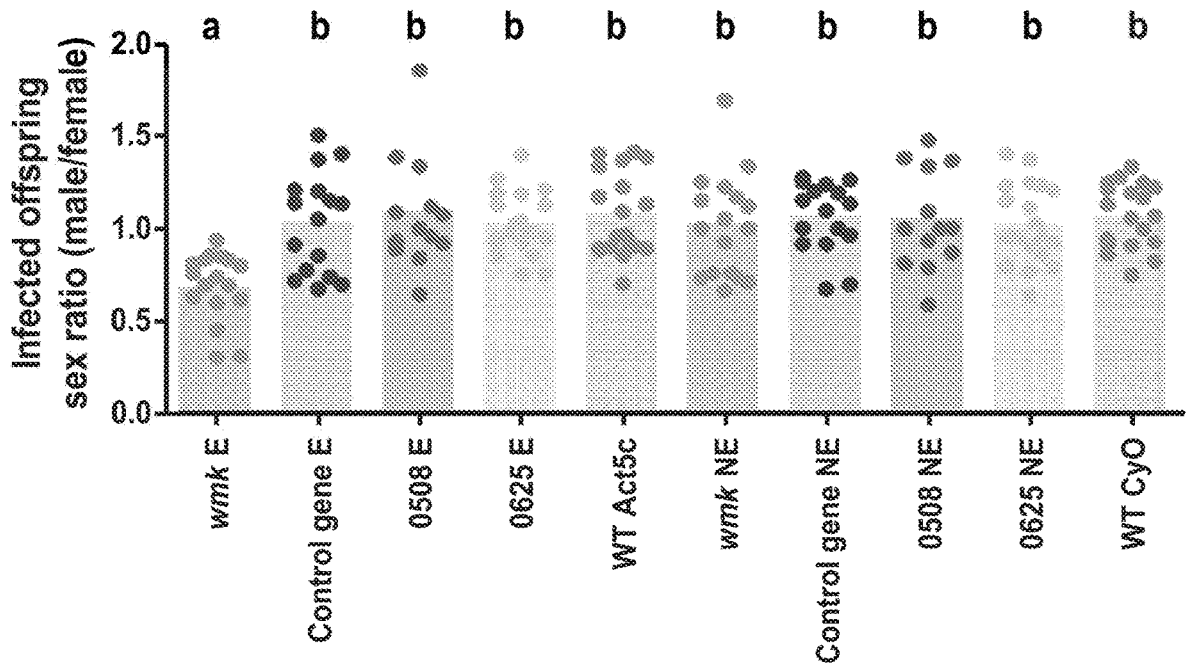
Figure 6:
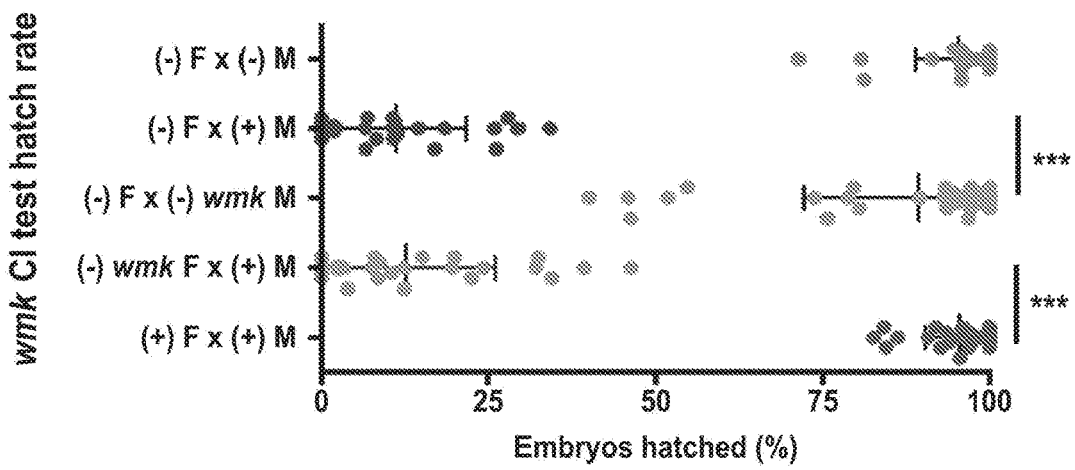
Figure 6:
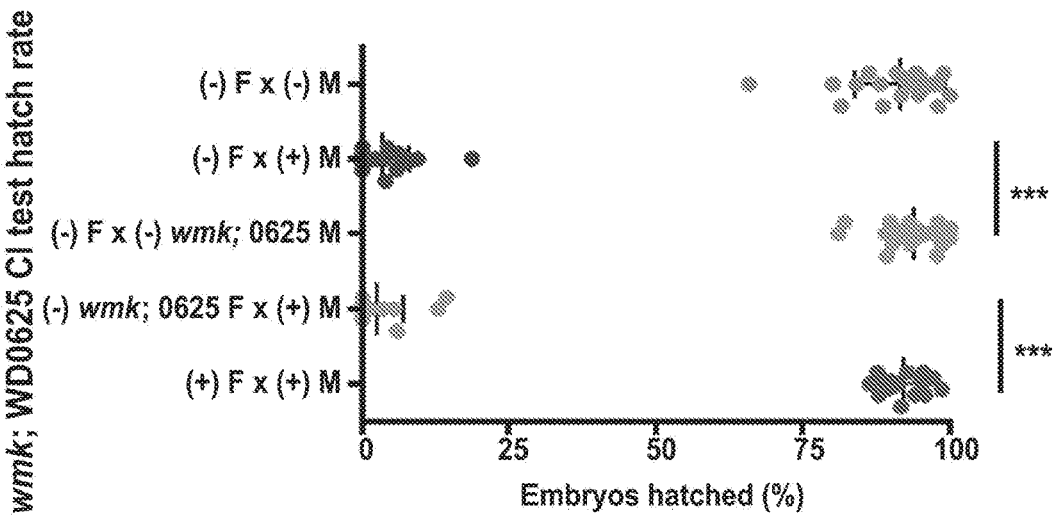
Figure 6:
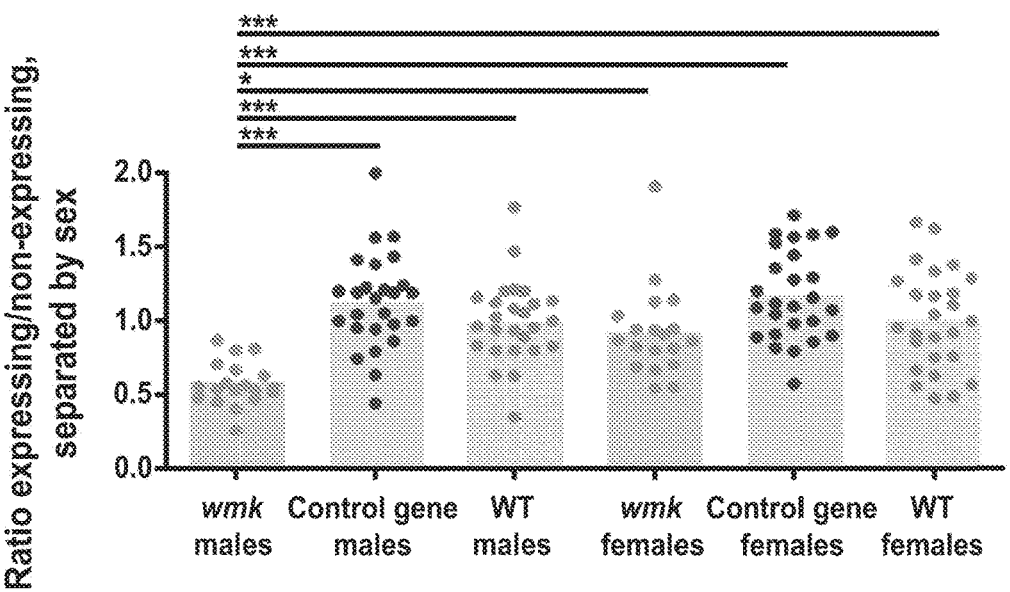

FIG. 5. Act5c and MTD expression of transgenes other than wmk does not cause a sex ratio bias. (a) Sex ratios were quantified for wmk, the control gene (WD0034), WD0625, WD0508, or dual wmk; WD0625 transgenes expressed with the Act5c/CyO driver. Expressing and non-expressing flies of each genotype are siblings. Each point represents the offspring of one vial of 10 mothers and 2 fathers. A biased sex ratio only results when wmk is expressed. Average N per vial is 78. Statistics are based on a Kruskal-Wallis one-way ANOVA followed by Dunn's correction with only the non-expressing flies or only the expressing flies. Groups labeled "a" are significantly different compared to groups labeled "b". Non-expressing flies are non-significant. Bars represent the average sex ratio. E=expressing, NE=non-expressing, Act5c=Act5c gene present, CyO=CyO chromosome present. This experiment has been performed once. (b) Transgenes are expressed in Act5c (E) adult males but not their CyO (NE) brothers as demonstrated by cDNA generated from males. Samples were taken from offspring of parental siblings from the experiment in (a). Samples were from pooled, whole-body, adult extractions of three individuals from each genotype. (c) Transgenes are expressed in Act5c (E) females, but not their CyO (NE) sisters as demonstrated by cDNA generated from females. See (b) for details. Both (b) and (c) have been performed once. (d) Sex ratios were similarly quantified for the listed transgenes using a maternal triple driver (MTD) where expression was driven in the mother throughout oogenesis and offspring were laid with the expressed products loaded into the eggs. Each point represents the offspring of a vial of 10 mothers and 2 fathers. Average N per vial is 74. Statistics are based on a Kruskal-Wallis one-way ANOVA followed by Dunn's correction. Bars represent the average sex ratio. This experiment has been done once. (e) Transgenes are expressed in all adult offspring from the MTD driver as demonstrated by cDNA generated from siblings of mothers from the experiment in (d). Samples are from pooled, dissected ovaries of six flies. This experiment has been performed once. The meanings of notations are as follows: "dual wmk" indicates wmk;0625 co-expressing flies measured with wmk primers, "dual 0625" indicates wmk;0625 co-expressing flies measured FIG. 6. The wmk phenotype is not due to other forms of reproductive parasitism and it does not induce or rescue CI. (a) Sex ratios of infected offspring of the indicated genotypes demonstrate that an infected background does not rescue or alter the Act5c driver-induced phenotype, which would be a characteristic of CI. Each point represents the offspring of a single vial of mothers and fathers. Average N per vial is 105 offspring. The group labeled "a" is significantly different compared to groups labeled "b". Bars represent the average sex ratio. E=expressing, NE=non-expressing, Act5c=has Act5c gene, CyO=has CyO chromosome. (b) Hatch rate of offspring with parents expressing wmk under a nanos driver (expression in the gonads) in either fathers or mothers to test CI induction or rescue, respectively. Expression in males does not recapitulate wild type (WT) CI, and expression in females does not recapitulate rescue. Each dot represents the hatch rate of offspring of a single male and female, N=24-36 crosses per group. Bars indicate average±s. d. (c) Same as (b), but offspring have parents dually expressing wmk; WD0625 under a nanos driver (expression in gonads) in either fathers or mothers to test CI induction or rescue, respectively. Dual expression in males does not recapitulate WT CI, and dual expression in females does not recapitulate rescue CI. (d) Ratio of expressing to non-expressing flies (same flies as FIG. 1) broken down by sex. Each dot represents a comparison of sibling (brothers or sisters) offspring from a single vial of mothers and fathers. Bars represent the average ratio. The wmk male ratio is reduced, but wmk females are not significantly increased compared to controls. This indicates a loss of wmk-expressing males without a corresponding increase in females, suggesting male killing rather than feminization. Statistics for (a) and (d) experiments are based on a Kruskal-Wallis one-way ANOVA followed by Dunn's correction. Statistics for (b) and (c) were performed with a Mann-Whitney test between each of the two groups indicated by the significance bars. These experiments have all been performed once. $*p<0.05$, $p<0.01$, $*p<0.001$. (−), no Wolbachia infection; (+), Wolbachia infection; blue, normal; red, CI cross; purple, rescue cross; orange, wmk cross; green, dual wmk; WD0625.

Figure 1:
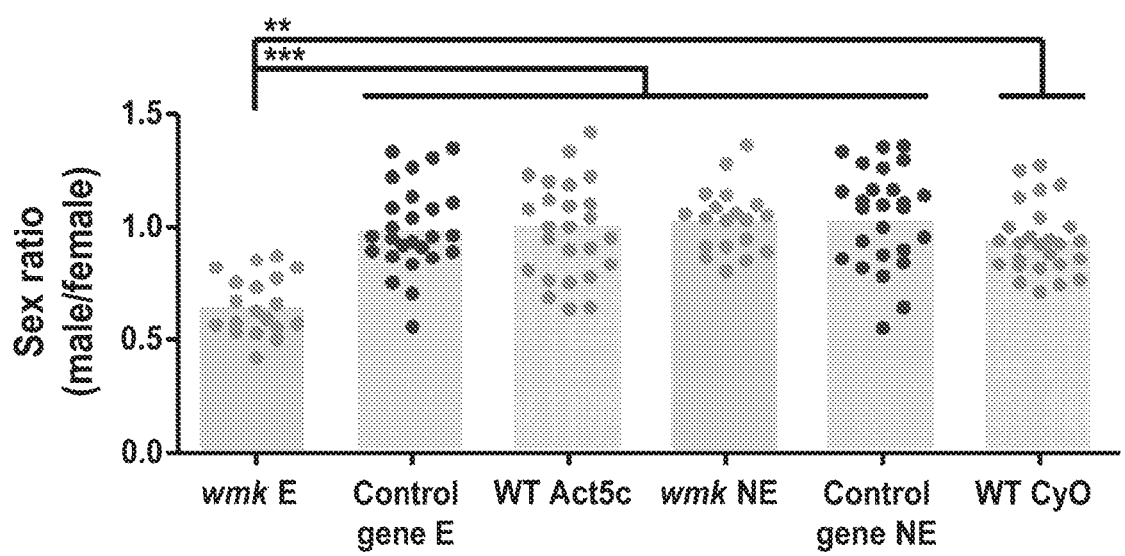
FIG. 1. Transgenic expression of wmk causes a female-biased sex ratio. Each point represents the adult offspring produced by a replicate of ten mothers and two fathers (average offspring N per data point is 90). Bars represent the average sex ratio. Control gene flies have the control *Wol-* bachia transgene, WD0034. WT is the BSC8622 strain. E=expressing, NE=non-expressing, Act5c=has Act5c-Gal4 gene, CyO=has CyO chromosome. wmk-expressing flies have a significantly female-biased sex ratio against all other genotypes. This experiment has been done four times. Statistics are based on a Kruskal-Wallis one-way ANOVA followed by Dunn's correction. p<0.01, *p<0.001. Orange dots represent wmk, blue dots represent the control gene, and gray dots represent the WT strain.
Figure 7:
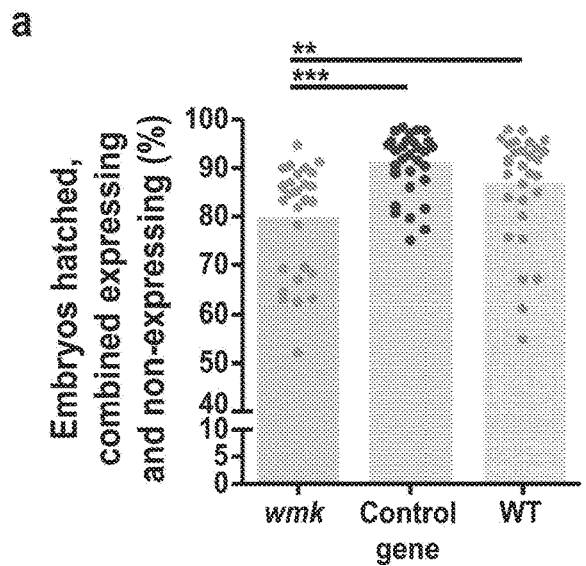
Figure 7:
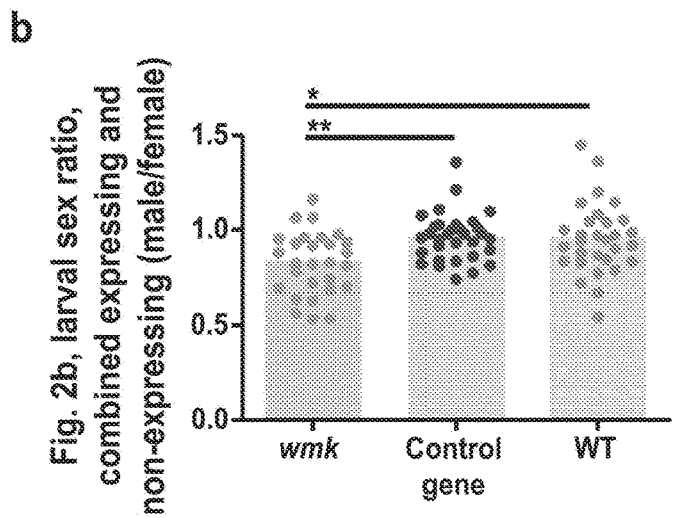

FIG. 7. wmk reduces the embryonic hatch rate and larval sex ratios are female-biased. (a) Each point represents the average embryonic offspring hatch rate from 10 mothers and 2 fathers (average embryonic offspring N per data point is 167). Data points include expressing and non-expressing offspring (see methods). Bars represent the average hatch rate. This experiment has been done once and the sex ratio in FIG. 1 is a measurement of surviving offspring from this hatch rate once they reached adulthood. Orange dots represent wmk, blue dots represent the control gene, and gray dots represent the WT strain. (b) Each point represents the larval offspring sex ratio (expressing and non-expressing combined, see methods) from the hatch rate experiment in (a). Average N is 143 larval offspring per cross of 10 mothers and 2 fathers. Statistics are based on a Krusakal-Wallis one-way ANOVA followed by Dunn's correction. $*p<0.05$, $p<0.01$, $*p<0.001$. This experiment has been done once.

Figure 8:
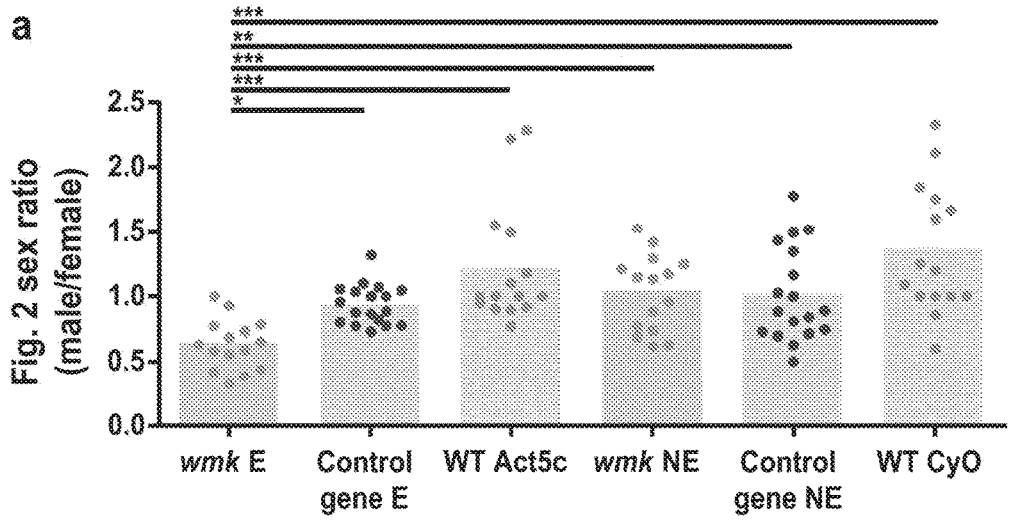
Figure 8:
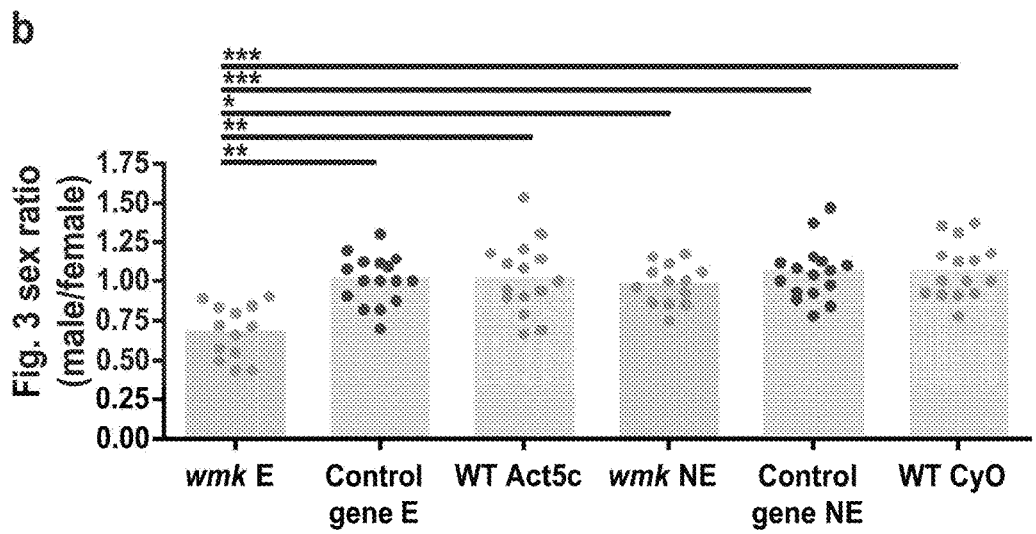

FIG. 8. The corresponding sex ratios of all experiments are female-biased. Alongside the experiments in FIG. 2 and FIG. 3, sex ratios were measured. (a) Graph of the adult offspring sex ratio from the cytology experiment in FIG. 2. Each point represents the offspring of a single vial of mothers and fathers. This was measured with offspring of siblings to the flies used to lay eggs in FIG. 2. Average N is 79 adult offspring per cross of 10 mothers and 2 fathers. Statistics are based on a Kruskal-Wallis one-way ANOVA followed by Dunn's correction. This experiment has been done once. (b) Graph of the adult sex ratio from the experiment in FIG. 3. Each point represents the offspring of a single vial of mothers and fathers. This was measured with offspring of siblings to the flies used to lay eggs in FIG. 3. Average N is 85 adult offspring per vial. Statistics are based on a Kruskal-Wallis one-way ANOVA followed by Dunn's correction. E=expressing, NE=non-expressing, Act5c=has Act5c gene, CyO=has CyO chromosome. $*p<0.05$, $*p<0.01$, $***p<0.001$. This experiment has been done once. All bars represent the average sex ratio.

Figure 9:
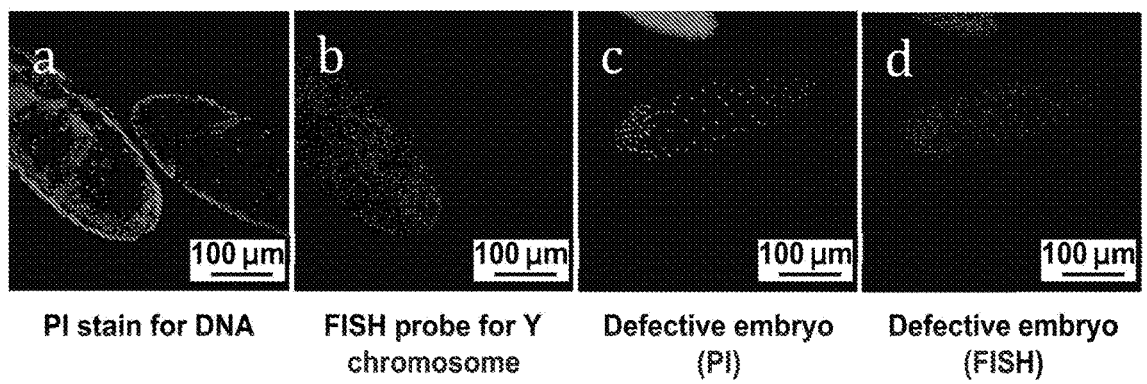

FIG. 9. Representative images of FISH staining of Y chromosome from data in FIG. 3. These images were taken as a part of the experiment described in FIG. 3. (a) Image of two normal control gene embryos approximately 4 h after egg deposition (aed) stained for DNA with PI. (b) Image of the same embryos as (a) stained with a Cy5-conjugated FISH probe specific to the Y chromosome. The left embryo is male, the right embryo is female. (c) Image of a wmk embryo 3-4 h aed stained with PI showing local mitotic failure and chromatin bridging. (d) Image of the same embryo as (c) stained with the Y chromosome probe, showing it is male.

Figure 10:
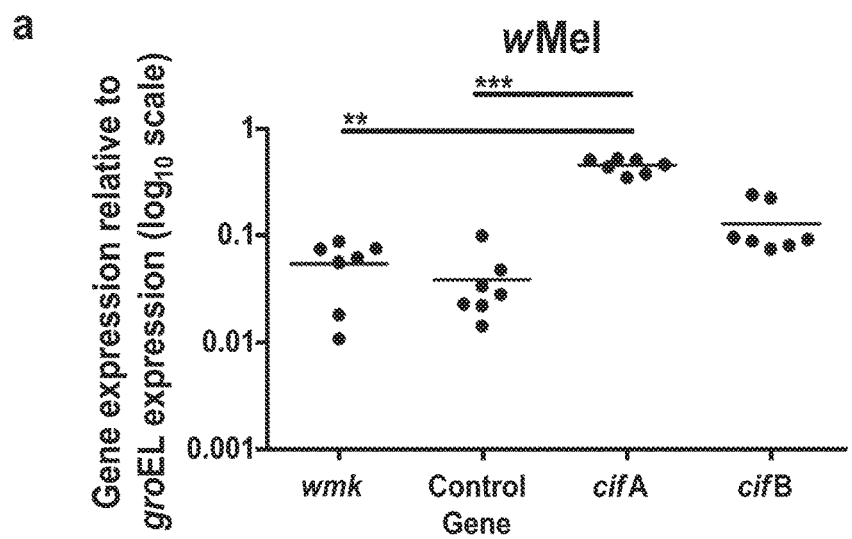
Figure 10:
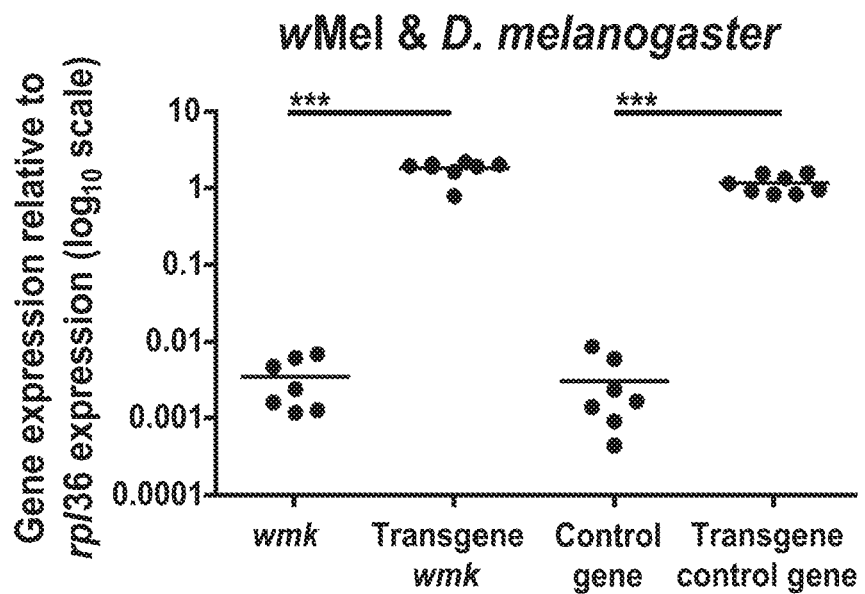
Figure 10:
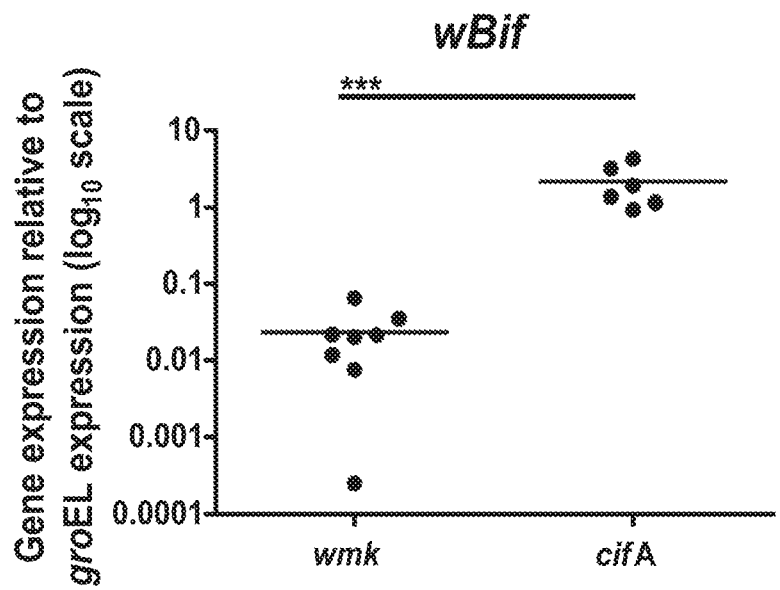

FIG. 10. Native Wolbachia gene and transgene expression in embryos of D. melanogaster and D. bifasciata. (a) Graph of prophage WO or Wolbachia gene expression in wMel-infected D. melanogaster embryos fixed 4-5 h aed (pooled male & female) compared to Wolbachia groEL. Each point (n=7) represents a pool of 30 embryos from a set of 10 mothers and 2 fathers. (b) Graph of (i) transgene expression in uninfected D. melanogaster embryos fixed 4-5 h aed versus (ii) native gene expression in samples from a, both compared to Drosophila rp136. (pooled male, female, expressing, and non-expressing for transgenes). Each point (transgene n=8, native n=7) represents a pool of 30 embryos from a set of 10 mothers and 2 fathers. (c) Graph of wBif Wolbachia gene expression in D. bifasciata embryos 4-5 h aed (pooled male & female) compared to Wolbachia groEL. Each point (n=6 or 8) represents a pool of 30 embryos from a set of 10 mothers and 2 fathers. Values denote $2^{-\Delta Ct}$. Statistics are based on a Kruskal-Wallis one-way ANOVA followed by Dunn's correction. This experiment has been done once. $p<0.01$, $*p<0.001$.

Figure 11:
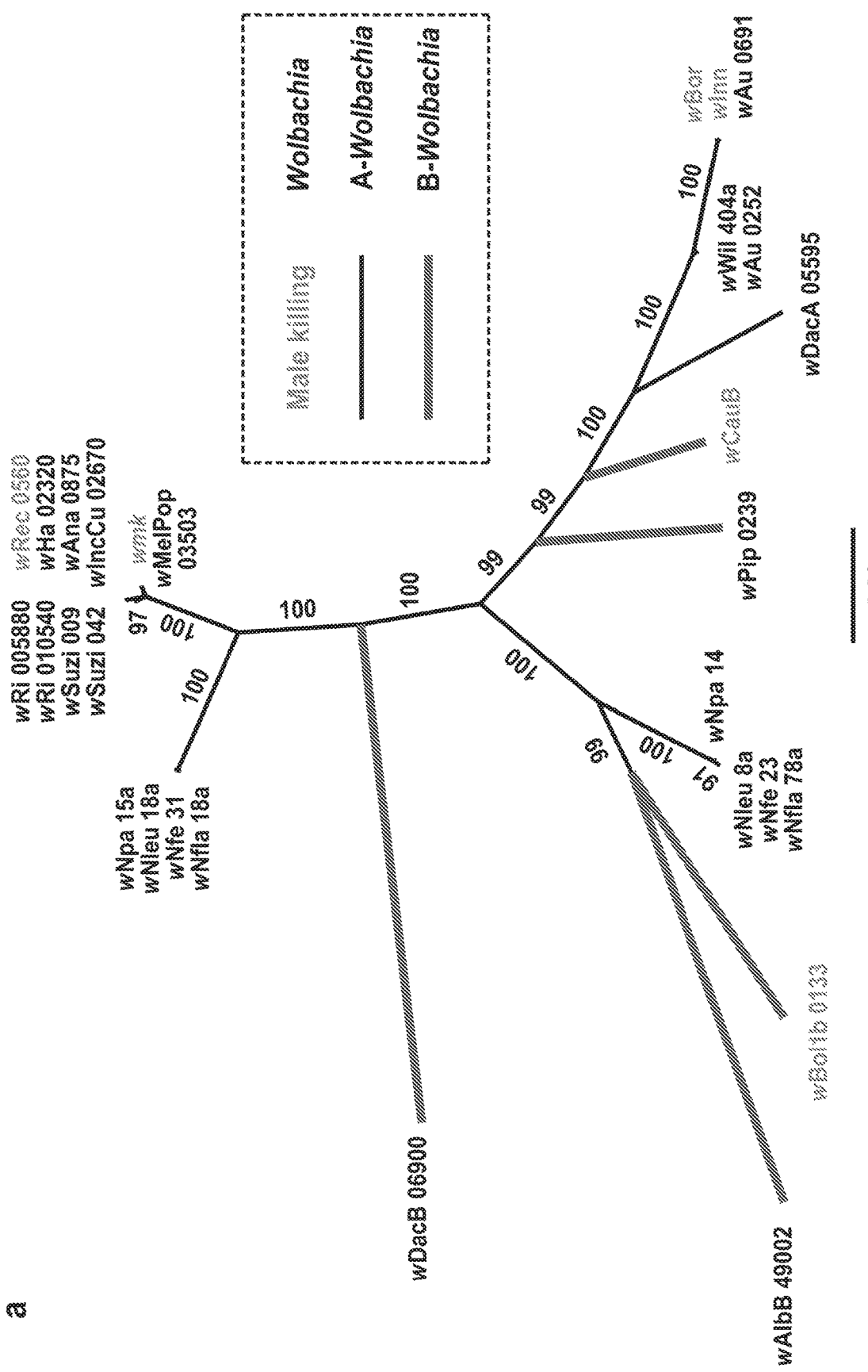
Figure 11:
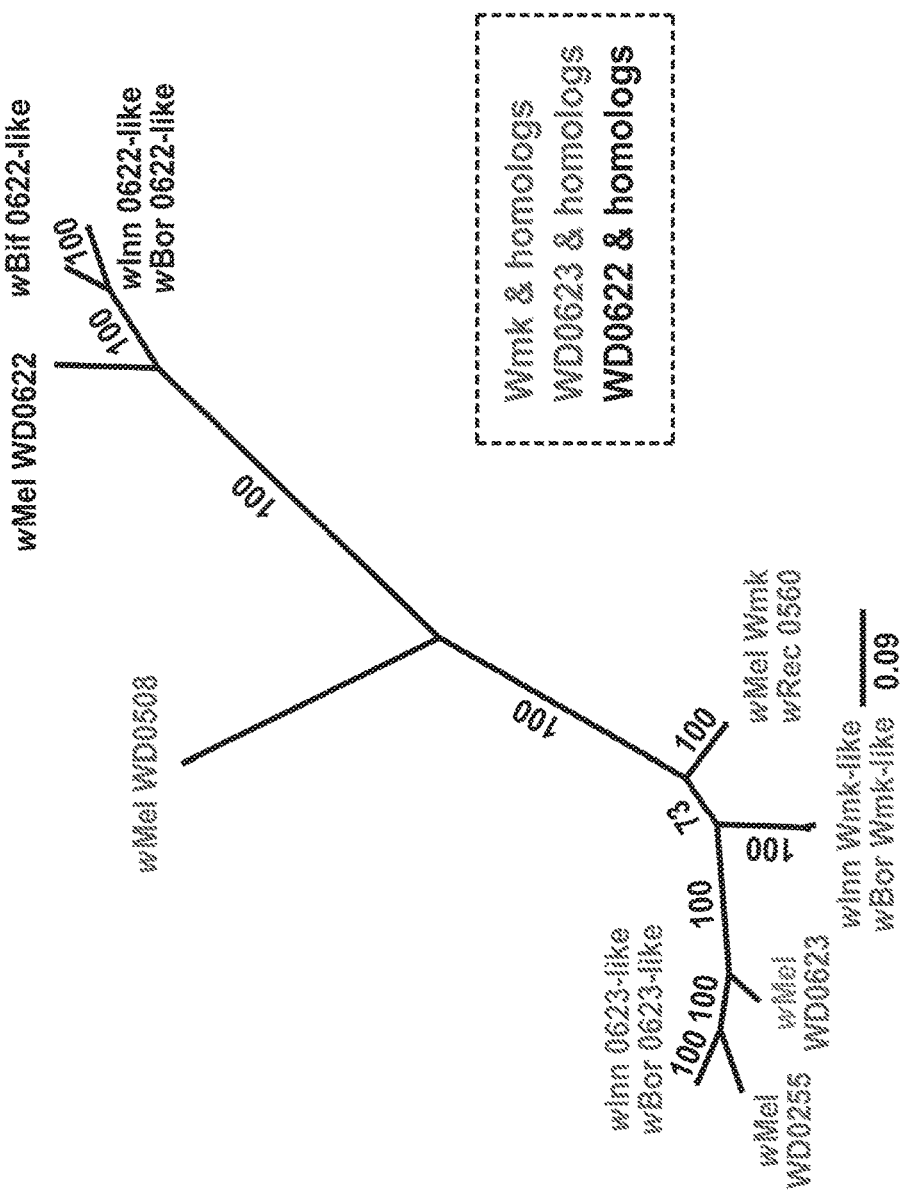

FIG. 11. Comparative genomics of the wmk gene and protein. (a) Phylogeny of full-length wmk gene, based on an 893-bp alignment and GTR+I+G model of evolution. Full-length wmk homologs are widespread throughout prophage WO-containing Wolbachia strains, some of which are male-killing strains. Like many WO-associated genes, including CI factors cifA and cif/B, the wmk phylogeny does not support evolution with the Wolbachia chromosome because homologs in A- and B-Wolbachia do not cluster according to supergroup. Wolbachia supergroups are illustrated as either black (A-Wolbachia) or red (B-Wolbachia) branches. wmk (WD0626) and homologs from male-killing strains are highlighted in cyan. Consensus support values are shown on the branches. The tree includes all taxa that are reciprocal best hits of wMel wmk. See Table 2A and 2B for accession numbers and BLASTn E-values. (b) A Bayesian phylogeny of Wmk protein and homologous peptides from wMel and sequenced male-killing strains in Drosophila, based on a 168 aa-alignment using the JTT+G model of evolution. It shows that homologs in these taxa cluster according to gene synteny within prophage WO genomes (see FIG. 1). Consensus support values are shown on the branches. Colors correspond to FIG. 4. Accession numbers and BLASTp E-values are provided in Table 2A and 2B.

Figure 12:
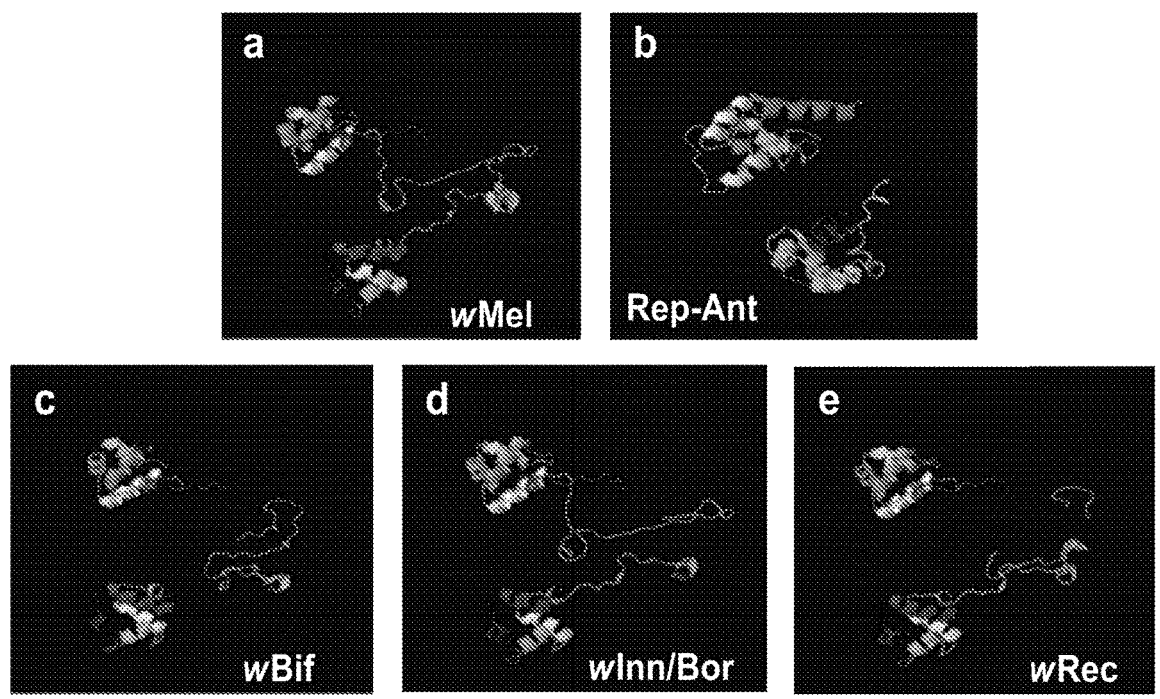

FIG. 12. Protein architecture of Wmk and homology to a phage repressor. (a) Image of the most likely 3D structure of Wmk from wMel determined by the Phyre2 web portal. 66% of residues modeled at >90% confidence. The image is colored in order of the rainbow from N terminus (red) to C terminus (blue). (b) The globular structure is most similar to a known phage DNA-binding transcriptional repressor, namely the Rep-Ant complex from *Salmonella*-temperate phage, modeled here. Other top results were also transcriptional regulators and DNA-binding proteins. The Rep-Ant complex is comprised of two separate, dimerized peptides, and does not include the linker region of Wmk shown in green in (a). The image is colored in order of the rainbow from N terminus (red) to C terminus (blue). (c) Representation of alignment confidence of the Rep-Ant complex to Wink, in the same orientation as (b). It is colored in the order of the rainbow from high alignment confidence (red) to low confidence (purple). The overall confidence is 99.84% with 19% identity and 166 aligned residues across residues 1-258 of Wink (84% coverage). Alignment confidence values are obtained from the posterior probabilities calculated in the Forward-Backward algorithm. (d) Image of the most likely 3D structure of the wBif Wmk homolog. 61% of residues modeled at 99.7% confidence. This image is colored in order of the rainbow from N terminus (red) to C terminus (blue). (e) The wBif Wink homolog structure is most similar to a putative *C. difficile* DNA-binding protein. Other top hits include transcriptional regulators and phage repressors. The image is colored in order of the rainbow from N terminus (red) to C terminus (blue). (f) Representation of alignment confidence of the *C. difficile* DNA-binding protein to the wBif Wink homolog, in the same orientation as (e). It is colored in the order of the rainbow from high alignment confidence (red) to low confidence (purple). The overall confidence is 99.73% with 11% identity and 106 aligned residues across residues 41-146 of the wBif Wmk homolog (60% coverage). Alignment confidence values are obtained using the same algorithm as (c).

Figure 13:
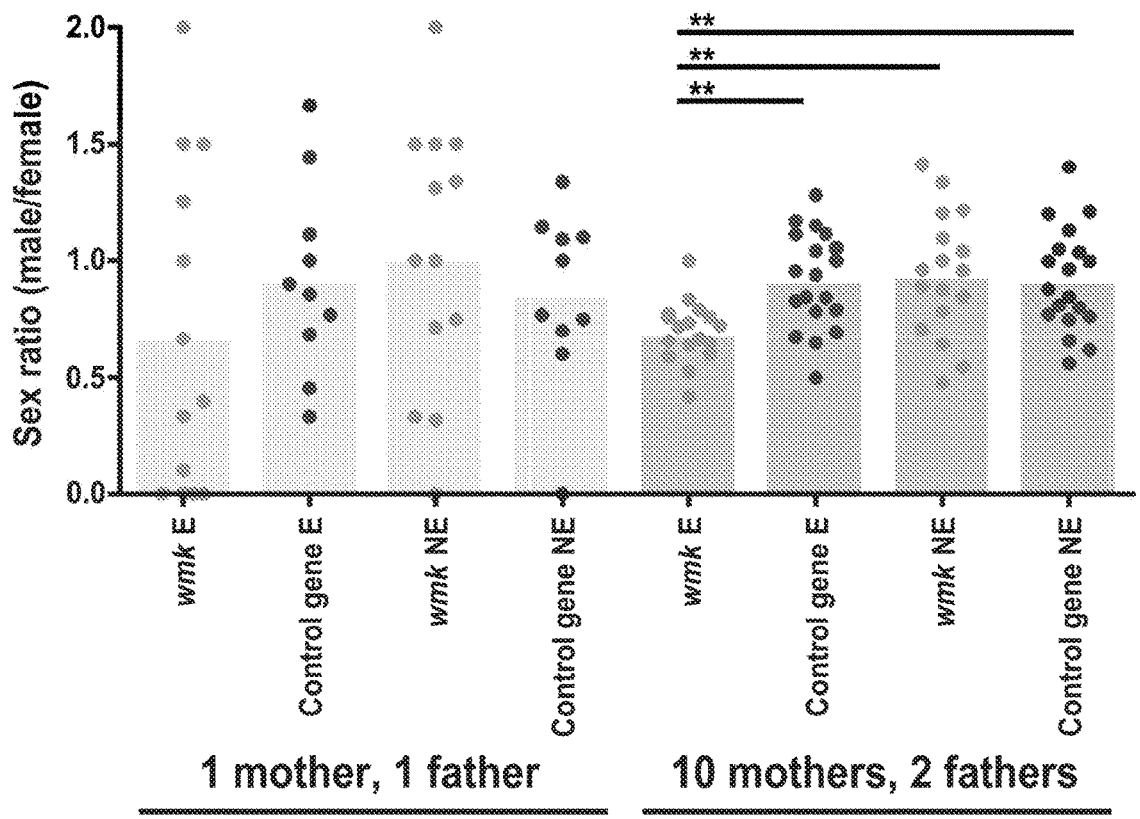

FIG. 13. An experimental setup of 10 females crossed to 2 males yields less sex ratio variance in data than individual pairings. Based on this, the setup of 10 females crossed to 2 males is used throughout the paper. Vials were set up with either one female and one male or ten females and two males. Flies laid eggs for 36 h. Each point represents the adult offspring sex ratio from a single mother and father (4 leftmost lighter bars) or a set of ten mothers and two fathers (4 rightmost darker bars). Average offspring N per vial is 20 for individual pairings and 93 for group crosses. Statistics are based on a Kruskal-Wallis one-way ANOVA followed by Dunn's correction comparing either the single pairings (ns) or only the group crossings (**$p<0.01$). Bars represent the average sex ratio. E=expressing, NE=non-expressing. This experiment has been performed once.

Figure 14:
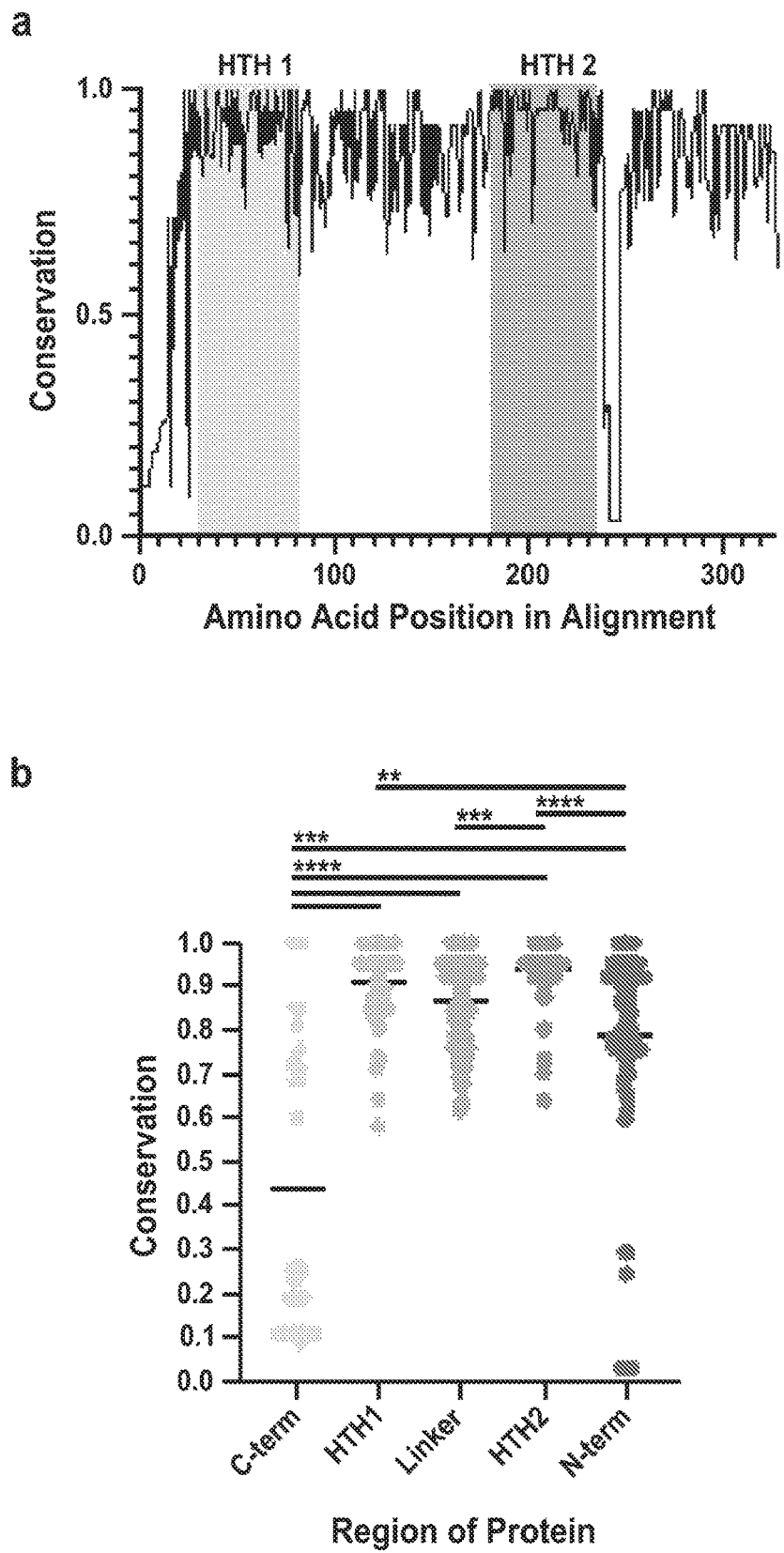

FIG. 14. Wmk amino acid identity is more conserved in the DNA-binding domains than certain other regions of the protein. (a) Level of amino acid conservation is shown across the length of the amino acid alignment of 31 Wmk homologs. The homologs used in the analysis include all those shown in FIG. 11 with the addition of the wBif homolog. A score of 1 indicates complete conservation across homologs while a score of 0 indicates all homologs have different amino acid identities in that location. The two HTH DNA-binding domains are highlighted in shades of orange for reference. (b) Amino acid conservation from the same set of data as (a) is shown in a different format here, where each dot represents the conservation of a particular amino acid position within a designated region of the protein. Statistics are based on a Kruskal-Wallis one-way ANOVA followed by Dunn's correction. Bars indicate mean values. $p<0.01$, *$p<0.001$, ****$p<0.0001$.

DETAILED DESCRIPTION

Disclosed herein are genetically modified arthropods and genetically modified bacteria useful for controlling and/or reducing populations of arthropods (for example, insects). Further disclosed herein are genetically modified bacteria, genetically modified phage, and/or genetically modified prophage for controlling and/or reducing populations of arthropods (for example, insects). Also disclosed herein is an arthropod transinfected with a male-killing microbe, phage or bacteria that naturally infects another host. The inventors have identified a gene, hereafter denoted WO male killing (wmk) (or locus WD0626 in the wMel *Wolbachia* genome), that causes male lethality when transgenically expressed, which leads to a female-biased sex ratio. These male arthropod-killing genes encoding male arthropod killing factors are used to genetically modify arthropods in order to reduce a population of target arthropods. In addition, the methods of using these male arthropod killing factors can be combined with additional methods for vector control, such as sterile insect techniques or incompatible insect techniques.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs. The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed. As used in this disclosure and in the appended claims, the singular forms "a", "an", "the", include plural referents unless the context clearly dictates otherwise.

The following definitions are provided for the full understanding of terms used in this specification.

Terminology

The term "nucleic acid" as used herein means a polymer composed of nucleotides, e.g. deoxyribonucleotides or ribonucleotides.

The terms "ribonucleic acid" and "RNA" as used herein mean a polymer composed of ribonucleotides.

The terms "deoxyribonucleic acid" and "DNA" as used herein mean a polymer composed of deoxyribonucleotides.

The term "oligonucleotide" denotes single- or double-stranded nucleotide multimers of from about 2 to up to about 100 nucleotides in length. Suitable oligonucleotides may be prepared by the phosphoramidite method described by Beaucage and Carruthers, *Tetrahedron Lett.*, 22:1859-1862 (1981), or by the triester method according to Matteucci, et al., *J. Am. Chem. Soc.*, 103:3185 (1981), both incorporated herein by reference, or by other chemical methods using either a commercial automated oligonucleotide synthesizer or VLSIPS™ technology. When oligonucleotides are referred to as "double-stranded," it is understood by those of skill in the art that a pair of oligonucleotides exist in a hydrogen-bonded, helical array typically associated with, for example, DNA. In addition to the 100% complementary form of double-stranded oligonucleotides, the term "double-stranded," as used herein is also meant to refer to those forms which include such structural features as bulges and loops, described more fully in such biochemistry texts as Stryer, *Biochemistry*, Third Ed., (1988), incorporated herein by reference for all purposes.

The term "polynucleotide" refers to a single or double stranded polymer composed of nucleotide monomers. In some embodiments, the polynucleotide is composed of nucleotide monomers of generally greater than 100 nucleotides in length and up to about 8,000 or more nucleotides in length.

The term "polypeptide" refers to a compound made up of a single chain of D- or L-amino acids or a mixture of D- and L-amino acids joined by peptide bonds.

The term "complementary" refers to the topological compatibility or matching together of interacting surfaces of a probe molecule and its target. Thus, the target and its probe can be described as complementary, and furthermore, the contact surface characteristics are complementary to each other.

The term "hybridization" refers to a process of establishing a non-covalent, sequence-specific interaction between two or more complementary strands of nucleic acids into a single hybrid, which in the case of two strands is referred to as a duplex.

The term "anneal" refers to the process by which a single-stranded nucleic acid sequence pairs by hydrogen bonds to a complementary sequence, forming a double-stranded nucleic acid sequence, including the reformation (renaturation) of complementary strands that were separated by heat (thermally denatured).

The term "melting" refers to the denaturation of a double-stranded nucleic acid sequence due to high temperatures, resulting in the separation of the double strand into two single strands by breaking the hydrogen bonds between the strands.

The term "promoter" or "regulatory element" refers to a region or sequence determinants located upstream or downstream from the start of transcription and which are involved in recognition and binding of RNA polymerase and other proteins to initiate transcription. Promoters need not be of bacterial origin, for example, promoters derived from viruses or from other organisms can be used in the compositions, systems, or methods described herein.

A polynucleotide sequence is "heterologous" to a second polynucleotide sequence if it originates from a foreign species, or, if from the same species, is modified by human action from its original form. For example, a promoter operably linked to a heterologous coding sequence refers to a coding sequence from a species different from that from which the promoter was derived, or, if from the same species, a coding sequence which is different from naturally occurring allelic variants.

The term "recombinant" refers to a human manipulated nucleic acid (e.g. polynucleotide) or a copy or complement of a human manipulated nucleic acid (e.g. polynucleotide), or if in reference to a protein (i.e, a "recombinant protein"), a protein encoded by a recombinant nucleic acid (e.g. polynucleotide). In embodiments, a recombinant expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In another example, a recombinant expression cassette may comprise nucleic acids (e.g. polynucleotides) combined in such a way that the nucleic acids (e.g. polynucleotides) are extremely unlikely to be found in nature. For instance, human manipulated restriction sites or plasmid vector sequences may flank or separate the promoter from the second nucleic acid (e.g. polynucleotide). One of skill will recognize that nucleic acids (e.g. polynucleotides) can be manipulated in many ways and are not limited to the examples above.

The term "expression cassette" refers to a nucleic acid construct, which when introduced into a host cell, results in transcription and/or translation of a RNA or polypeptide, respectively. In embodiments, an expression cassette comprising a promoter operably linked to a second nucleic acid (e.g. polynucleotide) may include a promoter that is heterologous to the second nucleic acid (e.g. polynucleotide) as the result of human manipulation (e.g., by methods described in Sambrook et al., *Molecular Cloning—A Laboratory Manual*, Cold Spring Harbor Laboratory, Cold Spring Harbor, N.Y., (1989) or Current Protocols in Molecular Biology Volumes 1-3, John Wiley & Sons, Inc. (1994-1998)). In some embodiments, an expression cassette comprising a terminator (or termination sequence) operably linked to a second nucleic acid (e.g. polynucleotide) may include a terminator that is heterologous to the second nucleic acid (e.g. polynucleotide) as the result of human manipulation. In some embodiments, the expression cassette comprises a promoter operably linked to a second nucleic acid (e.g. polynucleotide) and a terminator operably linked to the second nucleic acid (e.g. polynucleotide) as the result of human manipulation. In some embodiments, the expression cassette comprises an endogenous promoter. In some embodiments, the expression cassette comprises an endogenous terminator. In some embodiments, the expression cassette comprises a synthetic (or non-natural) promoter. In some embodiments, the expression cassette comprises a synthetic (or non-natural) terminator.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

The phrase "codon optimized" as it refers to genes or coding regions of nucleic acid molecules for the transformation of various hosts, refers to the alteration of codons in the gene or coding regions of polynucleic acid molecules to reflect the typical codon usage of a selected organism without altering the polypeptide encoded by the DNA. Such optimization includes replacing at least one, or more than one, or a significant number, of codons with one or more codons that are more frequently used in the genes of that selected organism. For example, the sequence of a heterologous gene expressed in *Wolbachia* may be "codon optimized" to optimize gene expression based on the preferred codon usage in *Wolbachia*.

Nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are near each other, and, in the case of a secretory leader, contiguous and in reading phase. However, operably linked nucleic acids (e.g. enhancers and coding sequences) do not have to be contiguous. Linking is accomplished by ligation at convenient restriction sites. If such sites do not exist, the synthetic oligonucleotide adaptors or linkers are used in accordance with conventional practice. In embodiments, a promoter is operably linked with a coding sequence when it is capable of affecting (e.g. modulating relative to the absence of the promoter) the expression of a protein from that coding sequence (i.e., the coding sequence is under the transcriptional control of the promoter).

"Transformation" refers to the transfer of a nucleic acid molecule into a new carrier (e.g. *Wolbachia* cell or phage or prophage). In embodiments, the nucleic acid molecule may be a plasmid that replicates autonomously or it may integrate into the genome of the host organism. Host organisms containing the transformed nucleic acid molecule may be referred to as "transgenic" or "recombinant" or "transformed" organisms. A "genetically modified" organism (e.g. genetically modified arthropod) is an organism that includes a nucleic acid that has been modified by human intervention. Examples of a nucleic acid that has been modified by human intervention include, but are not limited to, insertions, deletions, mutations, expression nucleic acid constructs (e.g. over-expression or expression from a non-natural promoter or control sequence or an operably linked promoter and gene nucleic acid distinct from a naturally occurring promoter and gene nucleic acid in an organism), extra-chromosomal nucleic acids, and genomically contained modified nucleic acids.

"Transinfection" as used herein refers to extracting a microbe (either a pure extraction or mixed with other organisms or substances) from its natural host and then infecting an unnatural host with the extract. The recipient organism is then transinfected with a foreign microbe.

The term "male arthropod killing factor" or "male killing gene" refers to a gene or a factor encoded by the gene from bacteria which provide a function that is required and/or beneficial to produce the phenotype of male killing used by various, unrelated bacterial infections (e.g., *Wolbachia*).

The term "variant" or "derivative" as used herein refers to an amino acid sequence derived from the amino acid sequence of the parent protein having one or more amino acid substitutions, insertions, and/or deletions. For example, a "male arthropod killing factor variant" includes a male arthropod killing factor that may have a number of amino acid changes. In some embodiments, the variants may be greater than about 20%, greater than about 30%, greater than about 40%, greater than about 50%, greater than about 60%, greater than about 70%, greater than about 80%, greater than about 90%, or greater than about 95%, identical to the parent nucleic acid sequence or amino acid sequence.

The term "about" as used herein when referring to a measurable value such as an amount, a percentage, and the like, is meant to encompass variations of ±20%, ±10%, ±5%, or ±1% from the measurable value.

Male Arthropod Killing Factors and Methods of Use

In some aspects, disclosed herein is a genetically modified arthropod, said arthropod comprising:
 a gene encoding a male arthropod killing factor; and
 a promoter operably linked to the gene encoding the male arthropod killing factor;
 wherein the expression of the gene encoding the male arthropod killing factor in arthropod embryos causes a reduction in viable surviving male offspring in comparison to arthropod embryos not expressing the gene encoding the male arthropod killing factor.

In some embodiments, the gene encoding the male arthropod killing factor is from a bacterium. In some embodiments, the gene encoding the male arthropod killing factor is from a phage or prophage. In some embodiments, the gene encoding the male arthropod killing factor is from *Wolbachia* (or prophage WO or phage WO). In some embodiments, the male arthropod killing factor is wmk (WD0626) or its homologs. In some embodiments, the male arthropod killing factor comprises the amino acid sequence SEQ ID NO:1, or a variant thereof.

In some embodiments, the reduction in viable male offspring is greater than 10% (for example at least 10%, at least 20%, at least 30%, at least 40%, at least 50%, at least 60%, at least 70%, at least 80%, at least 90%, at least 100%).

In some embodiments, the arthropod is an insect. In some embodiments, the insect is selected from the genera consisting of *Aedes, Culex* and *Anopheles*. In some embodiments, the insect is selected from the group consisting of *Aedes albopictus, Aedes aegypti* and *Aedes polynesiensis*. In some embodiments, the insect is *Drosophila suzukii*.

In some aspects, disclosed herein is a method for controlling a population of target arthropods, comprising:
 providing a gene encoding a male arthropod killing factor, and a promoter operably linked to the gene encoding the male arthropod killing factor;
 transforming a population of arthropods with the gene encoding the male arthropod killing factor and the promoter operably linked to the gene encoding the male arthropod-killing factor; and
 releasing the population of arthropods amongst a population of target arthropods, wherein the release of the arthropods reduces the population of target arthropods.

In some aspects, disclosed herein is a method for controlling a population of target arthropods, comprising:
 providing a gene encoding a male arthropod killing factor, and a promoter operably linked to the gene encoding the male arthropod killing factor;
 genetically transforming a bacteria, phage, or prophage with the gene encoding the male arthropod killing factor operably linked to the promoter;
 transinfecting a population of arthropods with the bacteria, phage, or prophage; and
 releasing the population of arthropods amongst a population of target arthropods, wherein the release of the arthropods reduces the population of target arthropods.

In some embodiments, the gene encoding the male arthropod killing factor is from a bacterium. In some embodiments, the gene encoding the male arthropod killing factor is from a phage or prophage. In some embodiments, the gene encoding the male arthropod killing factor is from *Wolbachia* (or prophage WO or phage WO). In some embodiments, the male arthropod killing factor is wmk (WD0626) or its homologs. In some embodiments, the male arthropod killing factor comprises the amino acid sequence SEQ ID NO:1, or a variant thereof. In some embodiments, the reduction in viable male offspring is greater than 10% (for example at least 10%, at least 20%, at least 30%, at least 40%, at least 50%, at least 60%, at least 70%, at least 80%, at least 90%, at least 100%, or more).

In some embodiments, the arthropod is an insect. In some embodiments, the insect is selected from the genera consisting of *Aedes, Culex* and *Anopheles*. In some embodiments, the insect is selected from the group consisting of *Aedes albopictus, Aedes aegypti* and *Aedes polynesiensis*. In some embodiments, the insect is *Drosophila suzukii*.

In some embodiments, the method further comprises providing an additional method of arthropod control. In some embodiments, the additional method of arthropod control is a sterile insect technique (SIT). In some embodiments, the additional method of arthropod control is an incompatible insect technique (IIT).

In some embodiments, disclosed herein is a genetically modified arthropod, said arthropod comprising: a gene encoding a male arthropod killing factor (or with cofactors) or a variant thereof. In some embodiments, the gene encoding the male arthropod killing factor is a heterologous gene.

In some embodiments, the male arthropod killing factor is wmk (WD0626). In some embodiments, the male arthropod killing factor is a homolog of wmk (WD0626). In some embodiments, the male arthropod killing factor is selected from the sequences disclosed in Table 1. In some embodiments, the gene encoding the male arthropod killing factor is selected from the sequences disclosed in Table 2A and 2B. For example, the male arthropod killing factor can be selected from the group consisting of wRec 0560, wInn homolog of WD0626, wBor homolog of WD0626, wMel WD0255, wMel WD0623, wInn homolog of WD0623, wBor homolog of WD0623, wMel WD0508, wMel WD0622, wInn homolog of WD0622, wBor homolog of WD0622, and wBif homolog of WD0622. In some embodiments, the male arthropod killing factor can be selected from the accession numbers WP_010962718.1, WP_038198911.1, WP_010962465.1, WP_010962717.1, WP_010962645.1, or WP_010962716.1.

In some embodiments, the wmk homolog fulfills at least one of the following: 1) sequence similarity of 40% or more to wmk; 2) genes with one or more HTH domain(s) in phage WO gene regions; and/or 3) HTH-containing genes present in the same phage gene region as any cif/cid/cin (genes WD0631 and WD0632 in strain wMel) homologs.

In some embodiments, the male arthropod killing factor comprises the amino acid sequence SEQ ID NO:1. In some embodiments, the male arthropod killing factor comprises the amino acid sequence SEQ ID NO:1, or a variant thereof.

In some embodiments, the gene encoding the male arthropod killing factor comprises the amino acid sequence encoded by the nucleic acid sequence SEQ ID NO:2. In some embodiments, the gene encoding the male arthropod killing factor comprises the amino acid sequence encoded by the nucleic acid sequence SEQ ID NO:2, or a variant thereof.

In some embodiments, the gene encoding the male arthropod killing factor sequence has been codon optimized.

In some embodiments, the male arthropod killing factor comprises an amino acid sequence that is at least 30% identical (for example, at least 30%, at least 40%, at least 50%, at least 60%, at least 70%, at least 80%, at least 90%, at least 95%, at least 99%) to the amino acid sequence SEQ ID NO:1.

In some embodiments, the gene encoding the male arthropod killing factor comprises a sequence that is at least 30% identical (for example, at least 30%, at least 40%, at least 50%, at least 60%, at least 70%, at least 80%, at least 90%, at least 95%, at least 99%) to the amino acid sequence encoded by the nucleic acid sequence SEQ ID NO:2.

In some embodiments, the male arthropod killing factor comprises an amino acid sequence that is at least 20% identical to the amino acid sequence SEQ ID NO:1. In some embodiments, the gene encoding the male arthropod killing factor comprises a sequence that is at least 20% identical to the amino acid sequence encoded by the nucleic acid sequence SEQ ID NO:2.

In some embodiments, the male arthropod killing factor comprises the amino acid sequence SEQ ID NO:1, or a fragment thereof. In some embodiments, the male arthropod killing factor comprises an amino acid sequence encoded by the nucleic acid sequence SEQ ID NO:2, or a fragment thereof.

In some embodiments, the male arthropod killing factor comprises an amino acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 1.

In some embodiments, the male arthropod killing factor comprises an amino acid sequence encoded by a nucleic acid sequence at least 60% (for example, at least 60%, at least 65%, at least 70%, at least 75%, at least 80%, at least 85%, at least 90%, at least 95%, at least 96%, at least 97%, at least 98%, at least 99%) identical to SEQ ID NO: 2.

In some embodiments, the male arthropod killing factor comprises a wmk homolog listed in Table 1, or a variant or fragment thereof. In some embodiments, the male arthropod killing factor comprises a sequence at least 60% (for example, at least 60%, at least 65%, at least 70%, at least 75%, at least 80%, at least 85%, at least 90%, at least 95%, at least 96%, at least 97%, at least 98%, at least 99%) identical to a wmk homolog listed in Table 1, or a variant or fragment thereof.

In some embodiments, the male arthropod killing factor comprises a wmk homolog listed in Table 2A, or a variant or fragment thereof. In some embodiments, the male arthropod killing factor comprises a sequence at least 60% (for example, at least 60%, at least 65%, at least 70%, at least 75%, at least 80%, at least 85%, at least 90%, at least 95%, at least 96%, at least 97%, at least 98%, at least 99%) identical to a wmk homolog listed in Table 2A, or a variant or fragment thereof.

In some embodiments, the male arthropod killing factor comprises a wmk homolog listed in Table 2B, or a variant or fragment thereof. In some embodiments, the male arthropod killing factor comprises a sequence at least 60% (for example, at least 60%, at least 65%, at least 70%, at least 75%, at least 80%, at least 85%, at least 90%, at least 95%, at least 96%, at least 97%, at least 98%, at least 99%) identical to a wmk homolog listed in Table 2B, or a variant or fragment thereof.

In some embodiments, the male arthropod killing factor comprises a wmk homolog listed in Table 3, or a variant or fragment thereof. In some embodiments, the male arthropod killing factor comprises a sequence at least 60% (for example, at least 60%, at least 65%, at least 70%, at least 75%, at least 80%, at least 85%, at least 90%, at least 95%, at least 96%, at least 97%, at least 98%, at least 99%) identical to a wmk homolog listed in Table 3, or a variant or fragment thereof.

In some embodiments, the male arthropod killing factor comprises a wmk homolog listed in Table 6, or a variant or fragment thereof. In some embodiments, the male arthropod killing factor comprises a sequence at least 60% (for example, at least 60%, at least 65%, at least 70%, at least 75%, at least 80%, at least 85%, at least 90%, at least 95%, at least 96%, at least 97%, at least 98%, at least 99%) identical to a wmk homolog listed in Table 6, or a variant or fragment thereof.

In some aspects, disclosed herein is a genetically modified arthropod, said arthropod comprising: a gene encoding a male arthropod killing factor (or a variant thereof); and a promoter operably linked to the gene encoding a male arthropod killing factor or a variant thereof. In some embodiments, the promoter is heterologous. In some embodiments, the promoter is an arthropod promoter. In some embodiments, the gene encoding the male arthropod killing factor is inserted at an endogenous promoter in the arthropod. In some embodiments, the gene encoding the male arthropod killing factor is inserted at a heterologous promoter in the arthropod.

In some aspects, disclosed herein is a genetically modified bacterium comprising:
- a gene encoding a male arthropod killing factor or a variant thereof; and
- a promoter operably linked to the gene encoding a male arthropod killing factor;
- wherein the gene occurs at a non-naturally occurring genomic location in the bacterium.

In some aspects, disclosed herein is an arthropod infected with a bacterium, wherein the bacterium comprises:
- a gene encoding a male arthropod killing factor; and
- a promoter operably linked to the gene encoding the male arthropod killing factor;
- wherein the gene encoding the male arthropod killing factor occurs at a non-naturally occurring genomic location in the bacterium.

In other aspects, disclosed herein is a method for controlling a population of target arthropods, comprising:
providing a genetically modified bacterium comprising:
a gene encoding a male arthropod killing factor, and a promoter operably linked to the gene encoding the male arthropod killing factor;
infecting a population of replacement arthropods with the genetically modified bacterium; and releasing the replacement arthropods amongst a population of target arthropods, wherein the release of the replacement arthropods reduces the population of target arthropods.

In some embodiments, the gene encoding the male arthropod killing factor in arthropod embryos causes a reduction in viable surviving adult male offspring in comparison to arthropod embryos not expressing the gene encoding the male arthropod killing factor.

In addition to genetically bacteria, the methods herein can also use genetically modified phage or prophage. The genetically modified bacteria, phage, or prophage can be transinfected into a new host (a non-natural host). The genetically modified hosts can use any number of promoters known in the art to drive gene expression. The genetically modified hosts can comprise the WD0626 gene, or homologs thereof, or can also include additional male killing genes or cofactors in combination with the WD0626 gene. The genetically modified hosts can comprise multiple copies of the WD0626 gene, or multiple copies of homologs thereof, or any combinations thereof. In addition, as disclosed herein, the various methods of controlling arthropods can be used individually or can be used in various combinations to employ multiple methods in succession, or simultaneously, in methods of controlling a population of target arthropods.

Further disclosed herein are genetically modified bacteria, genetically modified phage, and/or genetically modified prophage for controlling and/or reducing populations of arthropods. Also disclosed herein is an arthropod transinfected with a male-killing microbe, phage or bacteria that naturally infects another host.

Methods in Combination with the Sterile Insect Technique (SIT) and/or an Incompatible Insect Technique (IIT)

In some embodiments, the male arthropod killing factors and methods of use disclosed herein can be used in combination with an additional arthropod (for example, mosquito) control technique. In some embodiments, the additional arthropod control technique is selected from a sterile insect technique (SIT) or an incompatible insect technique (IIT).

In some embodiments, the male arthropod killing factors and methods of use disclosed herein can be used in combination with a Sterile Insect Technique (SIT). The concept of the sterile insect technique (SIT) was first discovered by Knipling in 1955 (Knipling, E. F. *J Econ Entomol* 48, 459-462 (1955)). SIT is the use of sterile males to suppress populations of insects. SIT works by periodic controlled releases of vast numbers of sterile male insects into wild populations. In principle, these sterile males outnumber and outcompete wild males for matings with wild females. If a female mates with a sterile male she will lay eggs that do not hatch. If the proportion of sterile males consistently exceeds the proportion of fertile males then each new generation's reproduction is suppressed. As the wild population numbers dwindle, SIT becomes more and more effective creating a negative feedback loop that ultimately eradicates the species in an area. One major advantage of SIT population suppression versus traditional insecticide treatment is that it is species specific and environmentally safe. Three major processes are necessary for the implementation of SIT: 1) a method of sterilization; 2) a method of sex separation; and 3) a method of dispersal.

The historical example of SIT is Knipling's and the USDA's rearing of irradiated sterile males to eradicate the New World Screwworm (*Cochliomya hominivorax*) in North America and Mexico (Bushland, R. C., et al. *Science* 122, 287-288 (1955)). Screwworm is a deadly livestock pest which causes myiasis (an infestation of parasitic fly larvae that feed on host tissues) (Lindquist, D. A., et al. *Med Vet Entomol* 6, 2-8 (1992)). Initial field tests were carried out in Florida starting in 1951 and later in 1954 on the island of Curacao (Baumhover, A. H. et al. *J Econ Entomol* 48, 462-466 (1955)). This initial program utilized gamma rays of cobalt to sterilize male pupae (Bushland, R. C. & Hopkins, D. E. *J Econ Entomol* 44, 725-731 (1951)). Adult flies were then dispersed over the island by weekly release from an airplane. After 6 months of releases, screwworm was completely eradicated from the island (Baumhove. Ah. *J Amer Med Assoc* 196, 240 (1966)). Using the same technique, screwworm was eradicated from Florida and the Southeast USA by 1959 (Baumhove. Ah. *J Amer Med Assoc* 196, 240 (1966); Baumhover, A. H., et al. *J Econ Entomol* 52, 1202-1206 (1959)) and entirely from North and Central America by 1995 (Baumhover, A. H. Baumhover: A Personal Account of Screwworm Eradication. *Pioneer Lecture presentation* (1997)). SIT based eradication of the screwworm was later replicated in Libya (1990) when a shipment of contaminated livestock caused an outbreak; the technique has been proven to be a useful suppression tactic for many insects (Lindquist, D. A., et al. *Med Vet Entomol* 6, 2-8 (1992)).

The physical quality or "fitness" of sterile insects produced for SIT is of paramount importance for the application. One downside of canonical sterilization by irradiation is that many insects are not as resilient to this treatment as screwworm. For example, mosquitoes are more sensitive to irradiation and cannot be irradiated without significant fitness reductions and lethality (Benedict, M. Q. & Robinson, A. S. *Trends Parasitol* 19, 349-355 (2003); Dame, D. A., et al. Historical applications of induced sterilization in field populations of mosquitoes. *Malaria J* 8 (2009)). Thus, alternative means of sterilization are useful inventions for the development and application of SIT. These additional methods of inducing sterility in insects include chromosomal disruptions, chemical sterilization, and sex ratio distortion (Benedict, M. Q. & Robinson, A. S. *Trends Parasitol* 19, 349-355 (2003)).

The sterile insect technique involves methods to make male mosquitoes sterile using techniques such as irradiation, chemical sterilization, and/or genetic sterilization techniques. Radiation-sterilization, as used for example in conventional sterile insect technique, is an example of conditional (in this case inducible by irradiation) paternal-effect lethality; sterilization with chemosterilants, e.g. thiotepa, is another. Each of these approaches work by damaging the DNA in the sperm, thus degrading the genetic information that it carries to the point that many zygotes die. US20170188559 describes conditional lethal expression systems for insects, their use, and methods of population control using transformed insects. US20170188559 uses improved female specific, repressible, dominant, lethal genetic system, with earlier onset of the lethal effect. Thus, this method achieves a similar result to techniques such as the Sterile Insect Technique (SIT) in insects, without the problems associated with SIT, such as the cost, danger to the user, and reduced competitiveness of the irradiated organism.

In some embodiments, the male arthropod killing factors and methods of use disclosed herein can be used in combination with an incompatible insect technique (IIT). Cytoplasmic incompatibility (CI) is a conditional sterility induced by a secreted bacterial sperm toxin produced from *Wolbachia* infections in insect gonads. Hannes Laven was the first to pioneer research on *Wolbachia* as a tool for SIT. He described how *Culex pipiens* mosquito isolates were sterile when mated with isolates from different regions of Europe (Laven, H. *Chapter 7: Speciation and Evolution in Culex pipiens.* 251 (Elsevier, 1967)). Realizing the potential, Laven isolated a strain of *Culex pipiens fatigans* (major vector of filariasis) which would be sterile when mated to the same species in Burma. Unbeknownst to Laven, his mosquito strain was infected with a corresponding strain of *Wolbachia* incompatible with the wild type populations in Burma. Despite not understanding the functionality of the sterility, Laven was able to use *Wolbachia* sterilized male mosquitoes to eradicate populations of the local mosquito vector in Burma (Laven, H. *Nature* 216, 383 (1967)).

The IIT methods can use different methods of cytoplasmic incompatibility (CI)-based population suppression. *Wolbachia* bacteria can cause a form of conditional sterility, which can provide an alternative to genetic modification or irradiation. See Mains, J, et al. Female Adult *Aedes albopictus* Suppression by *Wolbachia*-Infected Male Mosquitoes. Sci Rep. 2016 Sep. 23; 6:33846. doi: 10.1038/srep33846. U.S. Pat. No. 7,868,222 is directed to methods for artificially infecting an Aedes mosquito which can be introduced into a mosquito population to control the reproduction capability of the population by introducing an incompatible *Wolbachia* infection. US2013/0259846 is directed to a formulation that may include artificially generated adult insect carriers of a larvicide in which the larvicide has minimal impact on the adult insect and which larvicide affects juvenile survival or interferes with metamorphosis of juvenile insects to adulthood.

WO/2017/214476, discloses methods of utilizing bacterial genes that induce cytoplasmic incompatibility (CI), and discloses the minimal molecular components from the *Wolbachia* genome that are sufficient to induce sterility by a transgenic means, independent of the *Wolbachia* bacterium. U.S. Pat. No. 9,090,911 describes a line of mosquito adapted by infection of variants of the *Wolbachia* strain wMel. See also, Lees, R. et al. Back to the future: the sterile insect technique against mosquito disease vectors. Current Opinion in Insect Science 2015, 10:156-162, which provides additional description of the SIT and IIT technologies.

After sterilization, male insects can then be separated from female insects, delivered to the target site, and released for mating with wild females to eradicate a pest population.

U.S. Pat. No. 9,125,388 describes whereby biological control of an insect is achieved by the release of a dominant negative lethal gene under the control of transcriptional regulators.

The publications describing the SIT and IIT methods above are hereby incorporated by reference in their entirety.

Methods in Combination with Population Replacement Strategies

In some embodiments, the male arthropod killing factors and methods of use disclosed herein can be used in combination with a Population Replacement Strategy (PRS). The goal of PRS is to replace wild pest or vector populations with those that are not competent to function as pests or vectors of human disease (Sinkins, 2004, *Insect Biochem Mol Biol*, 34, 723-9; Dobson, Brelsfoard and Dobson, 2009, *AsPac J. Mol. Biol. Biotechnol.*, 17, 55-63). Population Replacement is dependent on two pieces of technology:
1) A beneficial trait that is desired in the target arthropod
2) A genetic drive mechanism to spread the desired trait through the arthropod population (Sinkins and Gould, 2006, *Nat Rev Genet*, 7, 427-35).

For example, WO/2017/214476, discloses methods of utilizing bacterial genes that induce cytoplasmic incompatibility (CI), which is a natural genetic drive mechanism used by various, unrelated bacterial infections (e.g., *Wolbachia* and *Cardinium* endosymbionts).

Other approaches involving population replacement in the control of disease vectors is the Eliminate Dengue project. This method uses the naturally occurring *Wolbachia* strain wMel to introduce both a desirable trait, the inhibition of mosquito vector competence for Dengue virus and other human pathogens (Walker et al., 2011, *Nature*, 476, 450-3; Aliota et al., 2016, *PLoS Negl Trop Dis*, 10, e0004677; Dutra et al., 2016, *Cell Host Microbe*), and the genetic drive mechanism of CI. This technique has had limited success in field trials, requires massive mosquito releases (Hoffmann et al., 2011, Hoffmann et al., 2014), and the horizontal transfer of *Wolbachia* into hosts that are frequently inhospitable to stable infection (Hughes et al., 2011, *PLoS Pathog*, 7, e1002043; Hughes et al., 2014, *Proc Natl Acad Sci USA*, 111, 12498-503).

Arthropods and Infectious Disease Vectors

The inventors have identified a primary mechanism for the male killing phenotype and disclose herein new methods for control of arthropod (for example, insects) pests and disease vectors, such as mosquitoes transmitting the Dengue fever and Zika viruses.

In one embodiment, the arthropod is an insect. In one embodiment, the arthropod is a mosquito. In one embodiment, the mosquito is selected from the genera consisting of *Aedes*, *Culex* and *Anopheles*. In one embodiment, the mosquito is an *Aedes* mosquito. In one embodiment, the mosquito is an *Anopheles* mosquito. In one embodiment, the mosquito is a *Culex* mosquito. In one embodiment, the *Aedes* mosquito species is selected from the group consisting of *Aedes albopictus*, *Aedes aegypti* and *Aedes polynesiensis*. In one embodiment, the *Anopheles* mosquito species is *Anopheles gambiae*. In one embodiment, the *Culex* mosquito species is *Culex pipiens*.

In one embodiment, disclosed herein are methods for controlling or reducing populations of insects that transmit human or veterinary pathogens. In one embodiment, the pathogen is selected from dengue virus, Zika virus, a malaria parasite (*Plasmodium* genus), West Nile virus, yellow fever virus, chikungunya virus, Japanese encephalitis, St. Louis encephalitis and Western and Eastern Equine Encephalitis viruses.

In one embodiment, disclosed herein are methods for controlling or reducing populations of insects that transmit trypanosomes including African sleeping sickness, Chagas disease, and Nagana. In one embodiment, the pathogen is *Trypanosoma cruzi*. In one embodiment, the pathogen is *Trypanosoma brucei*. In one embodiment, the insect is of the genus *Glossina*. In one embodiment, the insect is *Glossina morsitans*. In one embodiment, the insect is a Tsetse fly. In one embodiment, the insect is a kissing bug. In one embodiment, the insect is of the genus *Rodnius*. In one embodiment, the insect is *Rhodnius prolixus*.

In one embodiment, disclosed herein are methods for controlling or reducing populations of arthropods that transmit rickettsioses and pathogens within Anaplasmatacea including Rickettsias *rickettsii, africae, parkeri, sibirica, conorii, slovaca, peacockii, philipii, rickettsii* Hlp2, *heilongjiangensis, japonica, montanensis, massiliae, rhipicephali, amblyommii, helvetica, monacensis, buchneri, hoogstralli, felis, akari, australis, canadensis, prowazekii, typhi, bellii*. In one embodiment, the arthropod is a tick. In one embodiment, the arthropod is a tick of the genera *Amblyomma*, *Ixodes*, or *Rhipicephalus*. In one embodiment, the disease is epidemic typhus. In one embodiment, the disease is scrub typhus. In one embodiment, the disease is an *Ehrlichiosis*. In one embodiment, the pathogen is of the genus *Ehrlichia*. In one embodiment, the pathogen is of the genus *Anaplasma*. In one embodiment, the pathogen is of the genus *Orientia*. In one embodiment, the arthropod is a chigger of the genus *Leptotrombidium*. In one embodiment, the arthropod is a louse of the genus *Pediculus*. In one embodiment, the arthropod is a flea of the genus *Pulex*.

In one embodiment, disclosed herein are methods for controlling sandflies that transmit leishmaniasis. In one embodiment, the insect is of the genus *Phlebotomus*. In one embodiment, the pathogen is of the genus *Leishmania*. In one embodiment, the pathogen is *Leishmania donovani, Leishmania infantum,* or *Leishmania Chagasi*.

In one embodiment, the insect is of various aphids including: *Acyrthosiphon kondoi, Brevicoryne brassicae, Rhopalosiphum maidis, Aphis gossypii, Aphis craccivora, Myzus persicae, Rhopalosiphum padi, Acyrthosiphon pisum, Rhopalosiphum rufiabdominalis, Metopolophium dirhodum, Aphis glycine, Therioaphis trifolii, Lipaphis erysimi, Rhopalosiphum padi.*

In one embodiment, disclosed herein are methods for controlling the armyworm agricultural pest species including *Leucania convecta, Spodoptera exempta, Spodoptera Mauritia, Spodoptera exigua, Mythimna separate, Leucania stenographa.*

In one embodiment, disclosed herein are methods for controlling pests of beans and beets. In one embodiment, the insect is either the Bean fly (*Ophiomyia phaseoli*), the Bean leafroller (*Omiodes diemenalis*), the Bean looper or *Mocis* (*Mocis alterna*), the Bean podborer (*Maruca vitrata*), the Bean spider mite (*Tetranychus ludeni*), the Beet webworm (*Spoladea recurvalis*), the Large Brown bean bug (*Riptortus serripes*), the Small Brown bean bug (*Melanacanthus scutellaris*)

In one embodiment, disclosed herein are methods for controlling the Blue oat mite (*Penthaleus major*). In one embodiment, the invention is useful for controlling the Brown flea beetle (*Chaetocnema* sp.). In one embodiment, the invention is useful for controlling the Brown mind (*Creontiades pacificus*). In one embodiment, the invention is useful for controlling the Brown shield bug (*Dictyotus caenosus*). In one embodiment, the invention is useful for controlling the Brown wheat mite (*Petrobia latens*). In one embodiment, the invention is useful for controlling the Bruchid, Cowpea (*Callosobruchus maculatus*).

In one embodiment, disclosed herein are methods for controlling pests of Corn including: the Corn aphid (*Rhopalosiphum maidis*), and the Corn earworm (*Helicoverpa armigera*).

In one embodiment, the invention is useful for controlling pests of cotton including the Cotton aphid (*Aphis gossypii*), Cotton bollworm (*Helicoverpa armigera*), the Cotton harlequin bug (*Tectocoris diophthalmus*), the Cotton leafhopper (*Amrasca terraereginae*), the Cotton leafperforator (*Bucculatrix gossypii*), the Cotton looper (*Anomis flava*), the Cottonseed bug (*Oxycarenus luctuosus*), the Cotton seedling thrip (*Thrips tabaci*), the Cotton tipworm (*Crocidosema plebejana*), and the Cotton webspinner (*Achyra affinitalis*).

In one embodiment, disclosed herein are methods for controlling the Diamondback moth (*Plutella xylostella*). In one embodiment, the invention is useful for controlling the Dried fruit beetle (*Carpophilus* spp.). In one embodiment, the invention is useful for controlling the Eastern false wireworm (*Pterohelaeus* spp.). In one embodiment, the invention is useful for controlling the *Etiella* moth (*Etiella behrii*). In one embodiment, the invention is useful for controlling the False wireworm (*Pterohelaeus* and *Gonocephalum* spp.). In one embodiment, the invention is useful for controlling the Flea beetles, Brown and Redheaded (*Chaetocnema* and *Nisostra* sp.). In one embodiment, the invention is useful for controlling the Flower beetle (*Carpophilus* spp.).

In one embodiment, disclosed herein are methods for controlling various Grasshoppers and locusts including the Grasshopper, Wingless (*Phaulacridium vittatum*), the Locust, Australian plague (*Chortoicetes terminifera*), the Locust, Migratory (*Locusta migratoria*), the Locust, Yellow-winged (*Gastrimargus musicus*), the Locust, Spur-throated (*Austracris (Noamdacris) guttulosa*).

In one embodiment, the invention is useful for controlling the Greenhouse whitefly (*Trialeurodes vaporariorum*). In one embodiment, the invention is useful for controlling the Green peach aphid (*Myzus persicae*). In one embodiment, the invention is useful for controlling the Green mind (*Creontiades dilutus*). In one embodiment, the invention is useful for controlling the Green vegetable bug (*Nezara viridula*). In one embodiment, the invention is useful for controlling the Green stink bug (*Plautia affinis*). In one embodiment, the invention is useful for controlling the Grey cluster bug (*Nysius clevelandensis*). In one embodiment, the invention is useful for controlling the *Helicoverpa* species (*armigera* and *punctigera*).

In one embodiment, disclosed herein are methods for controlling planthoppers. In one embodiment, the insect is the small brown planthopper (*Laodelphax striatellus*). In one embodiment, the invention is useful for preventing the transmission of crop diseases like Rice White Stripe Virus. In one embodiment, the invention is useful for controlling vectors of plant pathogens.

In one embodiment, disclosed herein are methods for controlling the Jassids and various leafhoppers including the Leafhopper, cotton (*Amrasca terraereginae*), the Leafhopper, lucerne (*Austroasca alfalfae*), the Leafhopper, maize (*Cicadulina bimaculata*), the Leafhopper, vegetable (*Austroasca viridigrisea*).

In one embodiment, disclosed herein are methods for controlling the Loopers including the Looper, Brown pasture (*Ciampa arietaria*), the Looper, Castor oil (*Achaea janata*), the Looper, Cotton (*Anomis flava*), the Looper, Sugarcane (*Mocis frugalis*), the Looper, Soybean (*Thysanoplusia orichalcea*), the Looper, Tobacco (*Chrysodeixis argentifera*), the Looper, Vegetable (*Chrysodeixis eriosoma*).

In one embodiment, disclosed herein are methods for controlling various Thrip pests including the Onion Thrip (*Thrips tabaci*), the Cotton seedling Thrip (*Thrips tabaci*), the Maize Thrip (*Frankliniella williamsi*), the Plague Thrip (*Thrips imaginis*), the tobacco Thrip (*Thrips tabaci*), the Tomato Thrip (*Frankliniella schultzei*), the Western flower Thrip (*Frankliniella orientalis*)

In one embodiment, disclosed herein are methods for controlling various Mite pests including the Mite, Bean spider (*Tetranychus ludeni*), Mite, Brown wheat (*Petrobia latens*), Mite, Blue oat (*Penthaleus* major), Mite, Peanut (*Paraplonobia* spp.), Mite, Redlegged earth (*Halotydeus destructor*), Mite, Strawberry spider (*Tetranychus lambi*), and the Two-spotted mite (*Tetranychus urticae*).

In one embodiment, disclosed herein are methods for controlling various whitefly pests including the Greenhouse whitefly (*Trialeurodes vaporariorum*), the Silverleaf whitefly (*Bemisia tabaci* biotype B and Australian native AN), and the Silverleaf whitefly (*Bemisia tabaci* biotype Q).

In one embodiment, disclosed herein are methods for controlling various fruit pests. In one embodiment, the arthropod is from the genera *Drosophila*. In one embodiment, the arthropod is *Drosophila suzukii*. In one embodiment, the arthropod is *Drosophila recens, Drosophila subquinaria, Drosophila innubila*, or related *Drosophila* species. *Drosophila suzukii*, commonly called the spotted-wing *drosophila*, is a vinegar fly closely related to *Drosophila melanogaster*. Unlike its vinegar fly relatives who are primarily attracted to rotting or fermented fruit, *D. suzukii* attacks fresh, ripe fruit by laying eggs under the soft skin. The larvae hatch and grow in the fruit, destroying the fruit's commercial value. The pest particularly (but not limited to) infests cherries, apples, apricots, persimmons, tomatoes, blueberries, grapes, nectarines, pears, plums, peaches, figs, raspberries and strawberries. Although *D. suzukii* is native to Southeast Asia, the fruit pest has recently invaded North and Central America as well as Europe, where it is expanding rapidly. Effective management of this pest is a challenge owing to the wide host range and short generation time. Therefore, monitoring and controlling *D. suzukii* is of great economic importance. However, traps and baits containing for instance apple cider vinegar, which are typically used for attracting vinegar flies such as *D. melanogaster*, are less efficient for attracting and trapping *D. suzukii*. In one embodiment, the insect is the Mexican Fruit Fly (*Anastrepha ludens*). In one embodiment, the insect is the Mediterranean Fruit Fly (*Ceratitis capitata*). In one embodiment, the insect is of the genus *Anastrepha, Bactrocera*, or *Ceratitis*. In one embodiment, the insect is a tephritid.

In one embodiment, disclosed herein are methods for controlling various other agricultural pests including: the red-houldered leaf beetle (*Monolepta australis*), Native budworm (*Helicoverpa punctigera*), Native whitefly (*Bemisia tabaci*), Northern armyworm (*Mythimna separata*), Oat aphid (*Rhopalosiphum padi*), Onion thrip (*Thrips tabaci*), Pale cotton stainer bug (*Dysdercus sidae*), Pea aphid (*Acyrthosiphon pisum*), Pea blue butterfly (*Lampides boeticus*), Peanut mite (*Paraplonobia* spp.), Peanut scarab (*Heteronyx* spp.), Pea weevil (*Bruchus pisorum*), Pinkspotted bollworm (*Pectinophora scutigera*), Plague thrip (*Thrips imaginis*), Podsucking bugs (*Nezara viridula*), Redbanded shield bug (*Piezodorus oceanicus*), Redheaded flea beetle (*Nisotra* sp.), Redlegged earth mite (*Halotydeus destructor*), Redshouldered leaf beetle (*Monolepta australis*), Rice root aphid (*Rhopalosiphum rufiabdominalis*), Rose grain aphid (*Metopolophium dirhodum*), Rough bollworm (*Earias huegeliana*), Rutherglen bug (*Nysius vinitor*), Seed harvesting ants (*Pheidole* spp.), Scarab, Black sunflower (*Pseudoheteronyx* sp.), Scarab, Peanut (JPG, 20.4 KB) (*Heteronyx* sp.), Shoot flies (*Atherigona* sp.), Silverleaf whitefly (*Bemisia tabaci* biotype B and Australian native AN), Silverleaf whitefly (*Bemisia tabaci* biotype Q), Sitona weevil (*Sitona discoideus*), Solenopsis mealybug (*Phenacoccus solenopsis*), Sorghum midge (*Stenodiplosis sorghicola*), Sorghum head caterpillar (*Cryptoblabes adocta*), Soybean leafminer (*Porphyrosela aglaozona*), Soybean looper (*Thysanoplusia orichalcea*), Soybean moth (*Aproaerema simplexella*), Spotted alfalfa aphid (*Therioaphis trifolii*), Spur-throated locust (*Austracris (Nomadacris) guttulosa*), Strawberry spider mite (*Tetranychus lambi*), Swarming leaf beetle (*Rhyparida* spp.), Tortrix (*Epiphyasa postvittana*), True wireworm (*Agrypnus* spp.), Vegetable weevil (*Listroderes difficilis*), Weed web moth (*Achyra affinitalis*), Whitegrub (*Heteronyx* spp.), Wingless cockroaches (*Calolampra* spp.), Wireworm, False (*Pterohelaeus* and *Gonocephalum* spp.), Wireworm, True (*Agrypnus* spp.), Yellow peach moth (*Conogethes punctiferalis*). In one embodiment, the insect is *Heteronychus arator*. In one embodiment, the insect is of the genus *Amnemus*. In one embodiment, the insect is of the genus *Pheidole*. In one embodiment, the invention is useful for controlling the Black field cricket (*Teleogryllus commodus, T. oceanicus, Lepidogryllus parvulus*), the Black field earwig (*Nala lividipes*), the Black leaf beetle (*Rhyparida nitida*), the Black sunflower scarab (*Pseudoheteronyx* sp.). In one embodiment, the invention is useful for controlling the Cowpea bruchid (*Callosobruchus maculatus*). In one embodiment, the invention is useful for controlling the Cricket, Black field (*Teleogryllus commodus, T. oceanicus, Lepidogryllus parvulus*). In one embodiment, the invention is useful for controlling the Crop mind (*Sidnia kinbergi*). In one embodiment, the invention is useful for controlling the Cutworm (*Agrotis* spp.). In one embodiment, the invention is useful for controlling the Cabbage moth (*Plutella xylostella*). In one embodiment, the invention is useful for controlling the Castor oil looper (*Achaea janata*). In one embodiment, the invention is useful for controlling the Click beetle (*Agrypnus* spp.). In one embodiment, the invention is useful for controlling the Clover springtail (*Sminthurus viridis*). In one embodiment, the invention is useful for controlling the Cluster caterpillar (*Spodoptera litura*). In one embodiment, the invention is useful for controlling the Cockroach, Wingless (*Calolampra* spp.). In one embodiment, the invention is useful for controlling the Common grass blue butterfly (*Zizina labradus*). In one embodiment, the invention is useful for controlling the Legume webspinner (*Omiodes diemenalis*). In one embodiment, the invention is useful for controlling the Light brown apple moth (*Epiphyas postvittana*). In one embodiment, the invention is useful for controlling *Mocis trifasciata*. In one embodiment, the invention is useful for controlling *Pantydia* spp. In one embodiment, the invention is useful for controlling the Lucerne crownborer (*Zygrita diva*). In one embodiment, the invention is useful for controlling the Lucerne flea (*Sminthurus viridis*). In one embodiment, the invention is useful for controlling the Lucerne leafhopper (*Austroasca alfalfae*). In one embodiment, the invention is useful for controlling the Lucerne leafroller (*Merophyas divulsana*). In one embodiment, the invention is useful for controlling the Lucerne seed wasp (*Bruchophagus roddi*). In one embodiment, the invention is useful for controlling the Lucerne seed web moth (*Etiella behrii*).

In one embodiment, disclosed herein are methods for controlling forestry and wildlife pests such as the emerald ash borer. In one embodiment, the insect is of the genus *Agrilus* or specifically *Agrilus planipennis*. In one embodiment, the invention is useful for pests of trees and lumber.

In one embodiment, disclosed herein are methods for controlling various arthropods including *Adalia bipunctata* (two-spotted lady beetle), other ladybug species/genera (*Harmonia, Adalia decempunctata, Cadra cautella* (and other *Cadra* moths), *Ephestia kuehniella* (and other *Ephestia* moths), *Cordylochernes scorpioides* (pseudoscorpion), *Tribolium* (flour beetles), *Hypolimnas* butterflies, *Acraea* butterflies, or *Ostrinia* moths.

EXAMPLES

The following examples are set forth below to illustrate the compositions, methods, and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Example 1. wmk is a *Wolbachia* Prophage Gene that Kills Male *Drosophila* Embryos

*Wolbachia* are maternally-transmitted bacteria that infect almost half of all arthropod species and many nematode species. In arthropods, these bacteria often selfishly manipulate host reproduction to enhance the fitness of infected females, thereby facilitating their own transmission and spread through the host population. Despite significant impacts of *Wolbachia* on animal reproduction[1], evolution[2-5], and vector control[6,7], the bacterial genes underlying most of these reproductive manipulations remain elusive. One such phenotype is male killing, where the sons of infected females are selectively killed. In this example, it is demonstrated that a single gene in the eukaryotic association module of prophage WO[8] kills male *Drosophila* embryos. The gene, hereafter denoted WO male killing (wmk), causes male lethality when transgenically expressed in uninfected *Drosophila melanogaster*. Expression of wmk results in a female-biased sex ratio, reduced hatching of male embryos, and male-specific cytological defects during early embryonic development that are typical of *Wolbachia*-induced male killing. The discovery of wmk commences microbial genetic studies of male killing, highlights the significance of genes carried by mobile genetic elements in shaping selfish symbiont phenotypes, and provides compositions and methods of male killing in suppression or modification of pest and vector populations[6,7,9].

Background

*Wolbachia* (Order Rickettsiales) infect an estimated 40-52% of all arthropod species and 47% of filarial nematode species, making them the most widespread intracellular bacterial symbiont in animals. Concentrated in host testes and ovaries, *Wolbachia* primarily transmit cytoplasmically from mother to offspring. In arthropod reproductive tissues and fertilized embryos, *Wolbachia* deploy cunning manipulations to achieve a greater proportion of transmitting females in the host population. Collectively, these strategies are categorized as reproductive parasitism.

Male killing, or selective death of an infected female's sons, is one such form of reproductive parasitism. It enhances the fitness of *Wolbachia*-infected females in three potential ways: (i) reducing brother-sister competition for limited resources, (ii) reducing inbreeding, and/or (iii) providing nutrients in cases where infected sisters cannibalize embryos of their dead brothers. Male-killing *Wolbachia* are widespread in several major insect orders and in pseudoscorpions. In addition, male-killing *Spiroplasma, Rickettsia*, and *Arsenophonus* occur in diverse hosts including flies, ladybugs, and wasps.

Male killing can have several significant impacts on host evolution. For example, male death may lead to host extinction or reduce the effective population size of the host. As a consequence, theory specifies that fixation of deleterious alleles in host populations is more likely, and fixation of beneficial alleles is conversely less likely. Male killing can also impose strong selection on hosts to counter the sex ratios shifts and lethality. Evolutionary outcomes include mate preference between uninfected males and females, a shift towards more mate-attracting behaviors by females or male mate choice, and suppression of the phenotype.

As they manipulate arthropod reproduction to drive through host populations, *Wolbachia* are currently used in two vector control strategies: population suppression to reduce the population size of mosquitoes and population replacement to transform mosquito populations that transmit pathogens to ones that cannot transmit pathogens. This is through the application of another parasitism phenotype, cytoplasmic incompatibility (CI), where most offspring of infected males and uninfected females are killed. Notably, population genetic modeling demonstrates that male killing can be deployed in conjunction with population suppression techniques to speed up eradication or reduction of a target arthropod population and increase the likelihood of success. However, the genetic basis of *Wolbachia* male-killing has remained a mystery for more than sixty years and the causative gene of the *Spiroplasma* male-killing phenotype has only recently been reported, so vector and pest control applications have yet to be experimentally validated. This is largely due to the inability to culture these obligate intracellular bacteria.

Results

Genomic Analysis of Male-Killing Gene Candidates

In this example, the inventors sought to determine the *Wolbachia* genetic basis of the male-killing phenotype. Notably, *Wolbachia* can be multipotent because some strains induce at least two reproductive parasitism phenotypes (e.g., CI and male killing) depending on the host background or environmental conditions. For example, the wRec strain of *D. recens* causes CI in its native host but kills males when introgressed into the genetic background of its sister-species, *D. subquinaria*. Importantly, wMel and wRec share 99.7% nucleotide identity, which raises the hypothesis that the CI-inducing wMel genome may also harbor male killing genes. Although wMel is not known to naturally cause male killing, it is of interest because it is the natural strain of the only host that is genetically tractable and is so closely-related to a natural male killer, making it the best current system to test *Wolbachia* gene candidates for the phenotype. A long-standing question is whether multipotency is due to the same gene(s) expressing different reproductive parasitism phenotypes or alternatively if different genes underpin the various forms of reproductive parasitism. Several reproductive parasitism gene candidates were previously assessed for both male killing and CI, including cifA and cifB, and were ruled out their involvement in male killing.

There are several expectations for a putative *Wolbachia* male-killing gene. First, transgenic expression should recapitulate the embryonic cytological defects typically induced by male killing. Second, *Wolbachia* expression of the candidate gene should occur by the time male death naturally occurs in a given host. Third, a male-killing *Wolbachia* gene should be shared across male-killing strains but not necessarily absent from strains not known to cause male killing. In other words, the gene may be more common than the phenotype because hosts commonly develop resistance to male killing, presumably due to the strong evolutionary pressure to avoid extinction. Indeed, as previously mentioned, *Wolbachia* can induce either male killing or CI in different hosts or rearing conditions, which may be related to resistance in some hosts. Fourth, if there is a single gene that causes male killing in most or all cases, then the gene may rapidly evolve due to natural selection in diverse host backgrounds that suppress male killing. In this example, based on genomic analyses, transgenic expression, and cytological characterizations, a prophage WO gene from wMel *Wolbachia* of *Drosophila melanogaster* that causes male killing is identified.

To generate a shortlist of male-killing gene candidates, the following criteria were used: (i) universal presence in the genomes of male-killing strains wBif from *D. bifasciata*, wInn from *D. innubila*, wBor from *D. borealis*, wRec from *D. recens* as well as the CI strain nearly identical to wRec, wMel from *D. melanogaster*; (ii) genomic location in at least one prophage WO region because parasitic *Wolbachia* all have intact or remnant prophage WO regions with eukaryotic association module genes, and the two previous parasitism genes, cifA and cifB, are both prophage genes, making it likely that other parasitism genes share a phage origin; (iii) exclusion of highly repetitive elements, including insertion sequence elements, reverse transcriptases of group II intron origin, and large serine recombinases that likely facilitate phage WO lysogeny; and (iv) exclusion of disrupted genes (e.g., early stop codons) in one or more strains.

Table 1 shows seven genes from *Wolbachia* that fit these criteria. One of these genes, cifA, was previously evaluated by transgenic expression, and it did not exhibit a biased sex ratio. Others include a predicted ankyrin repeat (WD0550), two Rpn genes (recombination-promoting nucleases WD0297, WD0627), Phospholipase D (WD1243), and a hypothetical protein (WD0628). The remaining gene, WD0626, was a gene identified in multi-omic analysis for CI genes. This gene, hereafter denoted wmk for WO-mediated killing, is a putative transcriptional regulator in prophage WOMelB that is predicted to encode two helix-turn-helix (XRE family) DNA-binding domains (NCBI conserved domains E=$5.9 \times 10^{-11}$. E=$6.5 \times 10^{-10}$). wmk in wMel has a single amino acid difference relative to its homolog in wRec. Therefore, it was assessed for putative male killing.

The wmk Gene is Common and Found in all Sequenced Male-Killing Genomes

Phylogenetic analyses indicate that wmk homologs are common in phage WO-containing *Wolbachia* including the above-mentioned male-killing strains (Fig. S1), wBol from *Hypolimnas bolina* butterflies (causes CI when male killing is suppressed), and wCauB from *Cadra cautella* moths (causes male killing in non-native host), along with many strains not known to cause male killing (FIG. 11). wmk is in the eukaryotic association module of prophage WOMelB, resides just a few genes away from the cif genes, and exists in multiple divergent copies in some strains (FIG. 4; FIG. 11). Phylogenetic analyses indicate that wmk sequence relationships do not cluster into typical *Wolbachia* supergroups (FIG. 11), indicating independent evolution relative to the core *Wolbachia* genome. This finding is similar to that of other prophage WO genes including cifA, cifB, and the baseplate assembly gene, gpW. It is attributable to the high rates of horizontal phage WO transfer between *Wolbachia* coinfections. Similar to cifA and cifB, wmk homologs notably degraded in the parthenogenesis-inducing *Wolbachia* strains wUni from *Muscidifurax uniraptor* wasps, wTpre from *Trichogramma pretiosum* wasps, and wFol from *Folsomia candida* springtails. In addition, genomic analyses suggest the full version of wmk in phage WO originated from a fusion or duplication event with gene(s) in the non-prophage region of the *Wolbachia* chromosome. Indeed, homologs of the N-terminal XRE-family HTH domain occur in distantly related nematode *Wolbachia* strains (wWb, wBm, wPpe) and the sister genera *Ehrlichia* (Table 3) that all lack prophage WO.

wmk (locus WD0626 in the wMel *Wolbachia* genome of *Drosophila melanogaster*) is a putative transcriptional regulator in prophage WOMelB that encodes two putative helix-turn-helix (HTH_XRE) DNA-binding domains (NCBI conserved domains E=$5.9 \times 10^{-11}$, E=$6.5 \times 10^{-10}$). Comparative genomic studies originally identified wmk and its homologs as candidates for inducing cytoplasmic incompatibility (CI)[10-12], which is a common type of reproductive parasitism whereby crosses between infected males and uninfected females result in embryonic lethality. Rescue of this lethality occurs if the female and her eggs are infected with a compatible *Wolbachia* strain. CI, however, was later attributed to the nearby prophage WO genes cifA and cifB[10,13]. Given that CI-causing *Wolbachia* can be multipotent and also cause male killing, depending on the host and environmental conditions[14-16], wmk was functionally interrogated to assess its potential involvement in male killing. Notably, wmk in wMel has a single amino acid difference compared to its homolog in the wRec strain[17] that is capable of male killing when moved to a non-native host[15]. Moreover, these two genomes share 99.7% nucleotide identity.

Expression of wmk in Fruit Flies Causes a Female-Biased Sex Ratio

Transgenic *D. melanogaster* flies were generated that express codon-optimized wmk (codons changed to those preferentially used by *Drosophila*) with the Gal4-UAS expression system. Three other transgenes were also evaluated: WD0625 in prophage WO that encodes a putative MPN/Mov34/PAD-1 metalloprotease domain (DUF2466, NCBI conserved domain E=$3.85 \times 10^{-41}$), WD0508 in the prophage WO-associated Octomom region that is another predicted transcription regulator with two HTH_XRE DNA-binding domains (NCBI conserved domains E=$1.70 \times 10^{-9}$, E=$1.99 \times 10^{-11}$, a homolog of wmk), and WD0034, a hypothetical non-phage gene that is hereafter labeled 'control gene' and shares a transgenic insertion site with wmk. These three genes were previously described and do not recapitulate CI[10]. In the experiments below, these transgenes were expressed within heterozygotes under the control of an Act5c-Gal4 driver, which leads to strong, ubiquitous transgene expression beginning with zygotic transcription ~2 h after egg deposition (aed) and continues through adulthood. Genetic crossing schemes for all experiments are described in the methods.

To assess potential male killing, adult sex ratios were first quantified in gene-expressing (Act5c-Gal4; UAS-wmk) flies. wmk transgene expression beginning in early embryogenesis of uninfected *D. melanogaster* results in a significant reduction in the average male:female sex ratio (number of males/number of females) to 0.65, suggesting a 35% reduction in gene-expressing males (FIG. 1). The sex ratio is approximately 1 in transgenic flies that do not express wmk (CyO; UAS-wmk), flies that express a control gene, and wild type flies (FIG. 1). Stated differently, wmk expression results in a shift to 39% males rather than the expected 50%. No changes in sex ratios occur when other prophage WO genes are transgenically expressed in uninfected flies (FIG. 5a-c). Though a significant number are killed, not all gene-expressing males die. One possible reason is that another *Wolbachia* or prophage WO gene may be involved. Since the neighboring CI genes, cifA and cifB, must be co-expressed to induce CI, wmk was co-expressed with its neighbor, WD0625. It was found that the sex ratio of the two genes co-expressed is not significantly different than when wmk is expressed alone (FIG. 5a-c). Thus, WD0625 does not appear to contribute to male killing in this expression system. It is possible that other genes are involved, but none have yet been identified. Notably, lack of sex ratio bias by expression of alternative transgenes indicates that the wmk-induced phenotype is not due to a generalized, transgenic artifact. Next, to test if the timing of expression contributed to the lack of complete male death, Sex ratios were investigated under a second expression driver. The maternal triple driver (MTD) was used, which drives early transgene expression in the maternal germline throughout oogenesis[18]. There is no significant difference in sex ratio between wmk and any other genotype (FIG. 5d), despite confirmed expression under this driver (FIG. 5e). These results indicate that the wmk-induced sex ratio effect occurs after zygotic transcription (~2 h aed) under the Act5c driver, and that it is not likely that an earlier time window necessary to kill all males is missing.

The wmk-induced change in sex ratio is not consistent with other forms of reproductive parasitism. Results are not CI-like because (i) CI is not known to have a sex ratio bias[10], (ii) the phenotype begins long after hallmark CI defects such as delayed histone deposition[19] and (iii) an infected background does not rescue the wmk phenotype, as would be observed if the effect were related to CI (FIG. 6a). Moreover, neither wmk expression nor dual expression of wmk and its neighbor WD0625 causes or rescues CI when expressed with the nanos-Gal4 driver used in previous CI experiments for germline-specific expression[10] (FIG. 6b,c). The bias in sex ratio cannot result from genetic males developing as females (feminization), as wmk expression did not increase the absolute number of females (FIG. 6d), and cytology data using a Y chromosome FISH probe demonstrates that the number of female wmk embryos laid and the number of viable female wmk embryos in late embryogenesis are not significantly different compared to controls (see below). Finally, parthenogenesis (where female hosts reproduce without sperm) would also not fit the phenotype because expression and the phenotype occur with a paternal chromosome present. Therefore, the phenotype fits the profile of male killing.

Expression of wmk in Fruit Flies Recapitulates Embryonic Death and Cytological Defects

*Wolbachia*-induced male killing typically occurs during embryogenesis in *Drosophila*[20] To assess if wmk-induced male lethality is embryonic, the proportion of all embryos that hatch into larvae were examined (note only half of embryos express the transgene, see methods). The mean hatch rate from the wmk transgenic line (79.5%) was significantly lower than the mean hatch rate for control WD0034 embryos (91%) and WT embryos (86.4%) (FIG. 7a). In addition, sex ratios in surviving third instar larvae (combined expressing and non-expressing, see methods) were also significantly reduced (0.82) compared to those of the control gene (0.96) and wild type (0.95) lines (FIG. 7b). The reduction in embryonic hatch rate and larval sex ratio are moderate, but consistent with the 35% reduction in wmk-expressing adult males (FIG. 1) is extrapolated to include combined expressing and non-expressing offspring. Thus, wmk-induced death is embryonic.

Typical cytological defects associated with *Wolbachia*-induced male killing in *D. bifasciata* span abnormal nuclei distribution, chromatin bridging, and pyknosis in male embryos and they begin largely at the time of host embryonic cellularization, which occurs ~2.5 h aed[20]. To determine if wmk transgene expression in *D. melanogaster* also causes these same defects, DNA was stained with propidium iodide in wild type (WT) embryos and embryos expressing either wmk or the control transgene. The defects in embryos were then monitored (only half the embryos are expected to express the transgene, see methods). Several different defects were observed among embryos (FIG. 2a-d). In embryos fixed 1-2 h aed, there was no significant difference in cytological defects of wmk-associated offspring compared to controls (FIG. 2i). However, in embryos fixed 3-4 h aed, cytological defects were enriched in wmk-associated embryos (28%) relative to control gene embryos (11.8%) and wild type embryos (10.3%) (FIG. 2j). Since defects were seen in embryos fixed 3-4 h aed but not those fixed 1-2 h aed, the defects could start forming any time 2-4 h aed. Some embryos may already have formed lethal defects before fixing 3-4 h aed. These results also demonstrate that cytological defects specifically occur soon after zygotic transcription of wmk.

To determine if the defects in embryos resulted in visible abnormalities later in development, sibling embryos were fixed in a late stage of embryonic development, 16-17 h aed. There was a significant increase in necrotic embryos (embryos with cloudy staining from degraded DNA and lack of distinct nuclei) in wmk-associated offspring compared to controls. One category of necrotic embryos had no visible cephalic furrow or segmentation similar to unfertilized embryos (FIG. 2e,f). These embryos occurred equally across all treatment groups at a percentage similar to that of unfertilized eggs (FIG. 2e,k) measured in a batch of sibling offspring. This indicates that they are likely decomposing, unfertilized eggs. A second necrotic form exhibited a cephalic furrow that demarcates the head from the thorax (FIG. 2g), but lacked other normally visible segmentation (FIG. 2h). There were approximately 10-fold more necrotic embryos with a cephalic furrow in the wmk cross versus controls (FIG. 2k). This appears to narrow down the time of death to soon after cephalic furrow formation, which begins around 3 h aed. This is the time point when cytological defects first occur (FIG. 2j). The furrow is largely formed by 4 h aed, and this formation is visible in the necrotic embryos, suggesting some embryos can pass through this developmental time point before death. Notably, the 11% absolute increase in necrotic cephalic furrow from wmk embryos compared to controls (FIG. 2k) is similar to the level of decreased embryonic hatch rates previously mentioned (FIG. 7a). These results imply that the necrotic embryos 16-17 h aed and the reduced hatch rates are the result of wmk-induced defects in early embryos. The corresponding adult sex ratios for this experiment are shown in FIG. 8a.

To demonstrate that the cytological defects are male-specific, fluorescent in situ hybridization (FISH) was performed on embryos with a DNA probe specific to the Y chromosome (FIG. 9, expressing and non-expressing embryos, see methods). 40% of male wmk embryos fixed 3-4 h aed exhibit defects compared to 9% of female wmk embryos and 9-10% of WT and control gene embryos at the same developmental stage (FIG. 3a). In addition, while the embryonic sex ratios are not biased at 1-2 h aed, they are biased among viable (non-necrotic) embryos fixed 16-17 h aed (FIG. 3b). The corresponding adult sex ratio of 0.68 was the same as the embryonic sex ratio (FIG. 8b), further indicating that male killing occurs during embryogenesis. These results specify that defects are enriched in males and that the necrotic embryos are largely male.

wmk is Expressed in *Drosophila* Embryos Infected with *Wolbachia*

To establish a native gene expression profile of wmk, relative transcript abundance was measured in *Wolbachia*-infected embryos fixed 4-5 h aed (estimated time of death). In wMel-infected embryos, native wmk and control gene transcripts were approximately 10-fold lower than the highly expressed CI gene, cifA (FIG. 10a). There were no significant differences with either gene compared to the less abundant cifB CI gene transcript. Further, expression levels of the wmk and control transgenes are similar to each other (FIG. 10b), and it was confirmed that transgene expression of both wmk and the control gene is approximately 800 times higher than the native transcripts from *Wolbachia*

(FIG. 10b). This suggests high expression levels of wmk lead to a sex ratio bias in this host. However, D. bifasciata embryos infected with wBif male-killing Wolbachia showed an expression profile similar to wMel, where cifA is expressed significantly higher than wmk. This indicates that high expression levels of wmk may not be necessary to induce male killing in native infections and may only be required in certain cases.

wmk homologs are common in phage WO-containing Wolbachia including the male-killing strains wInn (D. innubila)[21], wBor (D. borealis)[22] wRec (D. recens, causes male killing in non-native host)[15], wBol (Hypolimnas bolina, causes CI when male killing is suppressed)[3,23], and wCauB (Cadra cautella, causes male killing in non-native host)[16] (FIG. 11a). It is one of three closely related transcriptional regulators in the eukaryotic association module (EAM)[8] of prophage WOMelB, a region enriched with genes of eukaryotic function and homology (FIG. 4, FIG. 11b). Homologs in addition to those three are located within other prophage WO regions in wMel (FIG. 4). Phylogenetic analyses indicate that wmk sequence relationships do not cluster into typical Wolbachia supergroups (FIG. 11a), following a similar trend established for prophage WO genes cifA, cifB and gpw[10]. A partial homolog is found in a prophage region of the wBif male-killing strain of D. bifasciata[14], which has a single HTH_XRE domain and is most closely related to a nearby WOMelB homolog of wmk, WD0622 (FIG. 4, FIG. 11b). wmk homologs were not detected in the parthenogenesis-inducing Wolbachia strains wUni (Muscidifurax uniraptor), wTpre (Trichogramma pretiosum), or wFol (Folsomia candida). The gene was also not present in the male-killing MSRO strain of Spiroplasma poulsonii. Genomic analyses suggest that a full version of wmk likely originated from a fusion or duplication event with gene(s) in the non-prophage region of the Wolbachia chromosome because homologs of the N-terminal HTH_XRE domain occur in distantly related nematode Wolbachia strains (wWb, wBm, wPpe) and the earlier branching Ehrlichia canis (Table 3) that all lack prophage WO.

The relationship between multipotent Wolbachia genotype and phenotype is complex, but some patterns emerge. First, although transgenic wmk induces a male-killing phenotype in D. melanogaster, its native Wolbachia strain, wMel, induces CI[10]. Notably, wRec causes male killing when transferred to its sister species, D. subquinaria[15]. This is also known to occur in the opposite direction, where suppression of a male killer can lead to CI induction, indicating that male killing and CI strains may be able to switch back and forth between the two phenotypes[23]. Given that wRec and wMel and their wmk homologs are so closely related, it is possible that wMel can also phenotype switch from CI to male killing depending on the host. Second, and more generally across Wolbachia strains, while CI genes and phenotype often correlate, wmk is not always associated with male killing. For example, while CI-capable strains wMel and wRec have cifA and cifB genes, several strains that are not known to cause CI, including wInn, have unusual cifB homologs with stop codons in the middle of the gene, suggesting they are unable to induce CI (FIG. 4). On the other hand, wmk and its homologs are intact in all these strains and are very common genes in prophage WO despite not universally associating with male killing (FIG. 11a). In wMel, lack of male killing in its native host could be explained by lower D. melanogaster susceptibility to male killing, as in D. recens[15], differences in Wolbachia titers, and/or insufficient expression of native wmk within this host. Some of these factors may apply to other strains as well.

While around a third of gene-expressing males are killed, transgene expression of wmk in D. melanogaster does not kill all gene-expressing males even though complete male death is typical in the wild. This could be for several reasons. First, the single amino acid difference between the protein sequences of wMel wmk and wRec wmk may account for the discrepancy. Second, another gene may additively contribute to male killing. This possibility has not been ruled out, but the most likely candidate, WD0625, does not appear to be involved. A third possibility is that expression may need to be at a different time, however, neither an egg-loading driver nor the ubiquitously and early-expressed Act5c-Gal4 driver leads to total male death. Fourth, variation in expression levels among individuals may be a factor. Finally, several host species are resistant to male killing[3,15]. It is possible that D. melanogaster is not as susceptible to male killing as other hosts like D. subquinaria, and it is only through high levels of transgene expression that males die. This could be why high levels of wmk expression are required for male death in this system, but not necessarily in natural cases of male killing (FIG. 10c). The exact reason for the lack of complete death awaits further study.

The Wmk Protein is a Putative DNA-Binding Protein

Phyre 2 protein modeling was used to predict that Wmk from wMel is globular and composed of α-helical secondary structures matching several transcriptional regulators, suppressors, and DNA-binding proteins (FIG. 12). The best match, based on both alignment confidence and sequence identity, to known protein structures is the Salmonella-temperate phage Rep-Ant complex, a dimerized DNA-binding and peptide-binding repressor (99.8% homology confidence. 19% sequence identity, FIG. 12(B)). Wink may function similarly as a bipartite protein where the dimers are physically connected, especially considering that single HTH domains typically dimerize and act as transcriptional regulators across domains of life. Further, predicted structures of the Wmk homologs in wBif (FIG. 12(C)), wInn/wBor (same sequence, FIG. 12D), and wRec (FIG. 12E) are all very similar to the structure from wMel. Indeed, all exhibit a 5α-helix bundle, connected by a long, flexible linker to another 4α-helix bundle. This is despite wide variation in amino acid sequence (e.g., wBif Wmk has a 26.2% amino acid sequence identity to wMel Wink, which represent the most distantly related protein pair). Table 6 shows amino acid pairwise percent identity between wMel Wmk and homologs from known male-killers. This similarity in overall protein structure despite sequence divergence suggests that the homologs may retain the same general function, but have perhaps adapted to target(s) that are divergent across host species, such as different DNA sequences of homologous genes.

In addition, the amino acid divergence across homologs of Wmk including the wBif homolog and all homologs are shown in FIG. 11. These results demonstrated that there is relatively high conservation overall across the protein (FIG. 14), but there are two areas of high variability directly adjacent to the two HTH DNA-binding domains that may be important for functional differences across strains or hosts (FIG. 14(B)).

Discussion

This example reports five key results showing wmk is a phage WO male-killing gene: (i) The gene occurs on a shortlist of candidate phage WO genes in Wolbachia male-killers, including the highly reduced phage WO genome of wRec and the divergent phage WO genome of wBif. (ii) wmk is common, divergent in sequence, and located in the eukaryotic association module of phage WO that is enriched with genes of eukaryotic function and homology. In this region, wmk is a few genes away from the two causative cytoplasmic incompatibility genes, cifA and cif/3. (iii) Transgenic expression of wmk consistently induces a male-killing-like phenotype spanning male-biased, early embryonic death coupled with expression in embryos and canonical cytological defects. (iv) Wink's predicted structure is conserved across arthropod hosts despite sequence divergence. (v) Finally, no other tested transgenes result in this phenotype, and wmk does not fit the profile of any other known form of reproductive parasitism.

The analyses herein indicate that Wink is a putative DNA-binding transcriptional regulator (FIG. 12). If this is indeed the case, it would be aligned with previous studies demonstrating *Wolbachia*'s ability to modulate host transcription to induce various phenotypes. *Wolbachia* would therefore be interfering with regulatory processes for host gene expression in males, which is the likely cause of male death. In addition, *Wolbachia* influence on host transcription has been implicated in the CI phenotype and virus inhibition, as two examples.

There is considerable amino acid sequence divergence in Wink homologs across several arthropod orders that harbor male-killing *Wolbachia*. One potential reason for the divergence is that if it a single gene kills many or all of these hosts in nature, it may be divergent due to selection to target the varied genetic and cellular bases of sex determination in these hosts. Second, if there is a single gene behind the phenotype, it could explain the relatively high frequency of host resistance since hosts would only have to counter-adapt to one gene product rather than multiple products. Under antagonistic coevolution, wmk would evolve to kill males, the host would adapt to resist the male killing, and wmk would follow suit and adapt again, continuing the evolutionary arms race. Third, in addition to coevolutionary bouts of wmk adaptation and host counter-adaptation, pleiotropy or neutral evolution of wmk could also explain the sequence divergence in wmk homologs, especially in hosts that do not exhibit male killing. In addition, there is difference in copy number of homologs across genomes, however, wmk is the most likely candidate as wRec only contains one homolog and it is most similar to wmk rather than others in the wMel genome.

Identification of male-killing genes have relevance to translational applications in pest or vector control as male killing can be used in population suppression to crash target populations. The use of male killing in conjunction with other population-crashing techniques like Sterile Insect Technique (SIT), where sterilized males are released to compete with fertile males, could decrease the time to crash the population and increase the chances of success. In this context, male killing genes can be used to transform an endosymbiotic microbe or host to either add or enhance male-killing ability. Alternatively, a male-killing infection could be established in a host where one does not natively exist. These techniques may be desirable in cases of invasive species of disease-carrying mosquitoes or agricultural pests. Techniques like SIT can fail if males are not completely sterile or because of reduced mating competitiveness with fertile males. Therefore, a two-pronged approach to simultaneously reduce viable matings in the wild (SIT) while killing off males (male-killing) could be used to effectively crash populations prone to SIT failure on their own.

The discovery of wmk-induced male killing brings a new understanding to the types of prophage genes that can interact with animal reproduction. Male-specific lethality occurs in many arthropods and has important influences on arthropod evolution[3,15,27-30], such as modifying mate choice and selecting for male resistance to the phenotype[31,32]. Male killing may also serve as a means to speed up other population suppression methods for vectors or pests[9]. Thus, deciphering male-killing genes helps inform the crosstalk between reproductive parasites and their animal hosts as well as their potential efficacy in arthropod control programs[6,9].

Materials and Methods

Comparative Genomics and Evolutionary Analysis

Putative Wmk domains were identified by a CD-SEARCH of NCBI's Conserved Domain Database (https://www.ncbi.nlm.nih.gov/Structure/cdd/wrpsb.cgi). For the full-length wmk analysis (FIG. 11a), homologs were identified by a BLASTn of NCBI's nucleotide collection (nr/nt) and whole genome shotgun sequence (wgs) databases. The sequences that are included are all taxa that were reciprocal best BLAST hits with wMel wmk. Partial sequences and/or those located at the end of a contig were excluded from downstream analysis. For the comparative genomic analysis, wmk, cifA, and cifB homologs were identified by manual annotations of prophage WO regions within known male-killing strains. Homology was confirmed by translating each gene and performing a BLASTp search against wMel in NCBI. Only sequenced male-killing *Wolbachia* genomes in *Drosophila* were compared to demonstrate homologs clustering with gene synteny (FIG. 11b). For both phylogenetic analyses, sequences were aligned using the MUSCLE plugin in Geneious Pro v8.1.7 and all indels were stripped. Trees were built using the MrBayes plugin in Geneious and were based on the best models of evolution, according to the corrected Akaike Information Criteria (AICc), as estimated by ProtTest v3.4.2. Protein modeling was performed with Phyre 2.

*Wolbachia* Gene Sequencing:

The *Wolbachia* genome of *D. innubila* (wInn) was provided by R. Unckless. The *Wolbachia* genomes of *D. bifasciata* (wBif) and *D. borealis* (wBor) were provided by F. Jiggins. The whole genomes will be published by the respective contributors at a later date, and only the gene regions involved in this publication are currently publicly available (the regions in FIG. 4).

The *D. innubila Wolbachia* genome was sequenced from a single wild-caught female. Briefly, *D. innubila* were captured at the Southwest Research Station over baits consisting of store-bought white button mushrooms (Agaricus bisporus). DNA was extracted using the Qiagen Gentra Puregene Tissue kit (#158689, Germantown, Maryland, USA). A genomic DNA library was constructed for several individuals using a modified version of the Nextera DNA Library Prep kit (#FC-121-1031, Illumina, Inc., San Diego, CA, USA) reagents[33]. DNA from an infected female was sequenced on a fraction of an Illumina HiSeq 2500 System Rapid-Run to generate 14873460 paired-end 150 base-pair reads. Reads were aligned to a draft *D. innubila* genome and all non-aligned reads were assembled de novo using Spades[34]. Those contigs blasting to other *Wolbachia* accessions were retained as putative *Wolbachia* genomic contigs.

The *Wolbachia* genomes of wBif and wBor were sequenced from *D. bifasciata* (line bif-F-MK[35]) and *D. borealis* (line PG05.16[36]) respectively. Following the protocol developed in Ellegaard et al.[37], *Wolbachia* cells were purified from ~20 freshly laid (less than 2 hours) and bleach-dechorionated embryos by homogenizing them in phosphate-buffered saline solution (PBS) and conducting a series of centrifugation/filtration steps as explained in Ellegaard et al[37]. A multiple-displacement amplification was carried out directly on the bacterial pellet using the Replig midi kit (Qiagen). The amplified DNA was cleaned with QIAamp DNA mini kit (Qiagen). From each sample, both 3 kb mate-pair and 50 bp paired-end DNA libraries were prepared and sequenced on a 454 Roche FLX (Department of Biochemistry, Cambridge, UK) and Illumina HiSeq2000 instruments (The Genome Analysis Center, Norwich, UK) respectively. The sequencing generated 203,565 and 239,485 454 mate-pair reads as well as 35,415,012 and 30,624,138 Illumina reads for wBif and wBor respectively. De novo hybrid assemblies combining 454 reads and a 10% subset of the Illumina reads were performed in Newbler (454 Life Sciences Corp., Roche, Branford, CT 06405, US). Contigs blasting to other *Wolbachia* accessions were retained as putative *Wolbachia* genomic contigs. Scaffolds were extended to fill regions with "N"s using GapFiller v.1-11[38].

*Drosophila* Strains:

The *Wolbachia* transgene strains were generated as described previously[10]. WD0626 (wmk) and WD0034 (control gene) were both inserted into an attP site in the BSC8622 (WT) line of genotype $y^1w^{67c23}$; P[CaryP]P2 obtained from the Bloomington *Drosophila* Stock Center. WD0625 was inserted into the BSC9723 strain, with a genotype of $y^1M$ [vas-int.Dm]ZH-2A w*; PBac[y+-attP-3B]VK00002. WD0508 was inserted into the $y^1M$[vas-int.Dm]ZH-2A w*; P[CaryP]attP40 line. The Act5c-Ga14/CyO driver line is the same background as BSC25374, which is $y^1w$*; P[Act5C-GAL4-w]E1/CyO. The maternal triple driver (MTD) strain BSC31777, genotype P[w[+mC]=otu-GAL4::VP16.R]1, w[*];P[w[+mC]=GAL4-nos.NGT]40; P[w[+mC]=GAL4::VP16-nos.UTR]CG6325[MVD1], was provided by J. Nordman. The expression experiments were done using $y^1w$* flies to measure native *Wolbachia* gene expression. The nanos-Gal4 strain used in FIG. 6*b,c* was previously described[10].

*Drosophila* Rearing:

*D. melanogaster* were reared on 4% cornmeal (w/v), 9% molasses (w/v), 1.6% yeast (w/v) (CMY) media. The flies developed at 25° C. at 80% humidity with a 12 h light/dark cycle. Virgin flies were stored at room temperature after collections. During virgin collections, stocks were maintained at 25° C. during the day and at 18° C. at night. *Wolbachia*-uninfected transgene or driver lines were generated via tetracycline treatment of infected lines as described previously[10].

Crossing Scheme: Experimental Design

Most *Drosophila* experiments (unless otherwise noted) were set up with the following design. Unless otherwise stated, crosses in each experiment were conducted by crossing 10 female heterozygous Act5c-Ga4/CyO driver flies to 2 male homozygous transgene flies (both uninfected, unless otherwise noted: switching the gender for each genotype does not alter the effect, data not shown). The offspring of these crosses were used for all experiments, except where noted. As the Act5c-Gal4/CyO driver strain is heterozygous, when driver flies are crossed to homozygous transgene flies, half of the offspring express the gene (those that inherit the Act5c driver gene that produces the Gal4 transcription factor), while the other half do not (those that inherit the CyO chromosome, which does not produce Gal4). Therefore, expressing males, expressing females, non-expressing males, and non-expressing females are expected in equal proportions under Mendelian inheritance. These four genotypes can only be visibly assessed in adulthood. Visually, embryos cannot be distinguished (except when fixed for microscopy with the Y chromosome FISH probe, when sex can be distinguished), while larvae can only be differentiated by sex.

Alongside several experiments, including the cytology, sex ratios were measured concurrently. When flies were set up in the crosses described above, siblings were also set up in vials with CMY media. The protocol to measure sex ratios was then followed to obtain sex ratios side by side with these experiments.

The MTD driver was tested by crossing this homozygous driver strain to homozygous transgene flies in the same design as above. This crossing leads to gene expression in all offspring because the driver is homozygous. Females expressing the transgene in their ovaries (MTD leads to targeted gene expression in the germline, specifically by loading embryos with the product) were then crossed to WT flies. Offspring were then quantified to measure sex ratios.

Sex Ratio Measurements:

To assess the ability of transgene expression to alter sex ratios, twenty replicates of 10 uninfected, 4-7 day old female driver flies and 2 uninfected, 1-2 day old male transgene flies were set up in vials with CMY media (except FIG. 13, where indicated). They were left on the food to lay eggs for 36 h at 25° C. and adults were then discarded. Once the offspring emerged, they were scored for both sex and expression or non-expression, which was determined by presence or absence of the CyO wing phenotype as well as with eye color markers associated with Act5c-Gal4 and the transgene insertion. Any vials with fewer than 50 adult offspring were removed from the analysis (except FIG. 13), as this indicates either poor egg laying or abnormally low egg hatching (average=120 offspring).

Hatch Rate:

To assess the hatch rate, 32 replicates each of 10 uninfected, 4-7 day old Act5c-Ga14/Cy0 females and 2 uninfected, 1-2 day old transgene males were set up in 8 oz, round bottom *Drosophila* polypropylene stock bottles. The hatch rate was then conducted as described previously[10]. After the embryo hatch counting, the sex of third instar larval offspring from each replicate was visually confirmed, and they were moved into their own CMY media vial where they developed to adulthood. The sex ratio of surviving adult offspring was then quantified. Any crosses with fewer than 50 embryos were not included in the analysis.

Hatch rates (for FIG. 6*b,c*) were performed as previously described with the nanos-Gal4 driver[10]. The nanos driver was used to test induction of CI instead of Act5c-Gal4/CyO since it is expressed more specifically in the gonads where CI effects occur and since it has been validated in the past for CI[10].

Embryo Cytology:

Eight stock bottles were set up per genotype, each with 60 uninfected, 4-7 day old Act5c-Gal4/Cy0 females and 12 uninfected, 1-2 day old transgene or WT males. Grape juice agar plates, made as described previously[10], with a small amount of baker's yeast (Red Star) were placed on each bottle opening and fixed on with tape. They were then placed with the grape plate down in a 25° C. incubator overnight (~16 hr). Then, the grape plates were replaced with fresh plates and fresh yeast. The flies were then allowed to lay eggs in 1 h increments, replacing the previous plates with fresh ones each time. They were then allowed to sit at room temperature for 1 h (embryos 1-2 h old), 3 h (3-4 h old), or 16 h (16-17 hold). Once they had reached the desired point in development, the embryos were fixed and stained, using a slight modification of the protocol outlined by Cheng et al. 2016[39]. Briefly, the embryos were dechorionated in 50% bleach and fixed for 15 minutes in a 1:1 4% paraformaldehyde: heptane mixture while shaking on a tabletop vortexer at about 150 rpm. The solution was discarded and the embryos were then devitellinized in a 1:1 heptane:methanol mixture by shaking vigorously for one minute. The solution was removed and the embryos were placed in fresh methanol and stored at 4° C. until the next steps were done, at least 16 h later. Then, the methanol was removed and the embryos were rehydrated in a series of methanol:water solutions, in the order of 9:1, then 1:1, then 1:9, each for 15 minutes while mixing on a Nutator. They were then treated with 10 mg/mL RNase A (Clontech Labs) by incubating them at 37° C. for 2-3 hr with enough RNase solution to cover the embryos. Once the RNase was removed, the embryos were washed three times for 5 min each in PBST (1×PBS, 0.1% Tween 20), while mixing on the Nutator. They were then re-fixed in 4% paraformaldehyde for 45 minutes with mixing and were then washed or incubated with several solutions with mixing on the nutator. First, they were washed three times in saline-sodium citrate/Tween 20 buffer (SSCT, 2×SSC buffer, 0.1% Tween 20) for 10 minutes each. They were then incubated with a series of SSCT/formamide solutions for 10 minutes each in the following order: 80% SSCT/20% formamide, 60% SSCT/40% formamide, 50% SSCT/50% formamide. Then fresh 50% SSCT/50% formamide was added and the embryos were incubated at 37° C. for 1 h. The solution was removed, and the embryos were then hybridized with the Y-chromosome FISH probe. This was done by mixing 36 μL FISH hybridization solution (1 g dextran sulfate, 1.5 mL 20×SSC, 5 mL formamide, to 15 mL with DNase-free water)[40], 3 μL DNase-free water, and 1 μL 200 ng/μL Y-chromosome FISH probe (sequence 5'-AATACAATACAATACAATACAATACAATAC-3' (SEQ ID NO:23) synthesized with Cy5 conjugated to the 5'end (IDT)) using the sequence published by Cheng et al. 2016[39]. Hybridization was done in a thermocycler by denaturing at 92° C. for 3 min, followed by hybridizing at 37° C. overnight (~16 h). Then, the embryos were again washed in a series of solutions on the nutator. They were done in the order of three 15 min 50% SSCT/50% formamide washes, one 10 min 60% SSCT/40% formamide wash, one 10 min 80% SSCT/20% formamide wash, and three 10 min SSCT washes. They were then mounted on glass slides with ProLong Diamond Antifade (Life Technologies) mounting media that contained 1 μg/mL propidium iodide (Sigma Aldrich).

Imaging was performed at the Vanderbilt University Cell Imaging Shared Resource (CISR) with a Zeiss LSM 510 META inverted confocal microscope. Image analysis and preparation was done with ImageJ software. Image brightness and contrast were adjusted for visibility, but adjustments were applied equally across each whole image.

Gene Expression:

Gene expression in embryos from FIG. 10 was measured in each of four groups. Group 1 was generated in crosses between Act5c-Gal4/CyO uninfected females crossed to wmk uninfected males. Group 2 was generated in crosses between Act5c-Gal4/CyO uninfected females crossed to control gene uninfected males. Group 3 was generated by crossing y$^1$w* infected females to y$^1$w* uninfected males. Group 4 was generated by crossing wBif-infected *D. bifasciata* females to uninfected *D. bifasciata* males. For each group, 8 bottles were set up with 10 females and 2 males. A grape juice agar plate[10] with yeast was placed in each bottle. These were placed in a 25° C. incubator overnight (16 h) for *D. melanogaster* or kept at 18° C. for *D. bifasciata*. Then, the plates were swapped with fresh ones. The flies were allowed to lay eggs for 1 h. The plates were then left at 25° C. or 18° C. for an additional 4 h to age them to be 4-5 hold (the estimated time of male death in wmk crosses). Embryos were then gathered in groups of 30 (each group from the same bottle) and flash frozen in liquid nitrogen. RNA was extracted using the Direct-zol RNA MiniPrep Kit (Zymo), DNase treated with DNA-free DNase (Ambion, Life Technologies), cDNA was generated with SuperScript VILO (Invitrogen), and RT-qPCR was run using iTaq Universal SYBR Green Mix (Bio-Rad). qPCR was performed on a Bio-Rad CFX-96 Real-Time System. Primers are listed in Table 4. Conditions were as follows: 50° C. 10 min, 95° C. 5 min, 40× (95° C. 10 s, 55° C. 30 s), 95° C. 30 s. For each gene measured, a standard curve was produced with known concentrations alongside samples with unknown concentrations. Primers are listed in Table 4. Differences in gene expression were done by calculating $2^{-\Delta ct}$ (difference in ct values of two genes of interest).

Confirmation of gene expression in adults from FIG. 5 was done similarly. Samples were obtained by flash freezing adult offspring laid by siblings of the flies used in FIG. 5a. Samples from FIG. 5b were from pooled, whole-body extractions from three males of each genotype. Samples from FIG. 5c were from pooled, whole-body extractions from three females of each genotype. Samples from 1e were from pooled, dissected ovaries of six adult female siblings of flies of flies used in FIG. 5e for each genotype. Samples were flash frozen in liquid nitrogen and then was processed (RNA extraction, DNase treatment, and cDNA treatment) as above. PCR was performed against positive controls (extracted DNA), negative controls (water), RNA, and cDNA. Gel image brightness and contrast were adjusted for visual clarity, but adjustments were applied equally across each whole image.

Protein Conservation

Protein conservation was calculated with the Protein Residue Conservation Prediction Tool (68http://compbio.cs.princeton.edu/conservation/score.html). Amino acid sequences from FIG. 11 along with the wBif Wmk homolog sequence were aligned using a MUSCLE alignment in Geneious Prime. This alignment was uploaded to the prediction tool with the following settings: Shannon entropy scores, a window size of zero, and no sequence weighting. Conservation values were then input into GraphPad Prism version 8 for visualization. HTH regions were indicated using the amino acids predicted to be in the domains according to the NCBI annotation of wMel Wmk.

Statistical Analyses:

Statistical analyses were done using GraphPad Prism software (version 5) or GraphPad online tools. For comparisons among only two data categories, the two-tailed, non-parametric Mann-Whitney U test was used. For comparisons with more groups, a non-parametric Kruskal-Wallis one-way analysis of variance was used, followed by Dunn's test for multiple comparisons if significant. In cases of comparisons among groups where only a single measurement was taken per group (such as cytology experiments), a Chi-square test was used. Exact tests used and other important information is listed in the figure legends of each experiment.

REFERENCES CITED IN THIS EXAMPLE

1 LePage, D. & Bordenstein, S. R. *Wolbachia*: Can we save lives with a great pandemic? *Trends Parasitol* 29, 385-393, doi:10.1016/j.pt.2013.06.003 (2013).

2 Brucker, R. M. & Bordenstein, S. R. Speciation by symbiosis. *Trends Ecol Evol* 27, 443-451, doi:10.1016/j.tree.2012.03.011 (2012).

3 Hornett, E. A. et al. Evolution of male-killer suppression in a natural population. *PLoS Biol* 4, e283, doi:10.1371/journal.pbio.0040283 (2006).

4 Bordenstein, S. R., O'Hara, F. P. & Werren, J. H. *Wolbachia*-induced incompatibility precedes other hybrid incompatibilities in Nasonia. *Nature* 409, 707-710, doi:10.1038/35055543 (2001).

5 Jaenike, J., Dyer, K. A., Cornish, C. & Minhas, M. S. Asymmetrical reinforcement and *Wolbachia* infection in *Drosophila*. *PLoS Biol* 4, e325, doi:10.1371/journal.pbio.0040325 (2006).

6 Hoffmann, A. A. et al. Successful establishment of *Wolbachia* in *Aedes* populations to suppress dengue transmission. *Nature* 476, 454-457, doi:10.1038/nature10356 (2011).

7 Dutra, H. L. et al. *Wolbachia* Blocks Currently Circulating Zika Virus Isolates in Brazilian *Aedes aegypti* Mosquitoes. *Cell Host Microbe* 19, 771-774, doi:10.1016/j.chom.2016.04.021 (2016).

8 Bordenstein, S. R. & Bordenstein, S. R. Eukaryotic association module in phage WO genomes from *Wolbachia*. Nat Commun 7, 13155, doi:10.1038/ncomms13155 (2016).

9 Berec, L., Maxin, D. & Bernhauerova, V. Male-killing bacteria as agents of insect pest control. *Journal of Applied Ecology* (2016).

10 LePage, D. P. et al. Prophage WO genes recapitulate and enhance *Wolbachia*-induced cytoplasmic incompatibility. *Nature* 543, 243-247, doi:10.1038/nature21391 (2017).

11 Pinto, S. B. et al. Transcriptional regulation of *Culex pipiens* mosquitoes by *Wolbachia* influences cytoplasmic incompatibility. *PLoS pathogens* 9, e1003647, doi:10.1371/journal.ppat.1003647 (2013).

12 Sutton, E. R., Harris, S. R., Parkhill, J. & Sinkins, S. P. Comparative genome analysis of *Wolbachia* strain wAu. *BMC genomics* 15, 928, doi: 10.1186/1471-2164-15-928 (2014).

13 Beckmann, J. F., Ronau, J. A. & Hochstrasser, M. A *Wolbachia* deubiquitylating enzyme induces cytoplasmic incompatibility. *Nature microbiology* 2, 17007, doi:10.1038/nmicrobiol.2017.7 (2017).

14 Hurst, G. D., Johnson, A. P., Schulenburg, J. H. & Fuyama, Y. Male-killing *Wolbachia* in *Drosophila*: a temperature-sensitive trait with a threshold bacterial density. *Genetics* 156, 699-709 (2000).

15 Jaenike, J. Spontaneous emergence of a new *Wolbachia* phenotype. *Evolution* 61, 2244-2252, doi:10.1111/j.1558-5646.2007.00180.x (2007).

16 Sasaki, T., Kubo, T. & Ishikawa, H. Interspecific transfer of *Wolbachia* between two lepidopteran insects expressing cytoplasmic incompatibility: a *Wolbachia* variant naturally infecting *Cadra cautella* causes male killing in *Ephestia kuehniella*. *Genetics* 162, 1313-1319 (2002).

17 Metcalf, J. A., Jo, M., Bordenstein, S. R., Jaenike, J. & Bordenstein, S. R. Recent genome reduction of *Wolbachia* in *Drosophila recens* targets phage WO and narrows candidates for reproductive parasitism. *PeerJ* 2, e529, doi:10.7717/peerj.529 (2014).

18 Petrella, L. N., Smith-Leiker, T. & Cooley, L. The Ovhts polyprotein is cleaved to produce fusome and ring canal proteins required for *Drosophila* oogenesis. *Development* 134, 703-712, doi:10.1242/dev.02766 (2007).

19 Landmann, F., Orsi, G. A., Loppin, B. & Sullivan, W. *Wolbachia*-mediated cytoplasmic incompatibility is associated with impaired histone deposition in the male pronucleus. *PLoS pathogens* 5, e1000343, doi:10.1371/journal.ppat.1000343 (2009).

20 Riparbelli, M. G., Giordano, R., Ueyama, M. & Callaini, G. *Wolbachia*-mediated male killing is associated with defective chromatin remodeling. *PloS one* 7, e30045, doi:10.1371/journal.pone.0030045 (2012).

21 Dyer, K. A. & Jaenike, J. Evolutionarily stable infection by a male-killing endosymbiont in *Drosophila innubila*: molecular evidence from the host and parasite genomes. *Genetics* 168, 1443-1455, doi:10.1534/genetics.104.027854 (2004).

22 Carson, H. L. A female-producing strain of *D. borealis* Patterson. *Drosoph. Inf. Serv* 30, 109-110 (1956).

23 Hornett, E. A. et al. You can't keep a good parasite down: evolution of a male-killer suppressor uncovers cytoplasmic incompatibility. *Evolution* 62, 1258-1263, doi:10.1111/j.1558-5646.2008.00353.x (2008).

24 Kelley, L. A., Mezulis, S., Yates, C. M., Wass, M. N. & Sternberg, M. J. The Phyre2 web portal for protein modeling, prediction and analysis. *Nature protocols* 10, 845-858, doi:10.1038/nprot.2015.053 (2015).

25 Kim, M. et al. Noncanonical DNA-binding mode of repressor and its disassembly by antirepressor. *Proceedings of the National Academy of Sciences of the United States of America* 113, E2480-2488, doi:10.1073/pnas.1602618113 (2016).

26 Luscombe, N. M., Austin, S. E., Berman, H. M. & Thornton, J. M. An overview of the structures of protein-DNA complexes. *Genome biology* 1, Reviews001, doi:10.1186/gb-2000-1-1-reviews001 (2000).

27 Engelstadter, J. & Hurst, G. D. The impact of male-killing bacteria on host evolutionary processes. *Genetics* 175, 245-254, doi:10.1534/genetics.106.060921 (2007).

28 Telschow, A., Hammerstein, P. & Werren, J. H. The effect of *Wolbachia* versus genetic incompatibilities on reinforcement and speciation. *Evolution* 59, 1607-1619 (2005).

29 Hurst, G. D. & McVean, G. A. T. Parasitic male-killing bacteria and the evolution of clutch size. *Ecological entomology* 23, 350-353 (1998).

30 Majerus, T. M. & Majerus, M. E. Intergenomic arms races: detection of a nuclear rescue gene of male-killing in a ladybird. *PLoS pathogens* 6, e1000987, doi:10.1371/journal.ppat.1000987 (2010).

31 Jiggins, F. M., Hurst, G. D. & Majerus, M. E. Sex-ratio-distorting *Wolbachia* causes sex-role reversal in its butterfly host. *Proc Biol Sci* 267, 69-73, doi:10.1098/rspb.2000.0968 (2000).

32 Hurst, G. D. & Jiggins, F. M. Male-killing bacteria in insects: mechanisms, incidence, and implications. *Emerg Infect Dis* 6, 329-336, doi:10.3201/eid0604.000402 (2000).

33 Baym, M. et al. Inexpensive multiplexed library preparation for megabase-sized genomes. *PloS one* 10, e0128036, doi:10.1371/journal.pone.0128036 (2015).

34 Bankevich, A. et al. SPAdes: a new genome assembly algorithm and its applications to single-cell sequencing. *Journal of computational biology: a journal of computational molecular cell biology* 19, 455-477, doi:10.1089/cmb.2012.0021 (2012).

35 Longdon, B., Fabian, D. K., Hurst, G. D. & Jiggins, F. M. Male-killing *Wolbachia* do not protect *Drosophila bifasciata* against viral infection. *BMC microbiology* 12 Suppl 1, S8, doi:10.1186/1471-2180-12-s1-s8 (2012).

36 Sheeley, S. L. & McAllister, B. F. Mobile male-killer: similar *Wolbachia* strains kill males of divergent *Drosophila* hosts. *Heredity* 102, 286-292, doi:10.1038/hdy.2008.126 (2009).

37 Ellegaard, K. M., Klasson, L., Naslund, K., Bourtzis, K. & Andersson, S. G. Comparative genomics of *Wolbachia* and the bacterial species concept. *PLoS genetics* 9, e1003381, doi:10.1371/journal.pgen.1003381 (2013).

38 Boetzer, M. & Pirovano, W. Toward almost closed genomes with GapFiller. *Genome biology* 13, R56, doi:10.1186/gb-2012-13-6-r56 (2012).

39 Cheng, B., Kuppanda, N., Aldrich, J. C., Akbari, O. S. & Ferree, P. M. Male-Killing Spiroplasma Alters Behavior of the Dosage Compensation Complex during *Drosophila melanogaster* Embryogenesis. *Curr Biol* 26, 1339-1345, doi: 10.1016/j.cub.2016.03.050 (2016).

40 Sullivan, W., Ashburner, M. & Hawley, R. S. *Drosophila* protocols. (Cold Spring Harbor Laboratory Press, 2000).

SEQUENCES

WMK protein sequence (WP_010962718.1) (SEQ ID NO: 1)

```
  1 MANISIRYKI AQKVRSWRLK RGYTQKDLAG KIGVTYQVVL QYEKGTRKIS IEKLYAIAEV
 61 LSVGIIDLIP VSSEKICLKN EEEEILNLVR KYKTINDQEL RKVFYLLTKF TRVGEKSSKK
121 AEKVKIAKGM VKAGISVDIV SQAIGLSANE CVEEKTGSIY YQIGKKIKEW RLVREYTQKD
181 LAEKMDTTRD EISNYEQGRV AIPLEKLYAI AETLSISITD LLIEEDEIVE SELPDLIKEY
241 KKIESQELRY ALIKSLFESI QICEEKVKRA EKMKIAKDLV KGGISTDIIL QITGLSLGEI
301 QQI
```

WMK gene sequence (SEQ ID NO: 2)

```
  1 atggcaaata tctcgataag gtacaaaata gcacaaaaag taaggagctg gaggttaaag
 61 cgaggttata ctcaaaaaga tttagcggga aaaattggcg taacgtatca agtagtacta
121 caatatgaaa aaggaacacg taaaatttcg attgagaaat tgtatgctat agcagaagtg
181 ttatcggttg gcatcataga tcttattcct gtatcaagtg aaaaaatttg ccttaaaaac
241 gaagaagagg aaatattaaa tctagtaaga aaatataaca cgattaatga tcaagagttg
301 cgcaaggtgt tttacttgct aacaaaattt acccgagttg gtgagaaaag tagtaaaaaa
361 gcagagaagg taaaaattgc aaagggtatg gttaaagcag gaatttctgt tgatattgtt
421 tcacaagcaa ttggcctctc tgctaatgag tgtgttgaag aaaaaacagg ttctatctac
481 taccaaatag gaaaaaagat aaaagaatgg aggctagtga gagagtatac tcaaaaggat
541 ttggctgaga aaatggatac aacacgtgat gaaataagca actatgagca aggacgtgtg
601 gccattccac tggaaaaatt atatgcaata gcagaaacat tatcaattag cattacagat
661 ctgctcatga aggaagatga gatagtagaa agtgagctac ctgatttaat aaaagaatac
721 aaaaaaattg agagtcaaga attacgctat gcgctaataa aatctcttt tgaaagcata
781 caaatttgcg aagaaaaagt gaaaagagca gaaaagatga aaattgcaaa ggatttagtg
841 aaaggaggaa tttctaccga tattattttg caaataacag gcctctcttt aggtgaaatt
901 caacagattt aa
```

Tables

TABLE 1

| wmk homolog label | Strain | NCBI Accession | Reciprocal Best BLASTp to wMel | Reciprocal BLASTp E-value to Wmk |
|---|---|---|---|---|
| Wmk | wMel | WP_010962718.1 | WD0626 | 0 |
| wRec 0560 | wRec | WP_038198911.1 | WD0626 | 0 |
| wInn (0626) | wInn | * | WD0626 | 0 |
| wBor (0626) | wBor | * | WD0626 | 9.E-163 |
| wMel WD0255 | wMel | WP_010962465.1 | WD0255 | 2.E-153 |
| wMel WD0623 | wMel | WP_010962717.1 | WD0623 | 2.E-157 |
| wInn (0623) | wInn | * | WD0255 | 4.E-111 |
| wBor (0623) | wBor | * | WD0255 | 2.E-155 |
| wMel WD0508 | wMel | WP_010962645.1 | WD0508 | 5.E-108 |
| wMel WD0622 | wMel | WP_010962716.1 | WD0622 | 3.E-76 |
| wInn (0622) | wInn | * | WD0622 | 6.E-50 |
| wBor (0622) | wBor | * | WD0622 | 3.E-73 |
| wBif (0622) | wBif | * | WD0622 | 2.E-42 |
| wBif (0626) | wBif | * | WD0626 | 9.E-23 |

TABLE 2A

| wmk homolog label | Strain | Super group | NCBI Accession | Contig name | Genome/contig length | Homolog location | Locus Tag |
|---|---|---|---|---|---|---|---|
| wmk | wMel | A | AE017196.1 | | 1267782 | 611371-612282 | WD0626 |
| wHa 02320 | wHa | A | CP003884.1 | | 1295804 | 280755-281666 | wHa_02320 |
| wRi 005880 | wRi | A | CP001391.1 | | 1445873 | 632500-633411 | wRi_005880 |
| wRi 010540 | wRi | A | CP001391.1 | | 1445873 | 1138959-1139870 | wRi_010540 |
| wIncCu 02670 | wInc_Cu | A | CP011148.1 | | 1267840 | 611424-612335 | WG67_02670 |
| wPip 0239 | wPipPel | B | AM999887.1 | | 1482455 | 247657-248570 | WP0239 |
| wAu 0252 | wAu | A | LK055284.1 | | 1268461 | 250436-251356 | WPWAU_0252 |
| wAu 0691 | wAu | A | LK055284.1 | | 1268461 | 666201-667055 | WPWAU_0691 |
| wMelPop 03503 | wMelPop | A | AQQE01000043.1 | contig_00005_6 | 49467 | 26890-27801 | WMELPOP_03503 |
| wSuzi 042 | wSuzi | A | CAOU02000042.1 | wsuzi2_contig042 | 1972 | 266-1177 | N/A |
| wSuzi 009 | wSuzi | A | CAOU02000022.1 | wsuzi2_contig009 | 57878 | 263-1174 | N/A |
| wAna 0875 | wAna | A | AAGB01000100.1 | gdan_354 | 2888 | 1216-2127 | WwAna0875 |

TABLE 2A-continued

| wmk homolog label | Strain | Super group | NCBI Accession | Contig name | Genome/contig length | Homolog location | Locus Tag |
|---|---|---|---|---|---|---|---|
| wRec 0560 | wRec | A | JQAM01000018.1 | | 11989 | 519-1430 | wrec0560 |
| wNfe 31 | wNfe | A | LYUY01000031.1 | NODE_31 | 12399 | 703-1598 | N/A |
| wNpa 15a | wNpa | A | LYUX01000015.1 | NODE_15 | 19352 | 7720-8615 | N/A |
| wNfla 18a | wNfla | A | LYUW01000018.1 | NODE_18 | 19541 | 10921-11822 | N/A |
| wNleu 18a | wNleu | A | LYUV01000018.1 | NODE_18 | 19173 | 7718-8613 | N/A |
| wBol1b 0133 | wBol1-b | B | CAOH01000056.1 | contig 01_7 | 10792 | 9781-10692 | wBol1_0133 |
| wNpa 14 | wNpa | A | LYUX01000014.1 | NODE_14 | 19790 | 18117-19034 | N/A |
| wNfe 23 | wNfe | A | LYUY01000023.1 | NODE_23 | 14002 | 11199-12116 | N/A |
| wNfla 78a | wNfla | A | LYUW01000078.1 | NODE_78 | 5269 | 876-1793 | N/A |
| wNleu 8a | wNleu | A | LYUV01000008.1 | NODE_8 | 24767 | 18223-19140 | N/A |
| wWil 404a | wWil | A | AAQP01000017.1 | TSC#14030-0811.241101007000404 | 9036 | 2974-3894 | N/A |
| wDacB 06900 | wDacB | B | LSYY01000169.1 | Contig_72 | 3902 | 1742-2647 | TV41_06900 |
| wDacA 05595 | wDacA | A | LSYX01000020.1 | Contig_116 | 2049 | 23-908 | TV42_05595 |
| wAlbB 49002 | wAlbB | B | CAGB01000110.1 | contig00334-1405 | 6182 | 1185-2093 | WALBB_490002 |
| wCauB | wCauB | B | * | | | | N/A |
| wBor | wBor | A | * | | | | N/A |
| wInn | wInn | A | * | | | | N/A |

* Sequences identified during this study

TABLE 2B

| wmk homolog label | Strain | Super group | NCBI Accession | Contig name | Genome/contig length | Homolog location | Locus Tag |
|---|---|---|---|---|---|---|---|
| wIncSM 02660 | wInc_SM | A | CP011149.1 | | 1267664 | 611253-612163 | WH35_02660 |
| wSim 0298 | wSim | A | AAGC01000294.1 | gdsi_178 | 1164 | 1-742 | WwSim0298 |
| wAna 0166 | wAna | A | AAGB01000245.1 | gdan_78 | 1374 | 722-1374 | WwAna0166 |
| wPipMol 01121 | wPipMol | B | CTEH01000009.1 | LargeContigsSCcontig000009 | 12073 | 3137-4050 | WPM_01121 |
| wPipJHB 1378 | wPipJHB | B | ABZA01000018.1 | contig_1290 | 1879 | 838-1751 | C1A_1378 |
| wBol1b 0010 | wBol1-b | B | CAOH01000062.1 | contig 18_3 | 4184 | 3181-4084 | wBol1_0010 |
| wDacA 04625 | wDacA | A | LSYX01000092.1 | Contig_4 | 5785 | 1180-2095 | TV42_04625 |
| wPipMol 01211 | wPipMol | B | CTEH01000032.1 | LargeContigsSCcontig000032 | 1541 | 578-1489 | WPM_01211 |
| wPipJHB 1294 | wPipJHB | B | ABZA01000007.1 | contig_1303 | 29919 | 25707-26618 | C1A_1294 |

TABLE 3

| Organism | Accession | BLASTp E-value | RBB in wMel | Reciprocal BLASTp E-value to Wmk |
|---|---|---|---|---|
| *Wolbachia endosymbiont* of *Wuchereria bancrofti* (wWb) | WP_088415462.1 | 1.00E−36 | WD0626 | 6.00E−42 |
| *Wolbachia endosymbiont* strain TRS of *Brugia malayi* (wBm) | AAW70776.1 | 5.00E−22 | WD0626 | 2.00E−27 |
| *Wolbachia endosymbiont* of *Brugia malayi* (wBm) | WP_050707658.1 | 2.00E−19 | WD0626 | 5.00E−25 |
| *Wolbachia endosymbiont* of *Pratylenchus penetrans* (wPpe) | WP_070064999.1 | 1.00E−13 | WD0626 | 4.00E−19 |
| *Rickettsiales bacterium* Ac37b | WP_038602295.1 | 5.00E−11 | WD0626 | 2.00E−16 |
| *Ehrlichia canis* str. Oklahoma | AAK28679.1 | 8.00E−11 | WD0626 | 6.00E−16 |
| *Ehrlichia canis* str. Jake | WP_011305001.1 | 9.00E−11 | WD0626 | 6.00E−16 |
| *Candidatus Neoehrlichia lotoris* | WP_084229825.1 | 8.00E−10 | WD0626 | 5.00E−15 |

TABLE 4

| Gene | Primer Name | Primer Sequence |
|---|---|---|
| WD0626 (wmk) native | WD0626_F | AATTGGCCTCTCTGCTAATGAGTG (SEQ ID NO: 3) |
| | WD0626_R | CACGTCCTTGCTCATAGTTGCTTA (SEQ ID NO: 4) |
| WD0626 (wmk) transgene | WD0626opt_F | TCCAGTGAGCTCCGAAGAAGA (SEQ ID NO: 5) |
| | WD0626opt_R | CCACGCGGGTAAACTTTGTC (SEQ ID NO: 6) |
| WD0034 (control) native | WD0034_F | GGAAGAAACTTGCACACCACTTAC (SEQ ID NO: 7) |
| | WD0034_R | TGCTCTCCGACCATCTGGATATTT (SEQ ID NO: 8) |
| WD0034 (control) transgene | WD0034opt_F | TTAAGTACCCAGACGGACGC (SEQ ID NO: 9) |
| | WD0034opt_R | TCCTTGTTGTCGGGATAGCG (SEQ ID NO: 10) |
| WD0625 transgene | WD0625opt_F | CGCGAGATGGATGACCTGAA (SEQ ID NO: 11) |
| | WD0625opt_R | CTCGCGCTCACTATGTCCAA (SEQ ID NO: 12) |
| WD0508 transgene | WD0508opt_F | GACGTGCTGATCAAGAGCCT (SEQ ID NO: 13) |
| | WD0508opt_R | TGCCCACTGTCTTCAGGATG (SEQ ID NO: 14) |
| Wolbachia groEL standard | groELstd_F | GGTGAGCAGTTGCAAGAAGC (SEQ ID NO: 15) |
| | groELstd_R | AGATCTTCCATCTTGATTCC (SEQ ID NO: 16) |
| Wolbachia groEL | groEL_F | CTAAAGTGCTTAATGCTTCACCTTC (SEQ ID NO: 17) |
| | groEL_R | CAACCTTTACTTCCTATTCTTG (SEQ ID NO: 18) |
| WD0631 (cifA) native | WD0631_F | TGTGGTAGGGAAGGAAAGAGGAAA (SEQ ID NO: 19) |
| | WD0631_R | ATTCCAAGGACCATCACCTACAGA (SEQ ID NO: 20) |
| Rpl36 (*Drosophila*) | Rpl36_F | GTTTAATTCTCAAGTAACGTCATC (SEQ ID NO: 21) |
| | Rpl36_R | TGTCCAACATCCTCACC (SEQ ID NO: 22) |
| 5'Cy5 FISH probe Y chromosome (Cheng et al 2016) | 5'Cy5YChrome | AATACAATACAATACAATACAATACAATAC (SEQ ID NO: 23) |
| Wolbachia 16S | Wolb_F | GAAGATAATGACGGTACTCAC (SEQ ID NO: 24) |
| | Wolb_R3 | GTCACTGATCCCACTTTAAATAAC (SEQ ID NO: 25) |
| wBif wmk homolog | wmk_wBif_F | AGGTTCGTGATACGGTGTGT (SEQ ID NO: 26) |
| | wmk_wBif_R | ATCTGTGTACGCCCTCTTGC (SEQ ID NO: 27) |
| wBif groEL | wBif_groELF | CGGGTTATAAGATTGCAGAAGGTG (SEQ ID NO: 28) |
| | wBif_groEL_R | GAGATGCCACATCCAGCAATATTC (SEQ ID NO: 29) |
| wBif cifA homolog | wBif_CifA_F | GAGATGGCTTGTAGTTACTGTGTG (SEQ ID NO: 30) |
| | wBif_CifA_R | GACCTTTCCTTCGAATGCCACC (SEQ ID NO: 31) |

TABLE 5

Comparative genomic analysis of *Wolbachia* male-killing gene candidates.
After applying all criteria in the genomic analysis, seven candidates for *Wolbachia* male killing were identified. All seven gene candidates are listed with their functional annotation, locus tags from both wMel and the closely related wRec strain, and gene lengths. The results of a 1:1 BLASTP of the homologs are also shown as the percent coverage, E-value, and pairwise identity. WD0626 from wMel is the gene denoted here as WO-mediated killing or wmk.

|  |  |  | 1:1 BLASTP wRec:wMel | | | Gene Length (bp) | |
| --- | --- | --- | --- | --- | --- | --- | --- |
| Annotation | wMel Locus Tag | wRec Locus Tag | Ref-Seq Coverage | E-Value | Pairwise % Identity | wRec | wMel |
| Ankyrin Repeat | WD0550 | wRec0541 | 100% | 0 | 95% | 789 | 990 |
| Transcriptional Regulator | WD0626 | wRec0560 | 100% | 0 | 99% | 912 | 912 |
| Rpn (Recombination-promoting nuclease) | WD0627 | wRec0561 | 100% | 0 | 99% | 897 | 897 |
| Hypothetical Protein | WD0628 | wRec0562 | 100% | 0 | 100% | 540 | 540 |
| CifA (CI component) | WD0631 | wRec0566 | 100% | 0 | 99% | 1425 | 1425 |
| Rpn (Recombination-promoting nuclease) | WD0296 | wRec0561 | 81% | 0 | 88% | 897 | 912 |
| Phospholipase D | WD1243 | wRec1232 | 100% | 0 | 99% | 531 | 531 |

TABLE 6

Pairwise % identity of amino acids in wMel Wmk compared to homologs in male-killing strains.
Percentages represent pairwise % identity from using a Geneious alignment of each indicated amino acid sequence to the wMel Wmk sequence.

| Homolog | % aa similarity to wMel Wmk |
| --- | --- |
| wRec Wmk | 99.70% |
| wBol1b Wmk | 85.90% |
| wCaub Wmk | 83.30% |
| wInn/Bor Wmk | 77.90% |
| wBif Wmk | 26.20% |

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

We claim:

1. A genetically modified arthropod, said arthropod comprising:
    a gene encoding a male arthropod killing factor; and
    a promoter operably linked to the gene encoding the male arthropod killing factor;
    wherein the expression of the gene encoding the male arthropod killing factor in arthropod embryos causes a reduction in viable surviving male offspring in comparison to arthropod embryos not expressing the gene encoding the male arthropod killing factor; and
    wherein the male arthropod killing factor comprises the amino acid sequence SEQ ID NO:1, or an amino acid sequence at least 60% identical to SEQ ID NO:1.

2. The arthropod of claim 1, wherein the gene encoding the male arthropod killing factor is from a bacterium, a prophage, or a phage.

3. The arthropod of claim 2, wherein the gene encoding the male arthropod killing factor is from *Wolbachia*.

4. The arthropod of claim 3, wherein the male arthropod killing factor is wmk (WD0626).

5. The arthropod of claim 1, wherein the reduction in viable male offspring is greater than 10%.

6. The arthropod of claim 1, wherein the arthropod is an insect.

7. The arthropod of claim 6, wherein the insect is selected from the genera consisting of *Aedes, Culex* and *Anopheles*.

8. The arthropod of claim 7, wherein the insect is selected from the group consisting of *Aedes albopictus, Aedes aegypti* and *Aedes polynesiensis*.

9. The arthropod of claim 6, wherein the insect is *Drosophila* suzukii.

10. A method for controlling a population of target arthropods, comprising:
    providing a gene encoding a male arthropod killing factor, and a promoter operably linked to the gene encoding the male arthropod killing factor; and
    wherein the male arthropod killing factor comprises the amino acid sequence SEQ ID NO:1, or an amino acid sequence at least 60% identical to SEQ ID NO:1;
    transforming a population of arthropods with the gene encoding the male arthropod killing factor and the promoter operably linked to the gene encoding the male arthropod-killing factor; and
    releasing the population of arthropods amongst a population of target arthropods, wherein the release of the arthropods reduces the population of target arthropods.

11. The method of claim 10, wherein the gene encoding the male arthropod killing factor is from a bacterium, a prophage, or a phage.

12. The method of claim 11, wherein the gene encoding the male arthropod killing factor is from *Wolbachia*.

13. The method of claim 12, wherein the gene encoding the male arthropod killing factor is wmk (WD0626).

14. The method of claim 10, wherein the male arthropod killing factor comprises the amino acid sequence SEQ ID NO: 1.

15. The method of claim 10, wherein the reduction in viable male offspring is greater than 10%.

16. The method of claim 10, further comprising providing an additional method of arthropod control.

17. The method of claim 16, wherein the additional method of arthropod control is a sterile insect technique (SIT).

18. The method of claim 16, wherein the additional method of arthropod control is an incompatible insect technique (ITT).

19. A method for controlling a population of target arthropods, comprising:
providing a gene encoding a male arthropod killing factor, and a promoter operably linked to the gene encoding the male arthropod killing factor; and
wherein the male arthropod killing factor comprises the amino acid sequence SEQ ID NO:1, or an amino acid sequence at least 60% identical to SEQ ID NO:1;
genetically transforming a bacteria, phage, or prophage with the gene encoding the male arthropod killing factor operably linked to the promoter;
transinfecting a population of arthropods with the bacteria, phage, or prophage; and
releasing the population of arthropods amongst a population of target arthropods, wherein the release of the arthropods reduces the population of target arthropods.

\* \* \* \* \*

SEQUENCE LISTING

```
<160> NUMBER OF SEQ ID NOS: 31

<210> SEQ ID NO 1
<211> LENGTH: 303
<212> TYPE: PRT
<213> ORGANISM: Artificial Sequence
<220> FEATURE:
<223> OTHER INFORMATION: Synthetic construct

<400> SEQUENCE: 1

Met Ala Asn Ile Ser Ile Arg Tyr Lys Ile Ala Gln Lys Val Arg Ser
1               5                   10                  15

Trp Arg Leu Lys Arg Gly Tyr Thr Gln Lys Asp Leu Ala Gly Lys Ile
            20                  25                  30

Gly Val Thr Tyr Gln Val Val Leu Gln Tyr Glu Lys Gly Thr Arg Lys
        35                  40                  45

Ile Ser Ile Glu Lys Leu Tyr Ala Ile Ala Glu Val Leu Ser Val Gly
    50                  55                  60

Ile Ile Asp Leu Ile Pro Val Ser Ser Glu Lys Ile Cys Leu Lys Asn
65                  70                  75                  80
```

Glu Glu Glu Glu Ile Leu Asn Leu Val Arg Lys Tyr Lys Thr Ile Asn
                85                  90                  95

Asp Gln Glu Leu Arg Lys Val Phe Tyr Leu Leu Thr Lys Phe Thr Arg
            100                 105                 110

Val Gly Glu Lys Ser Ser Lys Lys Ala Glu Lys Val Lys Ile Ala Lys
        115                 120                 125

Gly Met Val Lys Ala Gly Ile Ser Val Asp Ile Val Ser Gln Ala Ile
    130                 135                 140

Gly Leu Ser Ala Asn Glu Cys Val Glu Glu Lys Thr Gly Ser Ile Tyr
145                 150                 155                 160

Tyr Gln Ile Gly Lys Lys Ile Lys Glu Trp Arg Leu Val Arg Glu Tyr
                165                 170                 175

Thr Gln Lys Asp Leu Ala Glu Lys Met Asp Thr Thr Arg Asp Glu Ile
            180                 185                 190

Ser Asn Tyr Glu Gln Gly Arg Val Ala Ile Pro Leu Glu Lys Leu Tyr
        195                 200                 205

Ala Ile Ala Glu Thr Leu Ser Ile Ser Ile Thr Asp Leu Leu Ile Glu
    210                 215                 220

Glu Asp Glu Ile Val Glu Ser Glu Leu Pro Asp Leu Ile Lys Glu Tyr
225                 230                 235                 240

Lys Lys Ile Glu Ser Gln Glu Leu Arg Tyr Ala Leu Ile Lys Ser Leu
                245                 250                 255

Phe Glu Ser Ile Gln Ile Cys Glu Glu Lys Val Lys Arg Ala Glu Lys
            260                 265                 270

Met Lys Ile Ala Lys Asp Leu Val Lys Gly Gly Ile Ser Thr Asp Ile
        275                 280                 285

Ile Leu Gln Ile Thr Gly Leu Ser Leu Gly Glu Ile Gln Gln Ile
    290                 295                 300

<210> SEQ ID NO 2
<211> LENGTH: 912
<212> TYPE: DNA
<213> ORGANISM: Artificial Sequence
<220> FEATURE:
<223> OTHER INFORMATION: Synthetic construct

<400> SEQUENCE: 2
atggcaaata tctcgataag gtacaaaata gcacaaaaag taaggagctg gaggttaaag      60
cgaggttata ctcaaaaaga tttagcggga aaaattggcg taacgtatca agtagtacta     120
caatatgaaa aaggaacacg taaaatttcg attgagaaat tgtatgctat agcagaagtg     180
ttatcggttg gcatcataga tcttattcct gtatcaagtg aaaaaatttg ccttaaaaac     240
gaagaagagg aaatattaaa tctagtaaga aaatataaaa cgattaatga tcaagagttg     300
cgcaaggtgt tttacttgct aacaaaattt acccgagttg gtgagaaaag tagtaaaaaa     360
gcagagaagg taaaaattgc aaagggtatg gttaaagcag gaatttctgt tgatattgtt     420
tcacaagcaa ttggcctctc tgctaatgag tgtgttgaag aaaaaacagg ttctatctac     480
taccaaatag gaaaaaagat aaaagaatgg aggctagtga gagagtatac tcaaaaggat     540
ttggctgaga aaatggatac aacacgtgat gaaataagca actatgagca aggacgtgtg     600
gccattccac tggaaaaatt atatgcaata gcagaaacat tatcaattag cattacagat     660
ctgctcatag aggaagatga gatagtgaaa agtgagctac tgatttaat aaaagaatac     720 aaaaaaattg agagtcaaga attacgctat gcgctaataa aatctctgtt tgaaagcata     780

```
caaatttgcg aagaaaaagt gaaaagagca gaaaagatga aaattgcaaa ggatttagtg      840
aaaggaggaa tttctaccga tattattttg caaataacag gcctctcttt aggtgaaatt      900
caacagattt aa                                                          912

<210> SEQ ID NO 3
<211> LENGTH: 24
<212> TYPE: DNA
<213> ORGANISM: Artificial Sequence
<220> FEATURE:
<223> OTHER INFORMATION: Synthetic construct

<400> SEQUENCE: 3
aattggcctc tctgctaatg agtg                                             24

<210> SEQ ID NO 4
<211> LENGTH: 24
<212> TYPE: DNA
<213> ORGANISM: Artificial Sequence
<220> FEATURE:
<223> OTHER INFORMATION: Synthetic construct

<400> SEQUENCE: 4
cacgtccttg ctcatagttg ctta                                             24

<210> SEQ ID NO 5
<211> LENGTH: 21
<212> TYPE: DNA
<213> ORGANISM: Artificial Sequence
<220> FEATURE:
<223> OTHER INFORMATION: Synthetic construct

<400> SEQUENCE: 5
tccagtgagc tccgaagaag a                                                21

<210> SEQ ID NO 6
<211> LENGTH: 20
<212> TYPE: DNA
<213> ORGANISM: Artificial Sequence
<220> FEATURE:
<223> OTHER INFORMATION: Synthetic construct

<400> SEQUENCE: 6
ccacgcgggt aaactttgtc                                                  20

<210> SEQ ID NO 7
<211> LENGTH: 24
<212> TYPE: DNA
<213> ORGANISM: Artificial Sequence
<220> FEATURE:
<223> OTHER INFORMATION: Synthetic construct

<400> SEQUENCE: 7
ggaagaaact tgcacaccac ttac                                             24

<210> SEQ ID NO 8
<211> LENGTH: 24
<212> TYPE: DNA
<213> ORGANISM: Artificial Sequence
<220> FEATURE:
<223> OTHER INFORMATION: Synthetic construct

<400> SEQUENCE: 8
tgctctccga ccatctggat attt                                             24
```

<210> SEQ ID NO 9
<211> LENGTH: 20
<212> TYPE: DNA
<213> ORGANISM: Artificial Sequence
<220> FEATURE:
<223> OTHER INFORMATION: Synthetic construct

<400> SEQUENCE: 9
ttaagtaccc agacggacgc                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic construct

<400> SEQUENCE: 10
tccttgttgt cgggatagcg                                              20

<210> SEQ ID NO 11
<211> LENGTH: 20
<212> TYPE: DNA
<213> ORGANISM: Artificial Sequence
<220> FEATURE:
<223> OTHER INFORMATION: Synthetic construct

<400> SEQUENCE: 11
cgcgagatgg atgacctgaa                                              20

<210> SEQ ID NO 12
<211> LENGTH: 20
<212> TYPE: DNA
<213> ORGANISM: Artificial Sequence
<220> FEATURE:
<223> OTHER INFORMATION: Synthetic construct

<400> SEQUENCE: 12
ctcgcgctca ctatgtccaa                                              20

<210> SEQ ID NO 13
<211> LENGTH: 20
<212> TYPE: DNA
<213> ORGANISM: Artificial Sequence
<220> FEATURE:
<223> OTHER INFORMATION: Synthetic construct

<400> SEQUENCE: 13
gacgtgctga tcaagagcct                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic construct

<400> SEQUENCE: 14
tgcccactgt cttcaggatg                                              20

<210> SEQ ID NO 15
<211> LENGTH: 20
<212> TYPE: DNA
<213> ORGANISM: Artificial Sequence
<220> FEATURE:
<223> OTHER INFORMATION: Synthetic construct

```
<400> SEQUENCE: 15
ggtgagcagt tgcaagaagc                                            20

<210> SEQ ID NO 16
<211> LENGTH: 20
<212> TYPE: DNA
<213> ORGANISM: Artificial Sequence
<220> FEATURE:
<223> OTHER INFORMATION: Synthetic construct

<400> SEQUENCE: 16
agatcttcca tcttgattcc                                            20

<210> SEQ ID NO 17
<211> LENGTH: 25
<212> TYPE: DNA
<213> ORGANISM: Artificial Sequence
<220> FEATURE:
<223> OTHER INFORMATION: Synthetic construct

<400> SEQUENCE: 17
ctaaagtgct taatgcttca ccttc                                      25

<210> SEQ ID NO 18
<211> LENGTH: 22
<212> TYPE: DNA
<213> ORGANISM: Artificial Sequence
<220> FEATURE:
<223> OTHER INFORMATION: Synthetic construct

<400> SEQUENCE: 18
caacctttac ttcctattct tg                                         22

<210> SEQ ID NO 19
<211> LENGTH: 24
<212> TYPE: DNA
<213> ORGANISM: Artificial Sequence
<220> FEATURE:
<223> OTHER INFORMATION: Synthetic construct

<400> SEQUENCE: 19
tgtggtaggg aaggaaagag gaaa                                       24

<210> SEQ ID NO 20
<211> LENGTH: 24
<212> TYPE: DNA
<213> ORGANISM: Artificial Sequence
<220> FEATURE:
<223> OTHER INFORMATION: Synthetic construct

<400> SEQUENCE: 20
attccaagga ccatcaccta caga                                       24

<210> SEQ ID NO 21
<211> LENGTH: 24
<212> TYPE: DNA
<213> ORGANISM: Artificial Sequence
<220> FEATURE:
<223> OTHER INFORMATION: Synthetic construct

<400> SEQUENCE: 21
gtttaattct caagtaacgt catc                                       24

<210> SEQ ID NO 22
<211> LENGTH: 17
```

<212> TYPE: DNA
<213> ORGANISM: Artificial Sequence
<220> FEATURE:
<223> OTHER INFORMATION: Synthetic construct

<400> SEQUENCE: 22
tgtccaacat cctcacc                                                  17

<210> SEQ ID NO 23
<211> LENGTH: 30
<212> TYPE: DNA
<213> ORGANISM: Artificial Sequence
<220> FEATURE:
<223> OTHER INFORMATION: Synthetic construct

<400> SEQUENCE: 23
aatacaatac aatacaatac aatacaatac                                    30

<210> SEQ ID NO 24
<211> LENGTH: 21
<212> TYPE: DNA
<213> ORGANISM: Artificial Sequence
<220> FEATURE:
<223> OTHER INFORMATION: Synthetic construct

<400> SEQUENCE: 24
gaagataatg acggtactca c                                             21

<210> SEQ ID NO 25
<211> LENGTH: 24
<212> TYPE: DNA
<213> ORGANISM: Artificial Sequence
<220> FEATURE:
<223> OTHER INFORMATION: Synthetic construct

<400> SEQUENCE: 25
gtcactgatc ccactttaaa taac                                          24

<210> SEQ ID NO 26
<211> LENGTH: 20
<212> TYPE: DNA
<213> ORGANISM: Artificial Sequence
<220> FEATURE:
<223> OTHER INFORMATION: Synthetic construct

<400> SEQUENCE: 26
aggttcgtga tacggtgtgt                                               20

<210> SEQ ID NO 27
<211> LENGTH: 20
<212> TYPE: DNA
<213> ORGANISM: Artificial Sequence
<220> FEATURE:
<223> OTHER INFORMATION: Synthetic construct

<400> SEQUENCE: 27
atctgtgtac gccctcttgc                                               20

<210> SEQ ID NO 28
<211> LENGTH: 24
<212> TYPE: DNA
<213> ORGANISM: Artificial Sequence
<220> FEATURE:
<223> OTHER INFORMATION: Synthetic construct

<400> SEQUENCE: 28

```
cgggttataa gattgcagaa ggtg                                              24

<210> SEQ ID NO 29
<211> LENGTH: 24
<212> TYPE: DNA
<213> ORGANISM: Artificial Sequence
<220> FEATURE:
<223> OTHER INFORMATION: Synthetic construct

<400> SEQUENCE: 29
gagatgccac atccagcaat attc                                              24

<210> SEQ ID NO 30
<211> LENGTH: 24
<212> TYPE: DNA
<213> ORGANISM: Artificial Sequence
<220> FEATURE:
<223> OTHER INFORMATION: Synthetic construct

<400> SEQUENCE: 30
gagatggctt gtagttactg tgtg                                              24

<210> SEQ ID NO 31
<211> LENGTH: 22
<212> TYPE: DNA
<213> ORGANISM: Artificial Sequence
<220> FEATURE:
<223> OTHER INFORMATION: Synthetic construct

<400> SEQUENCE: 31
gacctttcct tcgaatgcca cc                                                22
```